(12) United States Patent
DeFrees et al.

(10) Patent No.: US 7,956,032 B2
(45) Date of Patent: *Jun. 7, 2011

(54) GLYCOPEGYLATED GRANULOCYTE COLONY STIMULATING FACTOR

(75) Inventors: Shawn DeFrees, North Wales, PA (US); David A. Zopf, Wayne, PA (US); Zhi-Guang Wang, Dresher, PA (US); Caryn Bowe, Doylestown, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 485 days.

This patent is subject to a terminal disclaimer.

(21) Appl. No.: 11/166,404

(22) Filed: Jun. 23, 2005

(65) Prior Publication Data

US 2007/0014759 A1    Jan. 18, 2007

Related U.S. Application Data

(63) Continuation-in-part of application No. PCT/US2004/041004, filed on Dec. 3, 2004.

(60) Provisional application No. 60/684,851, filed on May 25, 2005, provisional application No. 60/526,796, filed on Dec. 3, 2003, provisional application No. 60/539,387, filed on Jan. 26, 2004, provisional application No. 60/555,813, filed on Mar. 23, 2004, provisional application No. 60/570,282, filed on May 11, 2004, provisional application No. 60/592,744, filed on Jul. 29, 2004, provisional application No. 60/614,518, filed on Sep. 29, 2004, provisional application No. 60/623,387, filed on Oct. 29, 2004.

(51) Int. Cl.
   *A61K 38/31* (2006.01)
(52) U.S. Cl. ...................................................... 514/7.7
(58) Field of Classification Search ................ None
   See application file for complete search history.

(56) References Cited

U.S. PATENT DOCUMENTS

| | | | |
|---|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,438,253 A | 3/1984 | Casey et al. |
| 4,496,689 A | 1/1985 | Mitra |
| 4,565,653 A | 1/1986 | Ives et al. |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,925,796 A | 5/1990 | Bergh et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,169,933 A | 12/1992 | Anderson et al. |
| 5,182,107 A | 1/1993 | Friden |
| 5,194,376 A | 3/1993 | Kang |
| 5,202,413 A | 4/1993 | Spinu |
| 5,219,564 A | 6/1993 | Zalipsky et al. |
| 5,281,698 A | 1/1994 | Nitecki |
| 5,324,844 A | 6/1994 | Zalipsky |
| 5,342,940 A | 8/1994 | Ono et al. |
| 5,346,696 A | 9/1994 | Kim et al. |
| 5,352,670 A | 10/1994 | Venot |
| 5,369,017 A | 11/1994 | Wong et al. |
| 5,374,541 A | 12/1994 | Wong |
| 5,405,753 A | 4/1995 | Brossmer |
| 5,410,016 A | 4/1995 | Hubbell et al. |
| 5,432,059 A | 7/1995 | Bean |
| 5,446,090 A | 8/1995 | Harris |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,583,042 A | 12/1996 | Roth |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |

(Continued)

FOREIGN PATENT DOCUMENTS

EP    0474313 A    5/1992

(Continued)

OTHER PUBLICATIONS

Abeijon et al., 1986, J. Biol. Chem. 261(24):11374-11377.
Abuchowski et al., 1977, J. Biol. Chem. 252:3578-3581.
Abuchowski et al., 1977, J. Biol. Chem. 252:3582-3586.
Abuchowski et al., 1984, Cancer Biochem. Biophys. 7:175-186.
Ailor et al., 2000, Glycobiology 10:837-847.
Alam et al., 1998. Journal of Biotechnology. 65: 183-190.
Allegre et al., 2006, J. Membrane Science 269:109-117.
Altmann et al., 1999, Glycoconjugate J. 16:109-123.
Aplin et al., 1981, CRC Crit Rev. Biochem. 259-306.
Beauchamp et al., 1983, Anal Biochem.131:25-33.
Bedard et al., 1994, Cytotechnology 15:129-138.
Bennett et al., 1998, J. Biol. Chem. 273:30472-30481.
Bennett et al., 1999, FEBS Letters 460:226-230.
Berger et al., 1988, Blood 71:1641-1647.

(Continued)

*Primary Examiner* — Cecilia Tsang
*Assistant Examiner* — Thomas S Heard
(74) *Attorney, Agent, or Firm* — Leydig, Voit & Mayer, Ltd.

(57) ABSTRACT

The present invention provides conjugates between Granulocyte Colony Stimulating Factor and PEG moieties. The conjugates are linked via an intact glycosyl linking group that is interposed between and covalently attached to the peptide and the modifying group. The conjugates are formed from both glycosylated and unglycosylated peptides by the action of a glycosyltransferase. The glycosyltransferase ligates a modified sugar moiety onto either an amino acid or glycosyl residue on the peptide. Also provided are pharmaceutical formulations including the conjugates. Methods for preparing the conjugates are also within the scope of the invention.

10 Claims, 27 Drawing Sheets

U.S. PATENT DOCUMENTS

| | | | |
|---|---|---|---|
| 5,672,662 A | 9/1997 | Harris et al. | |
| 5,672,683 A | 9/1997 | Friden et al. | |
| 5,705,367 A | 1/1998 | Gotschlich | |
| 5,716,812 A | 2/1998 | Withers et al. | |
| 5,728,554 A | 3/1998 | Bayer et al. | |
| 5,770,420 A | 6/1998 | Lowe et al. | |
| 5,798,233 A | 8/1998 | Gotschlich | |
| 5,811,238 A | 9/1998 | Stemmer et al. | |
| 5,824,778 A | 10/1998 | Ishikawa et al. | |
| 5,824,864 A | 10/1998 | Fox et al. | |
| 5,830,721 A | 11/1998 | Stemmer et al. | |
| 5,833,988 A | 11/1998 | Friden | |
| 5,834,251 A | 11/1998 | Maras et al. | |
| 5,837,458 A | 11/1998 | Minshull et al. | |
| 5,849,535 A | 12/1998 | Cunningham et al. | |
| 5,858,751 A | 1/1999 | Paulson et al. | |
| 5,876,980 A | 3/1999 | DeFrees et al. | |
| 5,922,577 A | 7/1999 | Defrees et al. | |
| 5,932,462 A | 8/1999 | Harris et al. | |
| 5,945,314 A | 8/1999 | Prieto et al. | |
| 5,945,322 A | 8/1999 | Gotschlich | |
| 5,962,294 A | 10/1999 | Paulson et al. | |
| 5,969,040 A | 10/1999 | Hallahan et al. | |
| 5,977,307 A | 11/1999 | Friden | |
| 6,010,999 A | 1/2000 | Daley et al. | |
| 6,015,555 A | 1/2000 | Friden | |
| 6,030,815 A | 2/2000 | DeFrees et al. | |
| 6,037,452 A | 3/2000 | Minamino et al. | |
| 6,057,292 A | 5/2000 | Cunningham et al. | |
| 6,087,325 A | 7/2000 | Meers et al. | |
| 6,096,512 A | 8/2000 | Elhammer et al. | |
| 6,113,906 A | 9/2000 | Greenwald et al. | |
| 6,117,651 A | 9/2000 | Schultz et al. | |
| 6,166,183 A | 12/2000 | Ishikawa et al. | |
| 6,183,738 B1 | 2/2001 | Clark | |
| 6,261,805 B1 | 7/2001 | Wood | |
| 6,342,382 B1 | 1/2002 | Gotschlich | |
| 6,348,558 B1 | 2/2002 | Harris et al. | |
| 6,362,254 B2 | 3/2002 | Harris et al. | |
| 6,376,604 B2 | 4/2002 | Kozlowski | |
| 6,399,336 B1 | 6/2002 | Paulson et al. | |
| 6,399,337 B1 | 6/2002 | Taylor et al. | |
| 6,440,703 B1 | 8/2002 | DeFrees | |
| 6,465,220 B1 | 10/2002 | Hassan et al. | |
| 6,531,121 B2 | 3/2003 | Brines et al. | |
| 6,555,346 B1 | 4/2003 | Kretzdorn et al. | |
| 6,586,398 B1 | 7/2003 | Kinstler et al. | |
| 6,692,931 B1 | 2/2004 | Reutter et al. | |
| 6,716,626 B1 | 4/2004 | Itoh et al. | |
| 6,743,896 B2 | 6/2004 | Filpula et al. | |
| 6,780,624 B2 | 8/2004 | Gotschlich | |
| 6,800,740 B1 | 10/2004 | Cunningham et al. | |
| 6,949,372 B2 | 9/2005 | Betenbaugh et al. | |
| 7,125,843 B2 | 10/2006 | DeFrees et al. | |
| 7,138,371 B2 * | 11/2006 | DeFrees et al. | 514/8 |
| 7,157,277 B2 | 1/2007 | DeFrees et al. | |
| 7,179,617 B2 | 2/2007 | DeFrees et al. | |
| 7,202,208 B2 | 4/2007 | Papadimitriou | |
| 7,214,660 B2 | 5/2007 | DeFrees et al. | |
| 7,226,903 B2 | 6/2007 | DeFrees et al. | |
| 7,235,638 B2 | 6/2007 | Persson | |
| 7,265,084 B2 | 9/2007 | DeFrees et al. | |
| 7,276,475 B2 | 10/2007 | DeFrees et al. | |
| 7,297,511 B2 | 11/2007 | DeFrees et al. | |
| 7,304,150 B1 | 12/2007 | Egrie et al. | |
| 7,338,933 B2 | 3/2008 | DeFrees et al. | |
| 7,368,108 B2 | 5/2008 | DeFrees et al. | |
| 7,399,613 B2 | 7/2008 | DeFrees et al. | |
| 7,405,198 B2 | 7/2008 | DeFrees et al. | |
| 7,416,858 B2 | 8/2008 | DeFrees et al. | |
| 7,439,043 B2 | 10/2008 | DeFrees et al. | |
| 7,691,603 B2 | 4/2010 | DeFrees | |
| 7,696,163 B2 | 4/2010 | DeFrees et al. | |
| 2002/0016003 A1 | 2/2002 | Saxon et al. | |
| 2002/0037841 A1 | 3/2002 | Papadimitriou | |
| 2002/0115833 A1 | 8/2002 | Burg et al. | |
| 2002/0137134 A1 | 9/2002 | Gerngross et al. | |
| 2002/0142370 A1 | 10/2002 | Paulson et al. | |
| 2002/0150981 A1 | 10/2002 | Canfield | |
| 2002/0168323 A1 | 11/2002 | Gonda | |
| 2002/0182586 A1 | 12/2002 | Morris et al. | |
| 2003/0027257 A1 | 2/2003 | Iatrou et al. | |
| 2003/0040037 A1 | 2/2003 | Bayer | |
| 2003/0124645 A1 | 7/2003 | Paulson et al. | |
| 2003/0166525 A1 | 9/2003 | Hoffmann et al. | |
| 2003/0180835 A1 | 9/2003 | Bayer | |
| 2003/0186850 A1 | 10/2003 | Clausen et al. | |
| 2003/0207406 A1 | 11/2003 | Johnson et al. | |
| 2004/0043446 A1 | 3/2004 | DeFrees et al. | |
| 2004/0063911 A1 | 4/2004 | DeFrees et al. | |
| 2004/0077836 A1 | 4/2004 | DeFrees et al. | |
| 2004/0082026 A1 | 4/2004 | DeFrees et al. | |
| 2004/0102607 A1 | 5/2004 | Danishefsky et al. | |
| 2004/0115168 A1 | 6/2004 | DeFrees et al. | |
| 2004/0126838 A1 | 7/2004 | DeFrees et al. | |
| 2004/0132640 A1 | 7/2004 | DeFrees et al. | |
| 2004/0136955 A1 | 7/2004 | Barker et al. | |
| 2004/0137557 A1 | 7/2004 | DeFrees et al. | |
| 2004/0197875 A1 | 10/2004 | Hauser et al. | |
| 2005/0026266 A1 | 2/2005 | Clausen et al. | |
| 2005/0031584 A1 | 2/2005 | DeFrees et al. | |
| 2005/0064540 A1 | 3/2005 | DeFrees et al. | |
| 2005/0100982 A1 | 5/2005 | DeFrees et al. | |
| 2005/0106658 A1 | 5/2005 | DeFrees et al. | |
| 2005/0118672 A1 | 6/2005 | DeFrees et al. | |
| 2005/0143292 A1 | 6/2005 | DeFrees et al. | |
| 2005/0269265 A1 | 12/2005 | DeFrees | |
| 2005/0271690 A1 | 12/2005 | Gotschlich | |
| 2006/0024286 A1 | 2/2006 | Glidden | |
| 2006/0030521 A1 | 2/2006 | DeFrees et al. | |
| 2006/0035224 A1 | 2/2006 | Johansen | |
| 2006/0111279 A1 | 5/2006 | DeFrees et al. | |
| 2006/0177892 A1 | 8/2006 | De Frees | |
| 2006/0246544 A1 | 11/2006 | Kang et al. | |
| 2006/0287224 A1 | 12/2006 | DeFrees et al. | |
| 2007/0027068 A1 | 2/2007 | DeFrees et al. | |
| 2007/0032405 A1 | 2/2007 | DeFrees | |
| 2007/0059275 A1 | 3/2007 | DeFrees et al. | |
| 2007/0105755 A1 | 5/2007 | DeFrees et al. | |
| 2007/0154992 A1 | 7/2007 | DeFrees | |
| 2007/0254834 A1 | 11/2007 | DeFrees et al. | |
| 2007/0254836 A1 * | 11/2007 | Defrees et al. | 514/12 |
| 2008/0015142 A1 | 1/2008 | DeFrees et al. | |
| 2008/0050772 A1 | 2/2008 | DeFrees et al. | |
| 2008/0102083 A1 | 5/2008 | DeFrees et al. | |
| 2008/0108557 A1 | 5/2008 | Behrens et al. | |
| 2008/0146494 A1 | 6/2008 | DeFrees et al. | |
| 2008/0146782 A1 | 6/2008 | DeFrees et al. | |
| 2008/0176790 A1 | 7/2008 | DeFrees | |
| 2008/0187955 A1 | 8/2008 | DeFrees et al. | |
| 2008/0200651 A1 | 8/2008 | Ostergaard et al. | |
| 2008/0206808 A1 | 8/2008 | DeFrees et al. | |
| 2008/0206810 A1 | 8/2008 | Johnson et al. | |
| 2008/0207487 A1 | 8/2008 | DeFrees et al. | |
| 2008/0242607 A1 | 10/2008 | DeFrees | |
| 2008/0242846 A1 | 10/2008 | DeFrees et al. | |
| 2008/0248959 A1 | 10/2008 | DeFrees | |
| 2008/0253992 A1 | 10/2008 | DeFrees et al. | |
| 2008/0255026 A1 | 10/2008 | DeFrees et al. | |
| 2008/0255040 A1 | 10/2008 | DeFrees | |
| 2008/0274958 A1 | 11/2008 | DeFrees | |
| 2008/0280818 A1 | 11/2008 | DeFrees | |
| 2008/0300173 A1 | 12/2008 | DeFrees | |
| 2008/0300175 A1 | 12/2008 | DeFrees | |
| 2008/0305991 A1 | 12/2008 | DeFrees et al. | |
| 2008/0305992 A1 | 12/2008 | DeFrees et al. | |
| 2008/0318850 A1 | 12/2008 | DeFrees et al. | |
| 2008/0319183 A1 | 12/2008 | DeFrees et al. | |
| 2009/0028822 A1 | 1/2009 | DeFrees et al. | |
| 2009/0048440 A1 | 2/2009 | Felo et al. | |
| 2009/0053167 A1 | 2/2009 | DeFrees | |
| 2009/0054623 A1 | 2/2009 | DeFrees | |
| 2009/0055942 A1 | 2/2009 | Ostergaard et al. | |
| 2009/0093399 A1 | 4/2009 | DeFrees et al. | |
| 2009/0124544 A1 | 5/2009 | DeFrees | |
| 2009/0137763 A1 | 5/2009 | DeFrees et al. | |
| 2009/0143292 A1 | 6/2009 | Hinderer et al. | |

| | | | |
|---|---|---|---|
| 2009/0169509 A1 | 7/2009 | DeFrees et al. | |
| 2009/0176967 A1 | 7/2009 | Stennicke | |
| 2009/0203579 A1 | 8/2009 | Defrees et al. | |
| 2009/0227504 A1 | 9/2009 | Klausen et al. | |
| 2009/0252720 A1 | 10/2009 | Ostergaard et al. | |
| 2009/0292110 A1 | 11/2009 | DeFrees | |
| 2009/0305967 A1 | 12/2009 | DeFrees et al. | |
| 2010/0009902 A1 | 1/2010 | DeFrees | |
| 2010/0015684 A1 | 1/2010 | DeFrees et al. | |
| 2010/0028939 A1 | 2/2010 | Behrens et al. | |
| 2010/0035299 A1 | 2/2010 | DeFrees et al. | |
| 2010/0041872 A1 | 2/2010 | DeFrees et al. | |
| 2010/0048456 A1 | 2/2010 | DeFrees et al. | |
| 2010/0056428 A1 | 3/2010 | Behrens | |
| 2010/0075375 A1 | 3/2010 | DeFrees et al. | |
| 2010/0081791 A1 | 4/2010 | DeFrees et al. | |
| 2010/0120666 A1 | 5/2010 | Zopf et al. | |

FOREIGN PATENT DOCUMENTS

| | | |
|---|---|---|
| EP | 0585109 A | 3/1994 |
| EP | 0605963 A2 | 7/1994 |
| EP | 1428878 A1 | 6/2004 |
| JP | H03/503759 A | 8/1991 |
| WO | WO 87/00056 | 1/1987 |
| WO | WO 89/06546 A1 | 7/1989 |
| WO | WO 89/10134 A1 | 11/1989 |
| WO | WO 90/07572 | 7/1990 |
| WO | WO 90/08164 A1 | 7/1990 |
| WO | WO 90/08823 A1 | 8/1990 |
| WO | WO 90/13540 A1 | 11/1990 |
| WO | WO 91/14697 A1 | 10/1991 |
| WO | WO 92/18135 | 5/1992 |
| WO | WO 93/15189 A1 | 8/1993 |
| WO | WO 94/04193 A1 | 3/1994 |
| WO | WO 94/05332 | 3/1994 |
| WO | WO 94/09027 A1 | 4/1994 |
| WO | WO 94/15625 A1 | 7/1994 |
| WO | WO 94/17039 A1 | 8/1994 |
| WO | WO 94/18247 A1 | 8/1994 |
| WO | WO 95/02421 A1 | 1/1995 |
| WO | WO 96/40731 | 6/1996 |
| WO | WO 96/21469 A1 | 7/1996 |
| WO | WO 96/32491 | 10/1996 |
| WO | WO 97/05330 | 2/1997 |
| WO | WO 98/05363 | 2/1998 |
| WO | WO 87/05330 A1 | 7/1998 |
| WO | WO 98/31826 | 7/1998 |
| WO | WO 98/51784 A1 | 11/1998 |
| WO | WO 98/58964 | 12/1998 |
| WO | WO 99/00150 A2 | 1/1999 |
| WO | WO 99/14259 A1 | 3/1999 |
| WO | WO 99/22764 A1 | 5/1999 |
| WO | WO 99/34833 A1 | 7/1999 |
| WO | WO 99/45964 A1 | 9/1999 |
| WO | WO 00/23114 | 4/2000 |
| WO | WO 00/26354 A1 | 5/2000 |
| WO | WO 00/65087 | 11/2000 |
| WO | WO 01/02017 A2 | 1/2001 |
| WO | WO 01/49830 A2 | 7/2001 |
| WO | WO 01/58935 A2 | 8/2001 |
| WO | WO 01/60411 A1 | 8/2001 |
| WO | WO 01//76640 A2 | 10/2001 |
| WO | WO 01/88117 A2 | 11/2001 |
| WO | WO 02/02597 A2 | 1/2002 |
| WO | WO 02/13843 A2 | 2/2002 |
| WO | WO 02/13873 A1 | 2/2002 |
| WO | WO 02/53580 A2 | 7/2002 |
| WO | WO 02/074806 A2 | 9/2002 |
| WO | WO 02/002764 A2 | 10/2002 |
| WO | WO 02/092619 A2 | 11/2002 |
| WO | WO 03/017949 A2 | 3/2003 |
| WO | WO 03/031464 * | 4/2003 |
| WO | WO 03/046150 A2 | 6/2003 |
| WO | WO 2003/045980 A2 | 6/2003 |
| WO | WO 03/093448 A2 | 11/2003 |
| WO | WO 2004/009838 A2 | 1/2004 |
| WO | WO 2004/010327 A2 | 1/2004 |
| WO | WO 2004/033651 A2 | 4/2004 |
| WO | WO 2004/083258 A2 | 9/2004 |
| WO | WO 2004/083259 A2 | 9/2004 |
| WO | WO 2004/091499 A2 | 10/2004 |
| WO | WO 2004/096148 A2 | 11/2004 |
| WO | WO 2004/099231 A2 | 11/2004 |
| WO | WO 2004/103275 A2 | 12/2004 |
| WO | WO 2006/010143 A2 | 1/2005 |
| WO | WO 2005/012484 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | WO 2005/091944 A2 | 10/2005 |
| WO | WO 2005/121331 A2 | 12/2005 |
| WO | WO 2006/014349 A2 | 2/2006 |
| WO | WO 2006/014466 A2 | 2/2006 |
| WO | WO 2006/020372 A2 | 2/2006 |
| WO | WO 2006/031811 A2 | 3/2006 |
| WO | WO 2006/050247 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/105426 A2 | 10/2006 |
| WO | WO 2006/121569 A2 | 11/2006 |
| WO | WO 2006/127910 A2 | 11/2006 |
| WO | WO 2007/022512 A2 | 2/2007 |
| WO | WO 2007/056191 A2 | 5/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |

OTHER PUBLICATIONS

Berg-Fussman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., 1992, J. Biol. Chem., 266(17):11051-11057.
Boccu et al., 1983, Z. Naturforsch 38C:94-99.
Boime et al., 1995, Endocrinology 136:2635-2640.
Boissel et al., 1993, J. Biol. Chem. 268:15983-15993.
Bork (2000) Genome Research 10:398-400.
Bork et al. (1996) Trends in Genetics 12(10): 425-427.
Bouizar et al., 1986, Eur. J. Biochem. 155:141-147.
Boyd et al., 1995, Mol. Immunol. 32:1311-1318.
Brenner (1999) Trends in Genetics 15(4) 132-133.
Browning et al., 1989, J. Immunol. 143:1859-1867.
Bückmann et al., 1981, Makromol. Chem.182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.
Chaffee et al., 1992, J. Clin. Invest 89:1643-1651.
Charter et al., 2000, Glycobiology 10:1049-1056.
Chern et al., 1991, Eur. J. Biochem. 202:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.
Cointe, et al., 2000, Glycobiology, 10(5):511-519.
Conradt et al., 1987, J. Biol. Chem. 262:14600-14605.
Cope et al., 1991, Molecular Microbiology 5(5):1113-1124.
Copeland, Robert A., 2000, Enzymes, Second Edition, 146-150.
Crout et al., 1998, Curr. Opin. Chem. Biol. 2:98-111.
DeFrees, 2006, Glycobiology 16:833-843.
Delgado et al., 1992, Critical Reviews in Therapeutic 9:249-304.
Delgaldo et al., 1990, Biotechnol. Appl. Biochem. 12:119-128.
Detty et al., 1982, J. Org. Chem. 47:5416-5418.
Doerks et al. (1998) Trends in Genetics 14(6): 248-250.
Douglas, et al., 1991, J. Am. Chem. Soc., 113:5095-5097.

Dunn et al., 1991, Eds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J. Anat. 187:279-292.
Eavarone et al., 2000, J. Biomed Mater. Res. 51:10-14.
Fan et al., 1997, J. Biol. Chem. 272(43):27058-27064.
Fibi et al., 1995, Cells Blood 85:1229-1236.
Fischer et al., 1998, Thrombosis Research 89:147-150.
Flynn et al., 2000, Curr. Opin. Oncol. 12:574-581.
Fritz et al., 2004, PNAS 101(43):15307-15312.
Fritz et al., 2006, J. Biol. Chem. 281(13):8613-8619.
Garnett et al., 2002, Advanced Drug Delivery Reviews 53:171-216.
Gatot, et al., 1998, J. Biol. Chem., 273(21):12870-12880.
Gilbert et al., 1996, Cytotechnology 22:211-216.
Gillis et al., 1988, Behring Inst. Mitt. Aug. 83:1-7.
Ginns, Dr. Edward, PEG Glucocerebrosidase, Internet page from www.gaucher.org.uk/peg2.prg, printed Jun. 21, 2002.
Gotschlich, Emil C., 1994, J. Exp. Med., Coden: Jemeav; ISSN: 0022-1007, 180(6):2181-90.
Grabenhorst, et al., 1993, Euro. J. Biochem., 215:189-197.
Grodberg et al., 1993, Eur. J. Biochem. 218:597-601.
Gross, H.J., 1992, Eur. J. Biochem. 203(1-2):269-275.
Hagen et al., 1999, J. Biol. Chem. 274:27867-27874.
Hagen et al., 1999, J. Biol. Chem. 274:6797-6803.
Hagen et al., 2001, J. Biol. Chem. 276:17395-17404.
Hall et al., 2001, Methods in Molecular Biology 166:139-154.
Haneda et al., Carbohydr. Res. 292:61-70.
Hang et al., 2001, J. Am. Chem. Soc. 123:1242-1243.
Harris et al., 2003, Nature Reviews Drug Discovery, 2:214-221.
Harris et al., Abstracts of Papers of the American Chemical Society, 1991, V 201, APR, P 64-POLY, p. 154-155.
Harris, 1985, Macronol. Chem. Phys. C25: 325-373.
Hassan et al., 2000, J. Biol. Chem. 275:38197-38205.
Hayes et al., 1993, J. Biol. Chem. 268(22):16170-16178.
Hellstrom et al., 2001, Methods in Molecular Biology 166:3-16.
Hermanson et al., 1992, Immobilized Affinity Ligand Techniques, Academic Press.
Hermanson, 1996, Bioconjugate Techniques, Academic Press, San Diego.
Hermentin, et al., 1996, Glycobiology 6(2):217-230.
Hills et al., 2002, American Biotechnology Laboratory, 20(11):30.
Hink et al., 1991, Biotechnology Progress 7:9-14.
Hollister et al., 2001, Glycobiology 11:1-19.
Hounsell et al., 1996, Glycoconj. J. 13:19-26.
Ichikawa et al., 1992, J. Am. Chem. Soc. 114:9283-9298.
Ikonomou et al., 1991, In Vitro Cell. Dev. Biol.-Animal 37:549-559.
Inlow, et al., 1989, J. Tissue Culture Meth. 12:13-16.
Inoue et al., 1995, Biotechnology Annual Review 1:297-313.
Ito et al., 1993, Pure & Appl. Chem. 65(4):753-762.
Jackson et al., 1987, Anal. Biochem.165:114-127.
Jarvis et al., 1998, Curr. Opin. Biotechnol. 9:528-533.
Joppich et al., 1979, Makromol Chem. 180:1381-1384.
Joshi et al., 1990, J. Biol. Chem. 265:14518-14525.
Jung et al., 1983, Biochem. Biophys. Acta, 761:152-162.
Kalsner et al., 1995, Glycoconj. J. 12:360-370.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18: 835-841.
Koeller et al., 2001, Nature, 409:232-240.
Koide et al., 1983, Biochem Biophys. Res. Commun. 111:659-667.
Kreitmann 2001, Current Pharmaceutical Biotechnology 2:313-325.
Kuhn, et al., 1995, J. Biol. Chem. 270(49):29493-29497.
Lai et al, 1986, J. Biol. Chem. 261:3116-3121.
Lau et al. (1999) Journal of Biotechnology 75:105-115.
Lee et al., 1989, Biochemistry 28:1856-1861.
Lee-Huang et al., 1984, Proc. Natl. Acad. Sci. U.S.A. 81:2708-2712.
Leung, S., 1995, J. Immunology, 154:5919-5926.

Li et al., 2002, Trends in Pharmacological Sciences 23:206-209.
Li et al., 2002, Medicinal Research Reviews 22:225-250.
Licari P. et al., 1992, Biotechnology and Bioengineering 39(4):432-441.
Licari P. et al., 1992, Biotechnology and Bioengineering 39(9):932-944.
Liu et al., 2002, 1996, Chem. Eur. J. 2:1359-1362.
Long et al., 2006, Experimental Hematology 34:697-704.
Lord et al., 2001, Clin. Cancer Res. 7:2085-2090.
Lougheed et al., 1999, J. Biol. Chem. 274:37717-37722.
Luckow et al., 1993, Curr. Opin. Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maranga et al., 2003, Biotechnology and Bioengineering 84(2):245-253.
Maras et al., 2000, Journal of Biotechnology 77:255-263.
Miller et al., 1993, Curr. Opin. Genet. Dev. 3:97-101.
Min et al., 1996, Endocr. J. 43:585-593.
Mistry et al., 1996, Lancet 348:1555-1559.
Morimoto et al., 1996, Glycoconjugate J. 13:1013-1020.
NCBI—Accession No. NCAA26095 (2 pgs.).
NCBI—Accession No. NP_058697 (3 pgs.).
NCBI—Accession No. NP_999299 (2 pgs.).
NCBI Database hits for erythropoietin protein sequences (3 pgs.).
Ngo et al. (1994) "The Protein Folding Problem and Tertiary Structure Prediction, Chapter 14: Computational Complexity Protein Structure Prediction, and the Levinthal Paradox" pp. 433-440 and 492-495.
Nilsson et al., 1984, Methods Enzymol. 104:56-69.
O'Connell et al., 1992, J. Biol. Chem. 267:25010-25018.
Oetke, et al., 2002, J. Biol. Chem 277(8):6688-6695.
Olson et al., 1999, J. Biol. Chem. 274:29889-29896.
Palacpac et al., 1999, PNAS USA 96:4692-4697.
Park et al., 1986, J. Biol Chem. 261:205-210.
Paulson et al., 1997, J. Biol. Chem. 252:8624-8628.
Plummer et al., 1995, J. Biol. Chem. 270(22):13192-13196.
PNGase-F Amidase Sequence from F. Meningosepticum (Registry Nos. 128688-70-0).
PNGase-F Amidase Sequence from F. Meningosepticum (Registry Nos. 128688-71-1).
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Reis et al., 1991, Biotechnology and Bioengineering 38:413-422.
Rosenthal, et al., 1994, Methods Enzymol. 235:253-285.
Sadler et al., 1982, Methods in Enzymology 83:458-514.
Sandberg et al., 2000, Seminars in Hematology 38(2):4-12.
Saneyoshi et al., 2001, Biology of Reproduction 65:1686-1690.
Saxon et al., 2000, Science 287:2007-2010.
Schlaeger, E., 1996, Cytotechnology 20:57-70.
Schwientek et al., 1994, Gene 145:299-303.
Schwientek et al., 2002, J. Biol. Chem. 277:22623-22638.
Scouten 1987, Methods in Enzymology 135:30-65.
Shah et al., 1996, J. Pharm. Sci. 85:1306-1311.
Shapiro et al., 2005, B. Biochemistry 105:518-525.
Singh et al., 1996, Chem. Commun. 1996:993-994.
Sinha et al., 1980, Infection and Immunity 29(3):914-925.
Skolnick et al. (2000) Trends in Biotech. 18(1): 34-39.
Smith et al. (1997) Nature Biotechnology 15:1222-1223.
Song et al., 2002, J. Pharmacol. Exp. Ther. 301:605-610.
Srinivasachar et al., 1989, Biochemistry 28:2501-2509.
Stephens et al., 1983, European J. of Biochem., 133(1):155-62.
Stephens et al., 1983, European J. of Biochem., 133(3):481-9.
Stephens et al., 1983, European J. of Biochem., 135(3):519-27.
Takane et al., 2000, J. Pharmacology and Experimental Therapeutics 294:746-752.
Takeda et al., 1995, Trends Biochem. Sci. 20:367-371.
Takeuchi, et al., 1990, The Journal of Biological Chemistry, 265(21): 12127-12130.
Tanner et al., 1987, Biochim. Biophys. Acta., 906:81-91.

Taylor et al., 1991, Protein Immobilization Fundamentals and Applications, Manual.
Tenno et al., 2002, J. Biol. Chem. 277(49):47088-96.
Thotakura et al., 1987, Meth Enzymol 138: 350-359.
Tsuboi et al., 2000 Archives of Biochemistry and Biophysics 374:100-106.
Tuddenham, E., 2002, Nature 419:23-24.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog, 296:171-179.
Van Berkel et al., 1996, Biochem J. 319:117-122.
Veronese et al., 1985, Appl. Biochem. Biotech. 11:141-152.
Vocadlo et al., 2000, In Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wang, M., 1998, Protein Engineering 11(12):1277-1283.
Wellhoner et al., 1991, J. Biol. Chem. 226:4309-4314.
Wells (1990) Biochemistry 29(37): 8509-8517.
Witte K. et al., 1997, J. Am. Chem. Soc. 119:2114-2118.
Woghiren et al., 1993, Bioconjugate Chem. 4:314-318.
Wong et al., 1992, Enzyme Microb.Technol. 14:866-874.
Wong et al., 1996, Biotechnology and Bioengineering 49:659-666.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Yoshitake et al., 1985, Biochemistry 24:3736-3750.
Zalipsky 1995, Bioconjugate Chem. 6:150-165.
Zalipsky et al., 1992, Poly(ethylene glycol) Chemistry: Biotechnical and Biomedical Applications 347-370.
Zheng et al., 1999, Biotechnology and Bioengineering 65(5):600-604.
Zhou, et al., 1994, Mol. Microbiol. 14(4):609-618.
Abuchowski et al., *J. Biol. Chem.*, 252(11): 3582-3586 (1977).
Barrios et al., *J. Mol. Recognit.*, 17(4):332-338 (2004).
Boime et al., *Recent Prog. Horm. Res.*, 54: 271-289 (1999).
Brockhausen et al., *Acta Anatomica*, 161: 36-78 (1998).
Cantin et al., *Am. J. Respir. Cell Mol. Biol.*, 27(6): 659-665 (2002).
Cohn et al., *J. Biomed. Mater. Res,.* 22(11): 993-1009 (1988).
Copeland, "Enzymes: A Practical Introduction to Structure, Mechanism and Data Analysis" 2nd ed., Wiley-VCH, New York, p. 146-150 (2000).
Edge et al., *Anal. Biochem.*, 118(1): 131-137 (1981).
Felix et al., *J. Peptide Res.*, 63: 85-90 (2004).
Ge et al., *J. Biol. Chem.*, 272(34): 21357-21363 (1997).
Gervais et al., *Glycobiology*, 13(3): 179-189 (2003).
Grabenhorst et al., *J. Biol. Chem.*, 274(51): 36107-36116 (1999).
Gross et al., *Biochemistry*, 28(18): 7386-7392 (1989).

Harris et al., *Abstracts of Papers of the American Chemical Society*, 201(4), P 64-POLY, 154-155 (1991).
Harris (ed.), "Poly(Ethylene Glycol) Chemistry: Biotechnical and Biomedical Applications", Plenum Press, New York (1992).
Harris et al. (eds.), "Poly(ethylene glycol): Chemistry and Biological Applications," ACS Symposium Series, vol. 680, American Chemical Society (1997).
Hassan et al., *Carbohydrates in Chemistry and Biology*, Part II, 3: 273-292 (2000).
Herscovics et al., *FASEB J.*, 7(6): 540-550 (1993).
Kajihara et al., *Carbohydr. Res.*, 315(1-2): 137-141 (1999).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Keene et al., *J. Biol. Chem.*, 264(9): 4769-4775 (1989).
Keppler et al., *Glycobiol.*, 11(2): 11R-18R (2001).
Kobayashi et al., *Eur. J. Nucl. Med.*, 27(9):1334-1339 (2000).
Kornfeld et al., *Ann. Rev. Biochem.*, 54: 631-664 (1985).
Langer, *Science*, 249(4976): 1527-1533 (1990).
Legault et al., *J. Biol. Chem.*, 270(36): 20987-20996 (1995).
Lin et al., *Proc. Natl. Acad. Sci. USA*, 82: 7580-7584 (1985).
Meynial-Salles et al., *J. Biotechnol.*, 46(1): 1-14 (1996).
Min et al., *Endocr. J.*, 43(5): 585-593 (1996).
Muller et al., *J. Biol. Chem.*, 272(40): 24780-24793 (1997).
Muller et al., *J. Biol. Chem.*, 274(26): 18165-18172 (1999).
Rotondaro et al., *Mol. Biotech.*, 11: 117-128 (1999).
Rudikoff et al., *Proc. Natl. Acad. Sci. USA*, 79(6):1979-1983 (1982).
Sasaki et al., *J. Biol. Chem.*, 262(25): 12059-12076 (1987).
Sasaki et al., *J.Biol. Chem.*, 269: 14730-14737 (1994).
Seely et al., *J. Chromatog.*, 908: 235-241 (2001).
Seitz, *Chembiochem.*, 1(4): 214-246 (2000).
Shen et al., *Biochem. Biophys. Res. Commun.*, 102(3): 1048-1054 (1981).
Shinkai et al., *Prot. Exp. Purif.*, 10: 379-385 (1997).
Snider et al., *J. Chromatogr.*, A 599(1-2): 141-155 (1992).
Sojar et al., *Arch. Biochem. Biophys.*, 259(1): 52-57 (1987).
Srinivasachar et al., *Biochemistry*, 28(6): 2501-2509 (1989).
Stemmer, *Nature*, 370(6488): 389-391 (1994).
Stemmer, *Proc. Natl. Acad. Sci. USA*, 91(22): 10747-10751 (1994).
Strausberg et al., *Proc Natl Acad Sci USA*, 99(26): 16899-16903 (2002).
Taniguchi et al., *Proteomics*, 1(2): 239-247 (2001).
Tsunoda et al., *J. Pharmacol. Exp. Ther.*, 209(1): 368-372 (1999).
Urdal et al, *J. Chromatogr.*, 296: 171-179 (1984).
Vitetta et al., *Science*, 313: 308-309 (2006).
White et al., *J. Biol. Chem.*, 270(41): 24156-24165 (1995).
Witte et al., *J. Am. Chem. Soc.*, 119(9): 2114-2118 (1997).
Witte et al., *Cancer and Metastasis Rev.*, 17: 155-161 (1998).
Wu et al., *J. Drug Target.*, 10(3): 239-245 (2002).
Yamada et al., *Biochemistry*, 20(17): 4836-4842 (1981).
Younes et al., *J. Biomed. Mater. Res.*, 21(11): 1301-1316 (1987).
Zarling et al., *J. Immunol.*, 124(2): 913-920 (1980).

* cited by examiner

FIGURE 6

175 amino acid variant

MTPLGPASSLPQSFLLKCLEQVRKIQGDGAALQEKLCA
TYKLCHPEELVLLGHSLGIPWAPLSSCPSQALQLAGCLS
QLHSGLFLYQGLLQALEGISPELGPTLDTLQLDVADFAT
TIWQQMEELGMAPALQPTQGAMPAFASAFQRRAGGVL
VASHLQSFLEVSYRVLRHLAQP (SEQ ID NO: 1).

174 amino acid variant

TPLGPASSLPQSFLLKCLEQVRKIQGDGAALQEKLCATY
KLCHPEELVLLGHSLGIPWAPLSSCPSQALQLAGCLSQL
HSGLFLYQGLLQALEGISPELGPTLDTLQLDVADFATTI
WQQMEELGMAPALQPTQGAMPAFASAFQRRAGGVLV
ASHLQSFLEVSYRVLRHLAQP (SEQ ID NO: 2).

FIGURE 7A

| Protein | Organism | EC# | GenBank / GenPept | | SwissProt | PDB /3D |
|---|---|---|---|---|---|---|
| At1g08280 | Arabidopsis thaliana | n.d. | AC011438 BT004583 NC_003070 | AAF18241.1 AAO42829.1 NP_172305.1 | Q84W00 Q9SGD2 | |
| At1g08660/F22O13.14 | Arabidopsis thaliana | n.d. | AC003981 AY064135 AY124807 NC_003070 NM_180609 | AAF99778.1 AAL36042.1 AAM70516.1 NP_172342.1 NP_850940.1 | Q8VZJ0 Q9FRR9 | |
| At3g48820/T21J18_90 | Arabidopsis thaliana | n.d. | AY080589 AY133816 AL132963 NM_114741 | AAL85966.1 AAM91750.1 CAB87910.1 NP_190451.1 | Q8RY00 Q9M301 | |
| α-2,3-sialyltransferase (ST3GAL-IV) | Bos taurus | n.d. | AJ584673 | CAE48298.1 | | |
| α-2,3-sialyltransferase (St3Gal-V) | Bos taurus | n.d. | AJ585768 | CAE51392.1 | | |
| α-2,6-sialyltransferase (Siat7b) | Bos taurus | n.d. | AJ620651 | CAF05850.1 | | |
| α-2,8-sialyltransferase (SIAT8A) | Bos taurus | 2.4.99.8 | AJ699418 | CAG27880.1 | | |
| α-2,8-sialyltransferase (Siat8D) | Bos taurus | n.d. | AJ699421 | CAG27883.1 | | |
| α-2,8-sialyltransferase ST8Siα-III (Siat8C) | Bos taurus | n.d. | AJ704563 | CAG28696.1 | | |
| CMP α-2,6-sialyltransferase (ST6Gal I) | Bos taurus | 2.4.99.1 | Y15111 NM_177517 | CAA75385.1 NP_803483.1 | O18974 | |
| sialyltransferase 8 (fragment) | Bos taurus | n.d. | AF450088 | AAL47018.1 | Q8WN13 | |
| sialyltransferase ST3Gal-II (Siat4B) | Bos taurus | n.d. | AJ748841 | CAG44450.1 | | |
| sialyltransferase ST3Gal-III (Siat6) | Bos taurus | n.d. | AJ748842 | CAG44451.1 | | |
| sialyltransferase ST3Gal-VI (Siat10) | Bos taurus | n.d. | AJ748843 | CAG44452.1 | | |
| ST3Gal I | Bos taurus | n.d. | AJ305086 | CAC24698.1 | Q9BEG4 | |
| St6GalNAc-VI | Bos taurus | n.d. | AJ620949 | CAF06586.1 | | |
| CDS4 | Branchiostoma floridae | n.d. | AF391289 | AAM18873.1 | Q8T771 | |
| polysialyltransferase (PST) (fragment) ST8Sia IV | Cercopithecus aethiops | 2.4.99.- | AF210729 | AAF17105.1 | Q9TT09 | |
| polysialyltransferase (STX) (fragment) ST8Sia II | Cercopithecus aethiops | 2.4.99.- | AF210318 | AAF17104.1 | Q9TT10 | |
| α-2,3-sialyltransferase ST3Gal I (Siat4) | Ciona intestinalis | n.d. | AJ626815 | CAF25173.1 | | |
| α-2,3-sialyltransferase ST3Gal I (Siat4) | Ciona savignyi | n.d. | AJ626814 | CAF25172.1 | | |
| α-2,8-polysialyltransferase ST8Sia IV | Cricetulus griseus | 2.4.99.- | - Z46801 | AAE28634 CAA86822.1 | Q64690 | |
| Gal β-1,3/4-GlcNAc α-2,3-sialyltransferase St3Gal I | Cricetulus griseus | n.d. | AY266675 | AAP22942.1 | Q80WL0 | |
| Gal β-1,3/4-GlcNAc α-2,3-sialyltransferase St3Gal II (fragment) | Cricetulus griseus | n.d. | AY266676 | AAP22943.1 | Q80WK9 | |
| α-2,3-sialyltransferase ST3Gal I (Siat4) | Danio rerio | n.d. | AJ783740 | CAH04017.1 | | |
| α-2,3-sialyltransferase ST3Gal II (Siat5) | Danio rerio | n.d. | AJ783741 | CAH04018.1 | | |

FIGURE 7B

| Protein | Organism | EC# | GenBank / GenPept | | SwissProt | PDB /3D |
|---|---|---|---|---|---|---|
| α-2,3-sialyltransferase ST3Gal III (Siat6) | Danio rerio | n.d. | AJ626821 | CAF25179.1 | | |
| α-2,3-sialyltransferase ST3Gal IV (Siat4c) | Danio rerio | n.d. | AJ744809 | CAG32845.1 | | |
| α-2,3-sialyltransferase ST3Gal V-r (Siat5-related) | Danio rerio | n.d. | AJ783742 | CAH04019.1 | | |
| α-2,6-sialyltransferase ST6Gal I (Siat1) | Danio rerio | n.d. | AJ744801 | CAG32837.1 | | |
| α-2,6-sialyltransferase ST6GalNAc II (Siat7B) | Danio rerio | n.d. | AJ634459 | CAG25680.1 | | |
| α-2,6-sialyltransferase ST6GalNAc V (Siat7E) (fragment) | Danio rerio | n.d. | AJ646874 | CAG26703.1 | | |
| α-2,6-sialyltransferase ST6GalNAc VI (Siat7F) (fragment) | Danio rerio | n.d. | AJ646883 | CAG26712.1 | | |
| α-2,8-sialyltransferase ST8Sia I (Siat 8A) (fragment) | Danio rerio | n.d. | AJ715535 | CAG29374.1 | | |
| α-2,8-sialyltransferase ST8Sia III (Siat 8C) (fragment) | Danio rerio | n.d. | AJ715543 | CAG29382.1 | | |
| α-2,8-sialyltransferase ST8Sia IV (Siat 8D) (fragment) | Danio rerio | n.d. | AJ715545 | CAG29384.1 | | |
| α-2,8-sialyltransferase ST8Sia V (Siat 8E) (fragment) | Danio rerio | n.d. | AJ715546 | CAG29385.1 | | |
| α-2,8-sialyltransferase ST8Sia VI (Siat 8F) (fragment) | Danio rerio | n.d. | AJ715551 | CAG29390.1 | | |
| β-galactosamide α-2,6-sialyltransferase II (ST6Gal II) | Danio rerio | n.d. | AJ627627 | CAF29495.1 | | |
| N-glycan α-2,8-sialyltransferase | Danio rerio | n.d. | BC050483 AY055462 NM_153662 | AAH50483.1 AAL17875.1 NP_705948.1 | Q7ZU51 Q8QH83 | |
| ST3Gal III-related (siat6r) | Danio rerio | n.d. | BC053179 AJ626820 NM_200355 | AAH53179.1 CAF25178.1 NP_956649.1 | Q7T3B9 | |
| St3Gal-V | Danio rerio | n.d. | AJ619960 | CAF04061.1 | | |
| st6GalNAc-VI | Danio rerio | n.d. | BC060932 AJ620947 | AAH60932.1 CAF06584.1 | | |
| α-2,6-sialyltransferase (CG4871) ST6Gal I | Drosophila melanogaster | 2.4.99.1 | AE003465 AF218237 AF397532 AE003465 NM_079129 NM_166684 | AAF47256.1 AAG13185.1 AAK92126.1 AAM70791.1 NP_523853.1 NP_726474.1 | Q9GU23 Q9W121 | |
| α-2,3-sialyltransferase (ST3Gal-VI) | Gallus gallus | n.d. | AJ585767 AJ627204 | CAE51391.1 CAF25503.1 | | |
| α-2,3-sialyltransferase ST3Gal I | Gallus gallus | 2.4.99.4 | X80503 NM_205217 | CAA56666.1 NP_990548.1 | Q11200 | |
| α-2,3-sialyltransferase ST3Gal IV (fragment) | Gallus gallus | 2.4.99.- | AF035250 | AAC14163.1 | O73724 | |
| α-2,3-sialyltransferase (ST3GAL-II) | Gallus gallus | n.d. | AJ585761 | CAE51385.2 | | |
| α-2,6-sialyltransferase (Siat7b) | Gallus gallus | n.d. | AJ620653 | CAF05852.1 | | |
| α-2,6-sialyltransferase ST6Gal I | Gallus gallus | 2.4.99.1 | X75558 NM_205241 | CAA53235.1 NP_990572.1 | Q92182 | |
| α-2,6-sialyltransferase | Gallus gallus | 2.4.99.3 | - | AAE68028.1 | Q92183 | |

FIGURE 7C

| Protein | Organism | EC# | GenBank / GenPept | | SwissProt | PDB /3D |
|---|---|---|---|---|---|---|
| ST6GalNAc I | | | X74946<br>NM_205240 | AAE68029.1<br>CAA52902.1<br>NP_990571.1 | | |
| α-2,6-sialyltransferase ST6GalNAc II | Gallus gallus | 2.4.99.- | X77775<br>NM_205233 | AAE68030.1<br>CAA54813.1<br>NP_990564.1 | Q92184 | |
| α-2,6-sialyltransferase ST6GalNAc III (SIAT7C) (fragment) | Gallus gallus | n.d. | AJ634455 | CAG25677.1 | | |
| α-2,6-sialyltransferase ST6GalNAc V (SIAT7E) (fragment) | Gallus gallus | n.d. | AJ646877 | CAG26706.1 | | |
| α-2,8-sialyltransferase (GD3 Synthase) ST8Sia I | Gallus gallus | 2.4.99.- | U73176 | AAC28888.1 | P79783 | |
| α-2,8-sialyltransferase (SIAT8B) | Gallus gallus | n.d. | AJ699419 | CAG27881.1 | | |
| α-2,8-sialyltransferase (SIAT8C) | Gallus gallus | n.d. | AJ699420 | CAG27882.1 | | |
| α-2,8-sialyltransferase (SIAT8F) | Gallus gallus | n.d. | AJ699424 | CAG27886.1 | | |
| α-2,8-syalyltransferase ST8Siα-V (SIAT8C) | Gallus gallus | n.d. | AJ704564 | CAG28697.1 | | |
| β-galactosamide α-2,6-sialyltransferase II (ST6Gal II) | Gallus gallus | n.d. | AJ627629 | CAF29497.1 | | |
| GM3 synthase (SIAT9) | Gallus gallus | 2.4.99.9 | AY515255 | AAS83519.1 | | |
| polysialyltransferase ST8Sia IV | Gallus gallus | 2.4.99.- | AF008194 | AAB95120.1 | O42399 | |
| α-2,3-sialyltransferase ST3Gal I | Homo sapiens | 2.4.99.4 | L29555<br>AF059321<br>L13972<br>AF155238<br>AF186191<br>BC018357<br>NM_003033<br>NM_173344 | AAA36612.1<br>AAC17874.1<br>AAC37574.1<br>AAD39238.1<br>AAG29876.1<br>AAH18357.1<br>NP_003024.1<br>NP_775479.1 | Q11201<br>O60677<br>Q9UN51 | |
| α-2,3-sialyltransferase ST3Gal II | Homo sapiens | 2.4.99.4 | U63090<br>BC036777<br>X96667<br>NM_006927 | AAB40389.1<br>AAH36777.1<br>CAA65447.1<br>NP_008858.1 | Q16842<br>O00654 | |
| α-2,3-sialyltransferase ST3Gal III (SiaT6) | Homo sapiens | 2.4.99.6 | L23768<br>BC050380<br>AF425851<br>AF425852<br>AF425853<br>AF425854<br>AF425855<br>AF425856<br>AF425857<br>AF425858<br>AF425859<br>AF425860<br>AF425861<br>AF425862<br>AF425863<br>AF425864<br>AF425865<br>AF425866<br>AF425867<br>AY167992<br>AY167993<br>AY167994 | AAA35778.1<br>AAH50380.1<br>AAO13859.1<br>AAO13860.1<br>AAO13861.1<br>AAO13862.1<br>AAO13863.1<br>AAO13864.1<br>AAO13865.1<br>AAO13866.1<br>AAO13867.1<br>AAO13868.1<br>AAO13869.1<br>AAO13870.1<br>AAO13871.1<br>AAO13872.1<br>AAO13873.1<br>AAO13874.1<br>AAO13875.1<br>AAO38806.1<br>AAO38807.1<br>AAO38808.1 | Q11203<br>Q86UR6<br>Q86UR7<br>Q86UR8<br>Q86UR9<br>Q86US0<br>Q86US1<br>Q86US2<br>Q8IX43<br>Q8IX44<br>Q8IX45<br>Q8IX46<br>Q8IX47<br>Q8IX48<br>Q8IX49<br>Q8IX50<br>Q8IX51<br>Q8IX52<br>Q8IX53<br>Q8IX54<br>Q8IX55<br>Q8IX56 | |

FIGURE 7D

| Protein | Organism | EC# | GenBank / GenPept | | SwissProt | PDB /3D |
|---|---|---|---|---|---|---|
| | | | AY167995 | AAO38809.1 | Q8IX57 | |
| | | | AY167996 | AAO38810.1 | Q8IX58 | |
| | | | AY167997 | AAO38811.1 | | |
| | | | AY167998 | AAO38812.1 | | |
| | | | NM_006279 | NP_006270.1 | | |
| | | | NM_174964 | NP_777624.1 | | |
| | | | NM_174965 | NP_777625.1 | | |
| | | | NM_174966 | NP_777626.1 | | |
| | | | NM_174967 | NP_777627.1 | | |
| | | | NM_174969 | NP_777629.1 | | |
| | | | NM_174970 | NP_777630.1 | | |
| | | | NM_174972 | NP_777632.1 | | |
| α-2,3-sialyltransferase ST3Gal IV | Homo sapiens | 2.4.99.- | L23767 | AAA16460.1 | Q11206 | |
| | | | AF035249 | AAC14162.1 | O60497 | |
| | | | BC010645 | AAH10645.1 | Q96QQ9 | |
| | | | AY040826 | AAK93790.1 | Q8N6A6 | |
| | | | AF516602 | AAM66431.1 | Q8N6A7 | |
| | | | AF516603 | AAM66432.1 | Q8NFD3 | |
| | | | AF516604 | AAM66433.1 | Q8NFG7 | |
| | | | AF525084 | AAM81378.1 | | |
| | | | X74570 | CAA52662.1 | | |
| | | | CR456858 | CAG33139.1 | | |
| | | | NM_006278 | NP_006269.1 | | |
| α-2,3-sialyltransferase ST3Gal VI | Homo sapiens | 2.4.99.4 | AF119391 | AAD39131.1 | Q9Y274 | |
| | | | BC023312 | AAH23312.1 | | |
| | | | AB022918 | BAA77609.1 | | |
| | | | AX877828 | CAE89895.1 | | |
| | | | AX886023 | CAF00161.1 | | |
| | | | NM_006100 | NP_006091.1 | | |
| α-2,6-sialyltransferase (ST6Gal II ; KIAA1877) | Homo sapiens | n.d. | BC008680 | AAH08680.1 | Q86Y44 | |
| | | | AB058780 | BAB47506.1 | Q8IUG7 | |
| | | | AB059555 | BAC24793.1 | Q96HE4 | |
| | | | AJ512141 | CAD54408.1 | Q96JF0 | |
| | | | AX795193 | CAE48260.1 | | |
| | | | AX795193 | CAE48261.1 | | |
| | | | NM_032528 | NP_115917.1 | | |
| α-2,6-sialyltransferase (ST6GALNAC III) | Homo sapiens | n.d. | BC059363 | AAH59363.1 | Q8N259 | |
| | | | AY358540 | AAQ88904.1 | Q8NDV1 | |
| | | | AK091215 | BAC03611.1 | | |
| | | | AJ507291 | CAD45371.1 | | |
| | | | NM_152996 | NP_694541.1 | | |
| α-2,6-sialyltransferase (ST6GalNAc V) | Homo sapiens | n.d. | BC001201 | AAH01201.1 | Q9BVH7 | |
| | | | AK056241 | BAB71127.1 | | |
| | | | AL035409 | CAB72344.1 | | |
| | | | AJ507292 | CAD45372.1 | | |
| | | | NM_030965 | NP_112227.1 | | |
| α-2,6-sialyltransferase (SThM) ST6GalNAc II | Homo sapiens | 2.4.99.- | U14550 | AAA52228.1 | Q9UJ37 | |
| | | | BC040455 | AAH40455.1 | Q12971 | |
| | | | AJ251053 | CAB61434.1 | | |
| | | | NM_006456 | NP_006447.1 | | |
| α-2,6-sialyltransferase ST6Gal I | Homo sapiens | 2.4.99.1 | BC031476 | AAH31476.1 | P15907 | |
| | | | BC040009 | AAH40009.1 | | |
| | | | A17362 | CAA01327.1 | | |
| | | | A23699 | CAA01686.1 | | |
| | | | X17247 | CAA35111.1 | | |
| | | | X54363 | CAA38246.1 | | |
| | | | X62822 | CAA44634.1 | | |
| | | | NM_003032 | NP_003023.1 | | |
| | | | NM_173216 | NP_775323.1 | | |
| α-2,6-sialyltransferase ST6GalNAc I | Homo sapiens | 2.4.99.3 | BC022462 | AAH22462.1 | Q8TBJ6 | |
| | | | AY096001 | AAM22800.1 | Q9NSC7 | |
| | | | AY358918 | AAQ89277.1 | Q9NXQ7 | |
| | | | AK000113 | BAA90953.1 | | |
| | | | Y11339 | CAA72179.2 | | |

FIGURE 7E

| Protein | Organism | EC# | GenBank / GenPept | | SwissProt | PDB /3D |
|---|---|---|---|---|---|---|
| | | | NM_018414 | NP_060884.1 | | |
| α-2,8-polysialyltransferase ST8Sia IV | Homo sapiens | 2.4.99.- | L41680<br>BC027866<br>BC053657<br>NM_005668 | AAC41775.1<br>AAH27866.1<br>AAH53657.1<br>NP_005659.1 | Q8N1F4<br>Q92187<br>Q92693 | |
| α-2,8-sialyltransferase (GD3 synthase) ST8Sia I | Homo sapiens | 2.4.99.8 | L32867<br>L43494<br>BC046158<br>-<br>AY569975<br>D26360<br>X77922<br>NM_003034 | AAA62366.1<br>AAC37586.1<br>AAH46158.1<br>AAQ53140.1<br>AAS75783.1<br>BAA05391.1<br>CAA54891.1<br>NP_003025.1 | Q86X71<br>Q92185<br>Q93064 | |
| α-2,8-sialyltransferase ST8Sia II | Homo sapiens | 2.4.99.- | L29556<br>U82762<br>U33551<br>BC069584<br>NM_006011 | AAA36613.1<br>AAB51242.1<br>AAC24458.1<br>AAH69584.1<br>NP_006002.1 | Q92186<br>Q92470<br>Q92746 | |
| α-2,8-sialyltransferase ST8Sia III | Homo sapiens | 2.4.99.- | AF004668<br>AF003092<br>NM_015879 | AAB87642.1<br>AAC15901.2<br>NP_056963.1 | O43173<br>Q9NS41 | |
| α-2,8-sialyltransferase ST8Sia V | Homo sapiens | 2.4.99.- | U91641<br>CR457037<br>NM_013305 | AAC51727.1<br>CAG33318.1<br>NP_037437.1 | O15466 | |
| ENSP00000020221 (fragment) | | n.d. | AC023295 | | | |
| lactosylceramide α-2,3-sialyltransferase (ST3Gal V) | Homo sapiens | 2.4.99.9 | AF105026<br>AF119415<br>BC065936<br>AY152815<br>AAP65066<br>AY359105<br>AB018356<br>AX876536<br>NM_003896 | AAD14634.1<br>AAF66146.1<br>AAH65936.1<br>AAO16866.1<br>AAP65066.1<br>AAQ89463.1<br>BAA33950.1<br>CAE89320.1<br>NP_003887.2 | Q9UNP4<br>O94902 | |
| N-acetylgalactosaminide α-2,6-sialyltransferase (ST6GalNAc VI) | Homo sapiens | 2.4.99.- | BC006564<br>BC007802<br>BC016299<br>AY358672<br>AB035173<br>AK023900<br>AJ507293<br>AX880950<br>CR457318<br>NM_013443 | AAH06564.1<br>AAH07802.1<br>AAH16299.1<br>AAQ89035.1<br>BAA87035.1<br>BAB14715.1<br>CAD45373.1<br>CAE91145.1<br>CAG33599.1<br>NP_038471.2 | Q969X2<br>Q9H8A2<br>Q9ULB8 | |
| N-acetylgalactosaminide α-2,6-sialyltransferase IV (ST6GalNAc IV) | Homo sapiens | 2.4.99.- | AF127142<br>BC036705<br>-<br>AB035172<br>AK000600<br>Y17461<br>AJ271734<br>AX061620<br>AX068265<br>AX969252<br>NM_014403<br>NM_175039 | AAF00102.1<br>AAH36705.1<br>AAP63349.1<br>BAA87034.1<br>BAA91281.1<br>CAB44354.1<br>CAC07404.1<br>CAC24981.1<br>CAC27250.1<br>CAF14360.1<br>NP_055218.3<br>NP_778204.1 | Q9H4F1<br>Q9NWU6<br>Q9UKU1<br>Q9ULB9<br>Q9Y3G3<br>Q9Y3G4 | |
| ST8SIA-VI (fragment) | Homo sapiens | n.d. | AJ621583<br>XM_291725 | CAF21722.1<br>XP_291725.2 | | |
| unnamed protein product | Homo sapiens | n.d. | AK021929<br>AX881696 | BAB13940.1<br>CAE91353.1 | Q9HAA9 | |
| Gal β-1,3/4-GlcNAc α- | Mesocricetus | 2.4.99.6 | AJ245699 | CAB53394.1 | Q9QXF6 | |

FIGURE 7F

| Protein | Organism | EC# | GenBank / GenPept | | SwissProt | PDB /3D |
|---|---|---|---|---|---|---|
| 2,3-sialyltransferase (ST3Gal III) | auratus | | | | | |
| Galβ1,3/4-GlcNAc α-2,3-sialyltransferase (ST3Gal IV) | Mesocricetus auratus | 2.4.99.6 | AJ245700 | CAB53395.1 | Q9QXF5 | |
| GD3 synthase (fragment) ST8Sia I | Mesocricetus auratus | n.d. | AF141657 | AAD33879.1 | Q9WUL1 | |
| polysialyltransferase (ST8Sia IV) | Mesocricetus auratus | 2.4.99.- | AJ245701 | CAB53396.1 | Q9QXF4 | |
| α-2,3-sialyltransferase ST3Gal I | St3gal1 | Mus musculus | 2.4.99.4 | AF214028<br>AK031344<br>AK078469<br>X73523<br>NM_009177 | AAF60973.1<br>BAC27356.1<br>BAC37290.1<br>CAA51919.1<br>NP_033203.1 | P54751<br>Q11202<br>Q9JL30 |
| α-2,3-sialyltransferase ST3Gal II | St3gal2 | Mus musculus | 2.4.99.4 | BC015264<br>BC066064<br>AK034554<br>AK034863<br>AK053827<br>X76989<br>NM_009179<br>NM_178048 | AAH15264.1<br>AAH66064.1<br>BAC28752.1<br>BAC28859.1<br>BAC35543.1<br>CAA54294.1<br>NP_033205.1<br>NP_835149.1 | Q11204<br>Q8BPL0<br>Q8BSA0<br>Q8BSE9<br>Q91WH6 |
| α-2,3-sialyltransferase ST3Gal III | St3gal3 | Mus musculus | 2.4.99.- | BC006710<br>AK005053<br>AK013016<br>X84234<br>NM_009176 | AAH06710.1<br>BAB23779.1<br>BAB28598.1<br>CAA59013.1<br>NP_033202.2 | P97325<br>Q922X5<br>Q9CZ48<br>Q9DBB6 |
| α-2,3-sialyltransferase ST3Gal IV | St3gal4 | Mus musculus | 2.4.99.4 | BC011121<br>BC050773<br>D28941<br>AK008543<br>AB061305<br>X95809<br>NM_009178 | AAH11121.1<br>AAH50773.1<br>BAA06068.1<br>BAB25732.1<br>BAB47508.1<br>CAA65076.1<br>NP_033204.2 | P97354<br>Q61325<br>Q91Y74<br>Q921R5<br>Q9CVE8 |
| α-2,3-sialyltransferase ST3Gal VI | St3gal6 | Mus musculus | 2.4.99.4 | AF119390<br>BC052338<br>AB063326<br>AK033562<br>AK041173<br>NM_018784 | AAD39130.1<br>AAH52338.1<br>BAB79494.1<br>BAC28360.1<br>BAC30851.1<br>NP_061254 | Q80UR7<br>Q8BLV1<br>Q8VIB3<br>Q9WVG2 |
| α-2,6-sialyltransferase ST6GalNAc II | St6galnac2 | Mus musculus | 2.4.99.- | NM_009180<br>BC010208<br>AB027198<br>AK004613<br>X93999<br>X94000<br>NM_009180 | 6677963<br>AAH10208.1<br>BAB00637.1<br>BAB23410.1<br>CAA63821.1<br>CAA63822.1<br>NP_033206.2 | P70277<br>Q9DC24<br>Q9JJM5 |
| α-2,6-sialyltransferase ST6Gal I | St6gal1 | Mus musculus | 2.4.99.1 | -<br>BC027833<br>D16106<br>AK034768<br>AK084124<br>NM_145933 | AAE68031.1<br>AAH27833.1<br>BAA03680.1<br>BAC28828.1<br>BAC39120.1<br>NP_666045.1 | Q64685<br>Q8BM62<br>Q8K1L1 |
| α-2,6-sialyltransferase ST6Gal II | St6gal2 | Mus musculus | n.d. | AK082566<br>AB095093<br>AK129462<br>NM_172829 | BAC38534.1<br>BAC87752.1<br>BAC98272.1<br>NP_766417.1 | Q8BUU4 |
| α-2,6-sialyltransferase ST6GalNAc I | St6galnac1 | Mus musculus | 2.4.99.3 | Y11274<br>NM_011371 | CAA72137.1<br>NP_035501.1 | Q9QZ39<br>Q9JJP5 |
| α-2,6-sialyltransferase ST6GalNAc III | St6galnac3 | Mus musculus | n.d. | BC058387<br>AK034804<br>Y11342<br>Y11343 | AAH58387.1<br>BAC28836.1<br>CAA72181.2<br>CAB95031.1 | Q9WUV2<br>Q9JHP5 |

FIGURE 7G

| Protein | Organism | EC# | GenBank / GenPept | | SwissProt | PDB /3D |
|---|---|---|---|---|---|---|
| | | | NM_011372 | NP_035502 | | |
| α-2,6-sialyltransferase ST6GalNAc IV | St6galnac4 | Mus musculus | 2.4.99.7 | BC056451 AK085730 AJ007310 Y15779 Y15780 Y19055 Y19057 NM_011373 | AAH56451.1 BAC39523.1 CAA07446.1 CAB43507.1 CAB43514.1 CAB93946.1 CAB93948.1 NP_035503.1 | Q8C3J2 Q9JHP2 Q9R2B6 O88725 Q9JHP0 Q9QUP9 Q9R2B5 |
| α-2,8-sialyltransferase (GD3 synthase) ST8Sia I | St8sia1 | Mus musculus | 2.4.99.8 | L38677 BC024821 AK046188 AK052444 X84235 AJ401102 NM_011374 | AAA91869.1 AAH24821.1 BAC32625.1 BAC34994.1 CAA59014.1 CAC20706.1 NP_035504.1 | Q64468 Q64687 Q8BL76 Q8BWI0 Q8K1C1 Q9EPK0 |
| α-2,8-sialyltransferase (ST8Sia VI) | St8sia6 | Mus musculus | n.d. | AB059554 AK085105 NM_145838 | BAC01265.1 BAC39367.1 NP_665837.1 | Q8BI43 Q8K4T1 |
| α-2,8-sialyltransferase ST8Sia II | St8sia2 | Mus musculus | 2.4.99.- | X83562 X99646 X99647 X99648 X99649 X99650 X99651 NM_009181 | CAA58548.1 CAA67965.1 CAA67965.1 CAA67965.1 CAA67965.1 CAA67965.1 CAA67965.1 NP_033207.1 | O35696 |
| α-2,8-sialyltransferase ST8Sia IV | St8sia4 | Mus musculus | 2.4.99.8 | BC060112 AK003690 AK041723 AJ223956 X86000 Y09484 NM_009183 | AAH60112.1 BAB22941.1 BAC31044.1 CAA11685.1 CAA59992.1 CAA70692.1 NP_033209.1 | Q64692 Q8BY70 |
| α-2,8-sialyltransferase ST8Sia V | St8sia5 | Mus musculus | 2.4.99.- | BC034855 AK078670 X98014 X98014 X98014 NM_013666 NM_153124 NM_177416 | AAH34855.1 BAC37354.1 CAA66642.1 CAA66643.1 CAA66644.1 NP_038694.1 NP_694764.1 NP_803135.1 | P70126 P70127 P70128 Q8BJW0 Q8JZQ3 |
| α-2,8-sialytransferase ST8Sia III | St8sia3 | Mus musculus | 2.4.99.- | BC075645 AK015874 X80502 NM_009182 | AAH75645.1 BAB30012.1 CAA56665.1 NP_033208.1 | Q64689 Q9CUJ6 |
| GD1 synthase (ST6GalNAc V) | St6galnac5 | Mus musculus | n.d. | BC055737 AB030836 AB028840 AK034387 AK038434 AK042683 NM_012028 | AAH55737.1 BAA85747.1 BAA89292.1 BAC28693.1 BAC29997.1 BAC31331.1 NP_036158.2 | Q8CAM7 Q8CBX1 Q9QYJ1 Q9R0K6 |
| GM3 synthase (α-2,3-sialyltransferase) ST3Gal V | St3gal5 | Mus musculus | 2.4.99.9 | AF119416 - AB018048 AB013302 AK012961 Y15003 NM_011375 | AAF66147.1 AAP65063.1 BAA33491.1 BAA76467.1 BAB28571.1 CAA75235.1 NP_035505.1 | O88829 Q9CZ65 Q9QWF9 |
| N-acetylgalactosaminide α-2,6-sialyltransferase (ST6GalNAc VI) | St6galnac6 | Mus musculus | 2.4.99.- | BC036985 AB035174 AB035123 AK030648 | AAH36985.1 BAA87036.1 BAA95940.1 BAC27064.1 | Q8CDC3 Q8JZW3 Q9JM95 Q9R0G9 |

FIGURE 7H

| Protein | Organism | EC# | GenBank / GenPept | | SwissProt | PDB /3D |
|---|---|---|---|---|---|---|
| | | | NM_016973 | NP_058669.1 | | |
| M138L | Myxoma virus | n.d. | U46578 AF170726 NC_001132 | AAD00069.1 AAE61323.1 AAE61326.1 AAF15026.1 NP_051852.1 | | |
| α-2,3-sialyltransferase (St3Gal-I) | Oncorhynchus mykiss | n.d. | AJ585760 | CAE51384.1 | | |
| α-2,6-sialyltransferase (Siat1) | Oncorhynchus mykiss | n.d. | AJ620649 | CAF05848.1 | | |
| α-2,8-polysialyltransferase IV (ST8Sia IV) | Oncorhynchus mykiss | n.d. | AB094402 | BAC77411.1 | Q7T2X5 | |
| GalNAc α-2,6-sialyltransferase (RtST6GalNAc) | Oncorhynchus mykiss | n.d. | AB097943 | BAC77520.1 | Q7T2X4 | |
| α-2,3-sialyltransferase ST3Gal IV | Oryctolagus cuniculus | 2.4.99.- | AF121967 | AAF28871.1 | Q9N257 | |
| OJ1217_F02.7 | Oryza sativa (japonica cultivar-group) | n.d. | AP004084 | BAD07616.1 | | |
| OSJNBa0043L24.2 or OSJNBb0002J11.9 | Oryza sativa (japonica cultivar-group) | n.d. | AL731626 AL662969 | CAD41185.1 CAE04714.1 | | |
| P0683f02.18 or P0489B03.1 | Oryza sativa (japonica cultivar-group) | n.d. | AP003289 AP003794 | BAB63715.1 BAB90552.1 | | |
| α-2,6-sialyltransferase ST6GalNAc V (Siat7E) (fragment) | Oryzias latipes | n.d. | AJ646876 | CAG26705.1 | | |
| α-2,3-sialyltransferase ST3Gal I (Siat4) | Pan troglodytes | n.d. | AJ744803 | CAG32839.1 | | |
| α-2,3-sialyltransferase ST3Gal II (Siat5) | Pan troglodytes | n.d. | AJ744804 | CAG32840.1 | | |
| α-2,3-sialyltransferase ST3Gal III (Siat6) | Pan troglodytes | n.d. | AJ626819 | CAF25177.1 | | |
| α-2,3-sialyltransferase ST3Gal IV (Siat4c) | Pan troglodytes | n.d. | AJ626824 | CAF25182.1 | | |
| α-2,3-sialyltransferase ST3Gal VI (Siat10) | Pan troglodytes | n.d. | AJ744808 | CAG32844.1 | | |
| α-2,6-sialyltransferase (Sia7A) | Pan troglodytes | n.d. | AJ748740 | CAG38615.1 | | |
| α-2,6-sialyltransferase (Sia7B) | Pan troglodytes | n.d. | AJ748741 | CAG38616.1 | | |
| α-2,6-sialyltransferase ST6GalNAc III (Siat7C) | Pan troglodytes | n.d. | AJ634454 | CAG25676.1 | | |
| α-2,6-sialyltransferase ST6GalNAc IV (Siat7D) (fragment) | Pan troglodytes | n.d. | AJ646870 | CAG26699.1 | | |
| α-2,6-sialyltransferase ST6GalNAc V (Siat7E) | Pan troglodytes | n.d. | AJ646875 | CAG26704.1 | | |
| α-2,6-sialyltransferase ST6GalNAc VI (Siat7F) (fragment) | Pan troglodytes | n.d. | AJ646882 | CAG26711.1 | | |
| α-2,8-sialyltransferase 8A (Siat8A) | Pan troglodytes | 2.4.99.8 | AJ697658 | CAG26896.1 | | |
| α-2,8-sialyltransferase 8B (Siat8B) | Pan troglodytes | n.d. | AJ697659 | CAG26897.1 | | |
| α-2,8-sialyltransferase 8C (Siat8C) | Pan troglodytes | n.d. | AJ697660 | CAG26898.1 | | |
| α-2,8-sialyltransferase 8D (Siat8D) | Pan troglodytes | n.d. | AJ697661 | CAG26899.1 | | |
| α-2,8-sialyltransferase | Pan troglodytes | n.d. | AJ697662 | CAG26900.1 | | |

FIGURE 7I

| Protein | Organism | EC# | GenBank / GenPept | | SwissProt | PDB /3D |
|---|---|---|---|---|---|---|
| 8E (Siat8E) | | | | | | |
| α-2,8-sialyltransferase 8F (Siat8F) | Pan troglodytes | n.d. | AJ697663 | CAG26901.1 | | |
| β-galactosamide α-2,6-sialyltransferase I (ST6Gal I; Siat1) | Pan troglodytes | 2.4.99.1 | AJ627624 | CAF29492.1 | | |
| β-galactosamide α-2,6-sialyltransferase II (ST6Gal II) | Pan troglodytes | n.d. | AJ627625 | CAF29493.1 | | |
| GM3 synthase ST3Gal V (Siat9) | Pan troglodytes | n.d. | AJ744807 | CAG32843.1 | | |
| S138L | Rabbit fibroma virus Kasza | n.d. | NC_001266 | NP_052025 | | |
| α-2,3-sialyltransferase ST3Gal III | Rattus norvegicus | 2.4.99.6 | M97754 NM_031697 | AAA42146.1 NP_113885.1 | Q02734 | |
| α-2,3-sialyltransferase ST3Gal IV (Siat4c) | Rattus norvegicus | n.d. | AJ626825 | CAF25183.1 | | |
| α-2,3-sialyltransferase ST3Gal VI | Rattus norvegicus | n.d. | AJ626743 | CAF25053.1 | | |
| α-2,6-sialyltransferase ST3Gal II | Rattus norvegicus | 2.4.99.- | X76988 NM_031695 | CAA54293.1 NP_113883.1 | Q11205 | |
| α-2,6-sialyltransferase ST6Gal I | Rattus norvegicus | 2.4.99.1 | M18769 M83143 | AAA41196.1 AAB07233.1 | P13721 | |
| α-2,6-sialyltransferase ST6GalNAc I (Siat7A) | Rattus norvegicus | n.d. | AJ634458 | CAG25684.1 | | |
| α-2,6-sialyltransferase ST6GalNAc II (Siat7B) | Rattus norvegicus | n.d. | AJ634457 | CAG25679.1 | | |
| α-2,6-sialyltransferase ST6GalNAc III | Rattus norvegicus | 2.4.99.- | L29554 BC072501 NM_019123 | AAC42086.1 AAH72501.1 NP_061996.1 | Q64686 | |
| α-2,6-sialyltransferase ST6GalNAc IV (Siat7D) (fragment) | Rattus norvegicus | n.d. | AJ646871 | CAG26700.1 | | |
| α-2,6-sialyltransferase ST6GalNAc V (Siat7E) | Rattus norvegicus | n.d. | AJ646872 | CAG26701.1 | | |
| α-2,6-sialyltransferase ST6GalNAc VI (Siat7F) (fragment) | Rattus norvegicus | n.d. | AJ646881 | CAG26710.1 | | |
| α-2,8-sialyltransferase (GD3 synthase) ST8Sia I | Rattus norvegicus | 2.4.99.- | U53883 D45255 | AAC27541.1 BAA08213.1 | P70554 P97713 | |
| α-2,8-sialyltransferase (SIAT8E) | Rattus norvegicus | n.d. | AJ699422 | CAG27884.1 | | |
| α-2,8-sialyltransferase (SIAT8F) | Rattus norvegicus | n.d. | AJ699423 | CAG27885.1 | | |
| α-2,8-sialyltransferase ST8Sia II | Rattus norvegicus | 2.4.99.- | L13445 NM_057156 | AAA42147.1 NP_476497.1 | Q07977 Q64688 | |
| α-2,8-sialyltransferase ST8Sia III | Rattus norvegicus | 2.4.99.- | U55938 NM_013029 | AAB50061.1 NP_037161.1 | P97877 | |
| α-2,8-sialyltransferase ST8Sia IV | Rattus norvegicus | 2.4.99.- | U90215 | AAB49989.1 | O08563 | |
| β-galactosamide α-2,6-sialyltransferase II (ST6Gal II) | Rattus norvegicus | n.d. | AJ627626 | CAF29494.1 | | |
| GM3 synthase ST3Gal V | Rattus norvegicus | n.d. | AB018049 NM_031337 | BAA33492.1 NP_112627.1 | O88830 | |

FIGURE 7J

| Protein | Organism | EC# | GenBank / GenPept | | SwissProt | PDB /3D |
|---|---|---|---|---|---|---|
| sialyltransferase ST3Gal-I (Siat4A) | Rattus norvegicus | n.d. | AJ748840 | CAG44449.1 | | |
| α-2,3-sialyltransferase (St3Gal-II) | Silurana tropicalis | n.d. | AJ585763 | CAE51387.1 | | |
| α-2,6-sialyltransferase (Siat7b) | Silurana tropicalis | n.d. | AJ620650 | CAF05849.1 | | |
| α-2,6-sialyltransferase (St6galnac) | Strongylocentrotus purpuratus | n.d. | AJ699425 | CAG27887.1 | | |
| α-2,3-sialyltransferase (ST3GAL-III) | Sus scrofa | n.d. | AJ585765 | CAE51389.1 | | |
| α-2,3-sialyltransferase (ST3GAL-IV) | Sus scrofa | n.d. | AJ584674 | CAE48299.1 | | |
| α-2,3-sialyltransferase ST3Gal I | Sus scrofa | 2.4.99.4 | M97753 | AAA31125.1 | Q02745 | |
| α-2,6-sialyltransferase (fragment) ST6Gal I | Sus scrofa | 2.4.99.1 | AF136746 | AAD33059.1 | Q9XSG8 | |
| β-galactosamide α-2,6-sialyltransferase (ST6GalNAc-V) | Sus scrofa | n.d. | AJ620948 | CAF06585.2 | | |
| sialyltransferase (fragment) ST6Gal I | sus scrofa | n.d. | AF041031 | AAC15633.1 | O62717 | |
| ST6GALNAC-V | Sus scrofa | n.d. | AJ620948 | CAF06585.1 | | |
| α-2,3-sialyltransferase (Siat5-r) | Takifugu rubripes | n.d. | AJ744805 | CAG32841.1 | | |
| α-2,3-sialyltransferase ST3Gal I (Siat4) | Takifugu rubripes | n.d. | AJ626816 | CAF25174.1 | | |
| α-2,3-sialyltransferase ST3Gal II (Siat5) (fragment) | Takifugu rubripes | n.d. | AJ626817 | CAF25175.1 | | |
| α-2,3-sialyltransferase ST3Gal III (Siat6) | Takifugu rubripes | n.d. | AJ626818 | CAF25176.1 | | |
| α-2,6-sialyltransferase ST6Gal I (Siat1) | Takifugu rubripes | n.d. | AJ744800 | CAG32836.1 | | |
| α-2,6-sialyltransferase ST6GalNAc II (Siat7B) | Takifugu rubripes | n.d. | AJ634460 | CAG25681.1 | | |
| α-2,6-sialyltransferase ST6GalNAc II B (Siat7B-related) | Takifugu rubripes | n.d. | AJ634461 | CAG25682.1 | | |
| α-2,6-sialyltransferase ST6GalNAc III (Siat7C) (fragment) | Takifugu rubripes | n.d. | AJ634456 | CAG25678.1 | | |
| α-2,6-sialyltransferase ST6GalNAc IV (siat7D) (fragment) | Takifugu rubripes | 2.4.99.3 | Y17466 AJ646869 | CAB44338.1 CAG26698.1 | Q9W6U6 | |
| α-2,6-sialyltransferase ST6GalNAc V (Siat7E) (fragment) | Takifugu rubripes | n.d. | AJ646873 | CAG26702.1 | | |
| α-2,6-sialyltransferase ST6GalNAc VI (Siat7F) (fragment) | Takifugu rubripes | n.d. | AJ646880 | CAG26709.1 | | |
| α-2,8-sialyltransferase ST8Sia I (Siat 8A) (fragment) | Takifugu rubripes | n.d. | AJ715534 | CAG29373.1 | | |
| α-2,8-sialyltransferase ST8Sia II (Siat 8B) (fragment) | Takifugu rubripes | n.d. | AJ715538 | CAG29377.1 | | |
| α-2,8-sialyltransferase ST8Sia III (Siat 8C) (fragment) | Takifugu rubripes | n.d. | AJ715541 | CAG29380.1 | | |
| α-2,8-sialyltransferase ST8Sia IIIr (Siat 8Cr) | Takifugu rubripes | n.d. | AJ715542 | CAG29381.1 | | |
| α-2,8-sialyltransferase ST8Sia V (Siat 8E) | Takifugu rubripes | n.d. | AJ715547 | CAG29386.1 | | |

FIGURE 7K

| Protein | Organism | EC# | GenBank / GenPept | | SwissProt | PDB /3D |
|---|---|---|---|---|---|---|
| α-2,8-sialyltransferase ST8Sia VI (Siat 8F) (fragment) | Takifugu rubripes | n.d. | AJ715549 | CAG29388.1 | | |
| α-2,8-sialyltransferase ST8Sia VIr (Siat 8Fr) | Takifugu rubripes | n.d. | AJ715550 | CAG29389.1 | | |
| α-2,3-sialyltransferase (Siat5-r) | Tetraodon nigroviridis | n.d. | AJ744806 | CAG32842.1 | | |
| α-2,3-sialyltransferase ST3Gal I (Siat4) | Tetraodon nigroviridis | n.d. | AJ744802 | CAG32838.1 | | |
| α-2,3-sialyltransferase ST3Gal III (Siat6) | Tetraodon nigroviridis | n.d. | AJ626822 | CAF25180.1 | | |
| α-2,6-sialyltransferase ST6GalNAc II (Siat7B) | Tetraodon nigroviridis | n.d. | AJ634462 | CAG25683.1 | | |
| α-2,6-sialyltransferase ST6GalNAc V (Siat7E) (fragment) | Tetraodon nigroviridis | n.d. | AJ646879 | CAG26708.1 | | |
| α-2,8-sialyltransferase ST8Sia I (Siat 8A) (fragment) | Tetraodon nigroviridis | n.d. | AJ715536 | CAG29375.1 | | |
| α-2,8-sialyltransferase ST8Sia II (Siat 8B) (fragment) | Tetraodon nigroviridis | n.d. | AJ715537 | CAG29376.1 | | |
| α-2,8-sialyltransferase ST8Sia III (Siat 8C) (fragment) | Tetraodon nigroviridis | n.d. | AJ715539 | CAG29378.1 | | |
| α-2,8-sialyltransferase ST8Sia IIIr (Siat 8Cr) (fragment) | Tetraodon nigroviridis | n.d. | AJ715540 | CAG29379.1 | | |
| α-2,8-sialyltransferase ST8Sia V (Siat 8E) (fragment) | Tetraodon nigroviridis | n.d. | AJ715548 | CAG29387.1 | | |
| α-2,3-sialyltransferase (St3Gal-II) | Xenopus laevis | n.d. | AJ585762 | CAE51386.1 | | |
| α-2,3-sialyltransferase (St3Gal-VI) | Xenopus laevis | n.d. | AJ585766 | CAE51390.1 | | |
| α-2,3-sialyltransferase St3Gal-III (Siat6) | Xenopus laevis | n.d. | AJ585764 AJ626823 | CAE51388.1 CAF25181.1 | | |
| α-2,8-polysialyltransferase | Xenopus laevis | 2.4.99.- | AB007468 | BAA32617.1 | O93234 | |
| α-2,8-sialyltransferase ST8Siα-I (Siat8A;GD3 synthase) | Xenopus laevis | n.d. | AY272056 AY272057 AJ704562 | AAQ16162.1 AAQ16163.1 CAG28695.1 | | |
| Unknown (protein for MGC:81265) | Xenopus laevis | n.d. | BC068760 | AAH68760.1 | | |
| α-2,3-sialyltransferase (3Gal-VI) | Xenopus tropicalis | n.d. | AJ626744 | CAF25054.1 | | |
| α-2,3-sialyltransferase (Siat4c) | Xenopus tropicalis | n.d. | AJ622908 | CAF22058.1 | | |
| α-2,6-sialyltransferase ST6GalNAc V (Siat7E) (fragment) | Xenopus tropicalis | n.d. | AJ646878 | CAG26707.1 | | |
| α-2,8-sialyltransferase ST8Sia III (Siat 8C) (fragment) | Xenopus tropicalis | n.d. | AJ715544 | CAG29383.1 | | |
| β-galactosamide α-2,6-sialyltransferase II (ST6Gal II) | Xenopus tropicalis | n.d. | AJ627628 | CAF29496.1 | | |
| sialytransferase St8Sial | Xenopus tropicalis | n.d. | AY652775 | AAT67042 | | |
| poly-α-2,8-sialosyl sialyltransferase (NeuS) | Escherichia coli K1 | 2.4.-.- | M76370 X60598 | AAA24213.1 CAA43053.1 | Q57269 | |
| polysialyltransferase | Escherichia coli K92 | 2.4.-.- | M88479 | AAA24215.1 | Q47404 | |

FIGURE 7L

| Protein | Organism | EC# | GenBank / GenPept | | SwissProt | PDB /3D |
|---|---|---|---|---|---|---|
| α-2,8 polysialyltransferase SiaD | Neisseria meningitidis B1940 | 2.4.-.- | M95053 X78068 | AAA20478.1 CAA54985.1 | Q51281 Q51145 | |
| SynE | Neisseria meningitidis FAM18 | n.d. | U75650 | AAB53842.1 | O06435 | |
| polysialyltransferase (SiaD)(fragment) | Neisseria meningitidis M1019 | n.d. | AY234192 | AAO85290.1 | | |
| SiaD (fragment) | Neisseria meningitidis M209 | n.d. | AY281046 | AAP34769.1 | | |
| SiaD (fragment) | Neisseria meningitidis M3045 | n.d. | AY281044 | AAP34767.1 | | |
| polysialyltransferase (SiaD)(fragment) | Neisseria meningitidis M3315 | n.d. | AY234191 | AAO85289.1 | | |
| SiaD (fragment) | Neisseria meningitidis M3515 | n.d. | AY281047 | AAP34770.1 | | |
| polysialyltransferase (SiaD)(fragment) | Neisseria meningitidis M4211 | n.d. | AY234190 | AAO85288.1 | | |
| SiaD (fragment) | Neisseria meningitidis M4642 | n.d. | AY281048 | AAP34771.1 | | |
| polysialyltransferase (SiaD)(fragment) | Neisseria meningitidis M5177 | n.d. | AY234193 | AAO85291.1 | | |
| SiaD | Neisseria meningitidis M5178 | n.d. | AY281043 | AAP34766.1 | | |
| SiaD (fragment) | Neisseria meningitidis M980 | n.d. | AY281045 | AAP34768.1 | | |
| NMB0067 | Neisseria meningitidis MC58 | n.d. | NC_003112 | NP_273131 | | |
| Lst | Aeromonas punctata Sch3 | n.d. | AF126256 | AAS66624.1 | | |
| ORF2 | Haemophilus influenzae A2 | n.d. | M94855 | AAA24979.1 | | |
| HI1699 | Haemophilus influenzae Rd | n.d. | U32842 NC_000907 | AAC23345.1 NP_439841.1 | Q48211 | |
| α-2,3-sialyltransferase | Neisseria gonorrhoeae F62 | 2.4.99.4 | U60664 | AAC44539.1 AAE67205.1 | P72074 | |
| α-2,3-sialyltransferase | Neisseria meningitidis 126E, NRCC 4010 | 2.4.99.4 | U60662 | AAC44544.2 | | |
| α-2,3-sialyltransferase | Neisseria meningitidis 406Y, NRCC 4030 | 2.4.99.4 | U60661 | AAC44543.1 | | |
| α-2,3-sialyltransferase (NMB0922) | Neisseria meningitidis MC58 | 2.4.99.4 | U60660 AE002443 NC_003112 | AAC44541.1 AAF41330.1 NP_273962.1 | P72097 | |
| NMA1118 | Neisseria meningitidis Z2491 | n.d. | AL162755 NC_003116 | CAB84380.1 NP_283887.1 | Q9JUV5 | |
| PM0508 | Pasteurella multocida PM70 | n.d. | AE006086 NC_002663 | AAK02592.1 NP_245445.1 | Q9CNC4 | |
| WaaH | Salmonella enterica SARB25 | n.d. | AF519787 | AAM82550.1 | Q8KS93 | |
| WaaH | Salmonella enterica SARB3 | n.d. | AF519788 | AAM82551.1 | Q8KS92 | |
| WaaH | Salmonella enterica SARB39 | n.d. | AF519789 | AAM82552.1 | | |
| WaaH | Salmonella enterica SARB53 | n.d. | AF519790 | AAM82553.1 | | |
| WaaH | Salmonella enterica SARB57 | n.d. | AF519791 | AAM82554.1 | Q8KS91 | |
| WaaH | Salmonella enterica SARB71 | n.d. | AF519793 | AAM82556.1 | Q8KS89 | |
| WaaH | Salmonella enterica | n.d. | AF519792 | AAM82555.1 | Q8KS90 | |

FIGURE 7M

| Protein | Organism | EC# | GenBank / GenPept | | SwissProt | PDB /3D |
|---|---|---|---|---|---|---|
| | SARB8 | | | | | |
| WaaH | Salmonella enterica SARC10V | n.d. | AF519779 | AAM88840.1 | Q8KS99 | |
| WaaH (fragment) | Salmonella enterica SARC12 | n.d. | AF519781 | AAM88842.1 | | |
| WaaH (fragment) | Salmonella enterica SARC13I | n.d. | AF519782 | AAM88843.1 | Q8KS98 | |
| WaaH (fragment) | Salmonella enterica SARC14I | n.d. | AF519783 | AAM88844.1 | Q8KS97 | |
| WaaH | Salmonella enterica SARC15II | n.d. | AF519784 | AAM88845.1 | Q8KS96 | |
| WaaH | Salmonella enterica SARC16II. | n.d. | AF519785 | AAM88846.1 | Q8KS95 | |
| WaaH (fragment) | Salmonella enterica SARC3I | n.d. | AF519772 | AAM88834.1 | Q8KSA4 | |
| WaaH (fragment) | Salmonella enterica SARC4I | n.d. | AF519773 | AAM88835.1 | Q8KSA3 | |
| WaaH | Salmonella enterica SARC5IIa | n.d. | AF519774 | AAM88836.1 | | |
| WaaH | Salmonella enterica SARC6IIa | n.d. | AF519775 | AAM88837.1 | Q8KSA2 | |
| WaaH | Salmonella enterica SARC8 | n.d. | AF519777 | AAM88838.1 | Q8KSA1 | |
| WaaH | Salmonella enterica SARC9V | n.d. | AF519778 | AAM88839.1 | Q8KSA0 | |
| UDP-glucose : α-1,2-glucosyltransferase (WaaH) | Salmonella enterica subsp. arizonae SARC 5 | 2.4.1.- | AF511116 | AAM48166.1 | | |
| bifunctional α-2,3/-2,8-sialyltransferase (Cst-II) | Campylobacter jejuni ATCC 43449 | n.d. | AF401529 | AAL06004.1 | Q93CZ5 | |
| Cst | Campylobacter jejuni 81-176 | n.d. | AF305571 | AAL09368.1 | | |
| α-2,3-sialyltransferase (Cst-III) | Campylobacter jejuni ATCC 43429 | 2.4.99.- | AY044156 | AAK73183.1 | | |
| α-2,3-sialyltransferase (Cst-III) | Campylobacter jejuni ATCC 43430 | 2.4.99.- | AF400047 | AAK85419.1 | | |
| α-2,3-sialyltransferase (Cst-II) | Campylobacter jejuni ATCC 43432 | 2.4.99.- | AF215659 | AAG43979.1 | Q9F0M9 | |
| α-2,3/8-sialyltransferase (CstII) | Campylobacter jejuni ATCC 43438 | n.d. | AF400048 | AAK91725.1 | Q93MQ0 | |
| α-2,3-sialyltransferase cst-II | Campylobacter jejuni ATCC 43446 | 2.4.99.- | AF167344 | AAF34137.1 | | |
| α-2,3-sialyltransferase (Cst-II) | Campylobacter jejuni ATCC 43456 | 2.4.99.- | AF401528 | AAL05990.1 | Q93D05 | |
| α-2,3-/α-2,8-sialyltransferase (CstII) | Campylobacter jejuni ATCC 43460 | 2.4.99.- | AY044868 | AAK96001.1 | Q938X6 | |
| α-2,3/8-sialyltransferase (Cst-II) | Campylobacter jejuni ATCC 700297 | n.d. | AF216647 | AAL36462.1 | | |
| ORF | Campylobacter jejuni GB11 | n.d. | AY422197 | AAR82875.1 | | |
| α-2,3-sialyltransferase cstIII | Campylobacter jejuni MSC57360 | 2.4.99.- | AF195055 | AAG29922.1 | | |
| α-2,3-sialyltransferase cstIII Cj1140 | Campylobacter jejuni NCTC 11168 | 2.4.99.- | AL139077 NC_002163 | CAB73395.1 NP_282288.1 | Q9PNF4 | |
| α-2,3/α-2,8-sialyltransferase II (cstII) | Campylobacter jejuni O:10 | n.d. | - AX934427 | AAO96669.1 CAF04167.1 | | |
| α-2,3/α-2,8-sialyltransferase II (CstII) | Campylobacter jejuni O:19 | n.d. | AX934431 | CAF04169.1 | | |
| α-2,3/α-2,8-sialyltransferase II (CstII) | Campylobacter jejuni O:36 | n.d. | AX934436 | CAF04171.1 | | |
| α-2,3/α-2,8- | Campylobacter | n.d. | AX934434 | CAF04170.1 | | |

FIGURE 7N

| Protein | Organism | EC# | GenBank / GenPept | | SwissProt | PDB /3D | |
|---|---|---|---|---|---|---|---|
| sialyltransferase II (CstII) | jejuni O:4 | | | | | | |
| α-2,3/α-2,8-sialyltransferase II (CstII) | Campylobacter jejuni O:41 | n.d. | -<br>-<br>AX934429 | AAO96670.1<br>AAT17967.1<br>CAF04168.1 | | | |
| α-2,3-sialyltransferase cst-I | Campylobacter jejuni OH4384 | 2.4.99.- | AF130466 | AAF13495.1<br>AAS36261.1 | Q9RGF1 | | |
| bifunctional α-2,3/-2,8-sialyltransferase (Cst-II) | Campylobacter jejuni OH4384 | 2.4.99.- | AF130984<br>AX934425 | AAF31771.1<br>CAF04166.1 | | 1RO7<br>1RO8 | C<br>A |
| HI0352 (fragment) | Haemophilus influenzae Rd | n.d. | U32720<br>X57315<br>NC_000907 | AAC22013.1<br>CAA40567.1<br>NP_438516.1 | P24324 | | |
| PM1174 | Pasteurella multocida PM70 | n.d. | AE006157<br>NC_002663 | AAK03258.1<br>NP_246111.1 | Q9CLP3 | | |
| Sequence 10 from patent US 6503744 | Unknown. | n.d. | - | AAO96672.1 | | | |
| Sequence 10 from patent US 6699705 | Unknown. | n.d. | - | AAT17969.1 | | | |
| Sequence 12 from patent US 6699705 | Unknown. | n.d. | - | AAT17970.1 | | | |
| Sequence 2 from patent US 6709834 | Unknown. | n.d. | - | AAT23232.1 | | | |
| Sequence 3 from patent US 6503744 | Unknown. | n.d. | - | AAO96668.1 | | | |
| Sequence 3 from patent US 6699705 | Unknown. | n.d. | - | AAT17965.1 | | | |
| Sequence 34 from patent US 6503744 | Unknown. | n.d. | - | AAO96684.1 | | | |
| Sequence 35 from patent US 6503744 (fragment) | Unknown. | n.d. | -<br>- | AAO96685.1<br>AAS36262.1 | | | |
| Sequence 48 from patent US 6699705 | Unknown. | n.d. | - | AAT17988.1 | | | |
| Sequence 5 from patent US 6699705 | Unknown. | n.d. | - | AAT17966.1 | | | |
| Sequence 9 from patent US 6503744 | Unknown. | n.d. | - | AAO96671.1 | | | |

A

B b = 1-6
c = 0,1
t = 0,1

```
                       SEQUENCE LISTING

<160> NUMBER OF SEQ ID NOS: 11

<210> SEQ ID NO 1
<211> LENGTH: 175
<212> TYPE: PRT
<213> ORGANISM: Homo Sapiens

<400> SEQUENCE: 1

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 2
<211> LENGTH: 174
<212> TYPE: PRT
<213> ORGANISM: Homo sapiens

<400> SEQUENCE: 2

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60
```

-continued

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
            85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 3
<211> LENGTH: 178
<212> TYPE: PRT
<213> ORGANISM: Artificial Sequence
<220> FEATURE:
<223> OTHER INFORMATION: GCSF variant

<400> SEQUENCE: 3

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Val Ser Glu Cys Ala Thr Tyr Lys Leu Cys His Pro
        35                  40                  45

Glu Glu Leu Val Leu Leu Gly His Ser Leu Gly Ile Pro Trp Ala Pro
    50                  55                  60

Leu Ser Ser Cys Pro Ser Gln Ala Leu Gln Leu Ala Gly Cys Leu Ser
65                  70                  75                  80

Gln Leu His Ser Gly Leu Phe Leu Tyr Gln Gly Leu Leu Gln Ala Leu
                85                  90                  95

Glu Gly Ile Ser Pro Glu Leu Gly Pro Thr Leu Asp Thr Leu Gln Leu
            100                 105                 110

Asp Val Ala Asp Phe Ala Thr Thr Ile Trp Gln Gln Met Glu Glu Leu
        115                 120                 125

Gly Met Ala Pro Ala Leu Gln Pro Thr Gln Gly Ala Met Pro Ala Phe
    130                 135                 140

Ala Ser Ala Phe Gln Arg Arg Ala Gly Gly Val Leu Val Ala Ser His
145                 150                 155                 160

Leu Gln Ser Phe Leu Glu Val Ser Tyr Arg Val Leu Arg His Leu Ala
                165                 170                 175

Gln Pro

<210> SEQ ID NO 4
<211> LENGTH: 204
<212> TYPE: PRT
<213> ORGANISM: Artificial Sequence
<220> FEATURE:
<223> OTHER INFORMATION: GCSF variant

<400> SEQUENCE: 4

Met Ala Gly Pro Ala Thr Gln Ser Pro Met Lys Leu Met Ala Leu Gln
1               5                   10                  15

```
Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
         35                  40                  45

Glu Gln Val Arg Lys Ile Gln Gly Asp Gly Ala Ala Leu Gln Glu Lys
 50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                 85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200

<210> SEQ ID NO 5
<211> LENGTH: 207
<212> TYPE: PRT
<213> ORGANISM: Artificial Sequence
<220> FEATURE:
<223> OTHER INFORMATION: GCSF variant

<400> SEQUENCE: 5

Met Ala Gly Pro Ala Thr Gln Ser Pro Met Lys Leu Met Ala Leu Gln
 1               5                  10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
         35                  40                  45

Glu Gln Val Arg Lys Ile Gln Gly Asp Gly Ala Ala Leu Gln Glu Lys
 50                  55                  60

Leu Val Ser Glu Cys Ala Thr Tyr Lys Leu Cys His Pro Glu Glu Leu
 65                  70                  75                  80

Val Leu Leu Gly His Ser Leu Gly Ile Pro Trp Ala Pro Leu Ser Ser
                 85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
```

```
                180                 185                 190
Phe Leu Glu Val Ser Tyr Arg Val Leu Arg His Leu Ala Gln Pro
                    195                 200                 205

<210> SEQ ID NO 6
<211> LENGTH: 176
<212> TYPE: PRT
<213> ORGANISM: Artificial Sequence
<220> FEATURE:
<223> OTHER INFORMATION: GCSF variant

<400> SEQUENCE: 6

Met Val Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Thr Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 7
<211> LENGTH: 175
<212> TYPE: PRT
<213> ORGANISM: Artificial Sequence
<220> FEATURE:
<223> OTHER INFORMATION: GCSF variant

<400> SEQUENCE: 7

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Thr Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
```

```
            115                 120                 125
Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 8
<211> LENGTH: 176
<212> TYPE: PRT
<213> ORGANISM: Artificial Sequence
<220> FEATURE:
<223> OTHER INFORMATION: G-CSF variant

<400> SEQUENCE: 8

Met Val Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
            35                  40                  45

Leu Val Leu Leu Gly Ser Ser Leu Gly Ile Pro Trp Ala Pro Leu Ser
        50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
                100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
        130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 9
<211> LENGTH: 176
<212> TYPE: PRT
<213> ORGANISM: Artificial Sequence
<220> FEATURE:
<223> OTHER INFORMATION: G-CSF variant

<400> SEQUENCE: 9

Met Gln Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
        50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
```

```
                    85                  90                  95
Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
            130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 10
<211> LENGTH: 181
<212> TYPE: PRT
<213> ORGANISM: Artificial Sequence
<220> FEATURE:
<223> OTHER INFORMATION: G-CSF variant

<400> SEQUENCE: 10

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Thr
                165                 170                 175

Gln Gly Ala Met Pro
            180

<210> SEQ ID NO 11
<211> LENGTH: 175
<212> TYPE: PRT
<213> ORGANISM: Artificial Sequence
<220> FEATURE:
<223> OTHER INFORMATION: G-CSF variant

<400> SEQUENCE: 11

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
```

|  |  |  |  |  | 35 |  |  |  |  | 40 |  |  |  |  | 45 |  |  |
|---|---|---|---|---|---|---|---|---|---|---|---|---|---|---|---|---|---|
| Val | Leu | Leu | Gly | Ser | Ser | Leu | Gly | Ile | Pro | Trp | Ala | Pro | Leu | Ser | Ser |  |  |
|  | 50 |  |  |  |  | 55 |  |  |  |  | 60 |  |  |  |  |  |  |
| Cys | Pro | Ser | Gln | Ala | Leu | Gln | Leu | Ala | Gly | Cys | Leu | Ser | Gln | Leu | His |  |  |
| 65 |  |  |  |  | 70 |  |  |  |  | 75 |  |  |  |  | 80 |  |  |
| Ser | Gly | Leu | Phe | Leu | Tyr | Gln | Gly | Leu | Leu | Gln | Ala | Leu | Glu | Gly | Ile |  |  |
|  |  |  |  | 85 |  |  |  |  | 90 |  |  |  |  | 95 |  |  |  |
| Ser | Pro | Glu | Leu | Gly | Pro | Thr | Leu | Asp | Thr | Leu | Gln | Leu | Asp | Val | Ala |  |  |
|  |  |  |  | 100 |  |  |  |  | 105 |  |  |  |  | 110 |  |  |  |
| Asp | Phe | Ala | Thr | Thr | Ile | Trp | Gln | Gln | Met | Glu | Glu | Leu | Gly | Met | Ala |  |  |
|  |  |  | 115 |  |  |  |  | 120 |  |  |  |  | 125 |  |  |  |  |
| Pro | Thr | Thr | Thr | Pro | Thr | Gln | Thr | Ala | Met | Pro | Ala | Phe | Ala | Ser | Ala |  |  |
|  |  | 130 |  |  |  |  | 135 |  |  |  |  | 140 |  |  |  |  |  |
| Phe | Gln | Arg | Arg | Ala | Gly | Gly | Val | Leu | Val | Ala | Ser | His | Leu | Gln | Ser |  |  |
| 145 |  |  |  |  | 150 |  |  |  |  | 155 |  |  |  |  | 160 |  |  |
| Phe | Leu | Glu | Val | Ser | Tyr | Arg | Val | Leu | Arg | His | Leu | Ala | Gln | Pro |  |  |  |
|  |  |  |  | 165 |  |  |  |  | 170 |  |  |  |  | 175 |  |  |  |

GLYCOPEGYLATED GRANULOCYTE COLONY STIMULATING FACTOR

CROSS-REFERENCES TO RELATED APPLICATIONS

The present application claims priority under 35 USC §119 (e) to U.S. Provisional Patent Application No. 60/684,851, filed on May 25, 2005 and is a continuation-in-part of PCT Application No. US/2004/041004, filed Dec. 3, 2004 which applications are incorporated herein in their entirety for all purposes; PCT Application No. US/2004/041004, filed Dec. 3, 2004 claims priority under 35 USC §119(e) to U.S. Provisional Patent Application No. 60/526,796, filed on Dec. 3, 2003, U.S. Provisional Patent Application No. 60/539,387, filed on Jan. 26, 2004, U.S. Provisional Patent Application No. 60/555,813, filed on Mar. 23, 2004, U.S. Provisional Patent Application No. 60/570,282, filed on May 11, 2004, U.S. Provisional Patent Application No. 60/592,744, filed on Jul. 29, 2004, U.S. Provisional Patent Application No. 60/614,518, filed on Sep. 29, 2004, and U.S. Provisional Patent Application No. 60/623,387, filed on Oct. 29, 2004.

BACKGROUND OF THE INVENTION

Granulocyte colony stimulating factor (G-CSF) is a glycoprotein which stimulates the survival, proliferation, differentiation and function of neutrophil granulocyte progenitor cells and mature neutrophils. The two forms of recombinant human G-CSF in clinical use are potent stimulants of neutrophil granulopoiesis and have demonstrated efficacy in preventing infectious complications of some neutropenic states. They can be used to accelerate neutrophil recovery from myelosuppressive treatments.

G-CSF decreases the morbidity of cancer chemotherapy by reducing the incidence of febrile neutropenia, the morbidity of high-dose chemotherapy supported by marrow transplantation, and the incidence and duration of infection in patients with severe chronic neutropenia. Further, G-CSF has recently been shown to have therapeutic when administered after the onset of myocardial infarction.

The human form of G-CSF was cloned by groups from Japan and the U.S.A. in 1986 (see e.g., Nagata et al. *Nature* 319: 415-418, 1986). The natural human glycoprotein exists in two forms, one of 175 and the other of 178 amino acids. The more abundant and more active 175 amino form has been used in the development of pharmaceutical products by recombinant DNA technology.

The recombinant human G-CSF synthesised in an *E. coli* expression system is called filgrastim. The structure of filgrastim differs slightly from the natural glycoprotein. The other form of recombinant human G-CSF is called lenograstim and is synthesised in Chinese hamster ovary (CHO) cells.

hG-CSF is a monomeric protein that dimerizes the G-CSF receptor by formation of a 2:2 complex of 2 G-CSF molecules and 2 receptors (Horan et al. *Biochemistry*, 35(15): 4886-96 (1996)). The following hG-CSF residues have been identified by X-ray crystalographic studies as being part of the receptor binding interfaces: G4, P5, A6, S7, S8, L9, P10, Q11, S12, L15, K16, E19, Q20, L108, D109, D112, T115, T116, Q119, E122, E123, and L124 (see e.g., Aritomi et al., (1999) *Nature* 401: 713).

The commercially available forms of rhG-CSF have a short-term pharmacological effect and must often be administered more once a day for the duration of the leukopenic state. A molecule with a longer circulation half-life would decrease the number of administrations necessary to alleviate the leukopenia and prevent consequent infections. Another problem with currently available rG-CSF products is the occurrence of dose-dependent bone pain. Since bone pain is experienced by patients as a significant side effect of treatment with rG-CSF, it would be desirable to provide a rG-CSF product that does not cause bone pain, either by means of a product that inherently does not have this effect or that is effective in a sufficiently small dose that no bone pain is caused. Thus, there is clearly a need for improved recombinant G-CSF molecules.

Protein-engineered variants of hG-CSF have been reported (U.S. Pat. Nos. 5,581,476, 5,214,132, 5,362,853, 4,904,584 and Riedhaar-Olson et al. Biochemistry 35: 9034-9041, 1996). Modification of hG-CSF and other polypeptides so as to introduce at least one additional carbohydrate chain as compared to the native polypeptide has also been reported (U.S. Pat. No. 5,218,092). In addition, polymer modifications of native hG-CSF, including attachment of PEG groups, have been reported and studied (see e.g., Satake-Ishikawa et al., (1992) *Cell Structure and Function* 17: 157; Bowen et al. (1999) *Experimental Hematology* 27: 425; U.S. Pat. Nos. 5,824,778, 5,824,784, WO 96/11953, WO 95/21629, and WO 94/20069).

The attachment of synthetic polymers to the peptide backbone in an attempt to improve the pharmacokinetic properties of glycoprotein therapeutics is known in the art. An exemplary polymer that has been conjugated to peptides is poly (ethylene glycol) ("PEG"). The use of PEG to derivatize peptide therapeutics has been demonstrated to reduce the immunogenicity of the peptides. For example, U.S. Pat. No. 4,179,337 (Davis et al.) discloses non-immunogenic polypeptides such as enzymes and peptide hormones coupled to polyethylene glycol (PEG) or polypropylene glycol. In addition to reduced immunogenicity, the clearance time in circulation is prolonged due to the increased size of the PEG-conjugate of the polypeptides in question.

The principal mode of attachment of PEG, and its derivatives, to peptides is a non-specific bonding through a peptide amino acid residue (see e.g., U.S. Pat. Nos. 4,088,538, 4,496, 689, 4,414,147, 4,055,635, and PCT WO 87/00056). Another mode of attaching PEG to peptides is through the non-specific oxidation of glycosyl residues on a glycopeptide (see e.g., WO 94/05332).

In these non-specific methods, poly(ethyleneglycol) is added in a random, non-specific manner to reactive residues on a peptide backbone. Of course, random addition of PEG molecules has its drawbacks, including a lack of homogeneity of the final product, and the possibility for reduction in the biological or enzymatic activity of the peptide. Therefore, for the production of therapeutic peptides, a derivitization strategy that results in the formation of a specifically labeled, readily characterizable, essentially homogeneous product is superior. Such methods have been developed.

Specifically labeled, homogeneous peptide therapeutics can be produced in vitro through the action of enzymes. Unlike the typical non-specific methods for attaching a synthetic polymer or other label to a peptide, enzyme-based syntheses have the advantages of regioselectivity and stereoselectivity. Two principal classes of enzymes for use in the synthesis of labeled peptides are glycosyltransferases (e.g., sialyltransferases, oligosaccharyltransferases, N-acetylglucosaminyltransferases), and glycosidases. These enzymes can be used for the specific attachment of sugars which can be subsequently modified to comprise a therapeutic moiety. Alternatively, glycosyltransferases and modified glycosidases can be used to directly transfer modified sugars to a peptide backbone (see e.g., U.S. Pat. No. 6,399,336, and U.S. Patent Application Publications 20030040037, 20040132640, 20040137557, 20040126838, and 20040142856, each of which are incorporated by reference herein). Methods combining both chemical and enzymatic synthetic elements are also known (see e.g., Yamamoto et al. *Carbohydr. Res.* 305: 415-422 (1998) and U.S. Patent Application Publication 20040137557 which is incorporated herein by reference).

In response to the need for improved therapeutic G-CSF, the present invention provides a glycopegylated G-CSF that is therapeutically active and which has pharmacokinetic parameters and properties that are improved relative to an identical, or closely analogous, G-CSF peptide that is not glycopegylated. Furthermore, the invention provides method for producing cost effectively and on an industrial scale the improved G-CSF peptides of the invention.

SUMMARY OF THE INVENTION

It has now been discovered that the controlled modification of Granulocyte colony stimulating factor (G-CSF) with one or more poly(ethylene glycol) moieties affords a novel G-CSF derivative with pharmacokinetic properties that are improved relative to the corresponding native (un-pegylated) G-CSF (FIG. 3). Moreover, the pharmacological activity of the glycopegylated G-CSF is approximately the same as the commercially available mono-pegylated filgrastim (FIG. 4).

In an exemplary embodiment, "glycopeglyated" G-CSF molecules of the invention are produced by the enzyme mediated formation of a conjugate between a glycosylated or non-glycosylated G-CSF peptide and an enzymatically transferable saccharyl moiety that includes a poly(ethylene glycol) moiety within its structure The PEG moiety is attached to the saccharyl moiety directly (i.e., through a single group formed by the reaction of two reactive groups) or through a linker moiety, e.g., substituted or unsubstituted alkyl, substituted or unsubstituted heteroalkyl, etc. An exemplary transferable PEG-saccharyl structure is set forth in FIG. 5.

Thus, in one aspect, the present invention provides a conjugate between a PEG moiety, e.g., PEG and a peptide that has an in vivo activity similar or otherwise analogous to art-recognized G-CSF. In the conjugate of the invention, the PEG moiety is covalently attached to the peptide via an intact glycosyl linking group. Exemplary intact glycosyl linking groups include sialic acid moieties that are derivatized with PEG.

The polymeric modifying moiety can be attached at any position of a glycosyl moiety of G-CSF. Moreover, the polymeric modifying moiety can be bound to a glycosyl residue at any position in the amino acid sequence of a wild type or mutant G-CSF peptide.

In an exemplary embodiment, the invention provides an G-CSF peptide that is conjugated through a glycosyl linking group to a polymeric modifying moiety. Exemplary G-CSF peptide conjugates include a glycosyl linking group having a formula selected from:

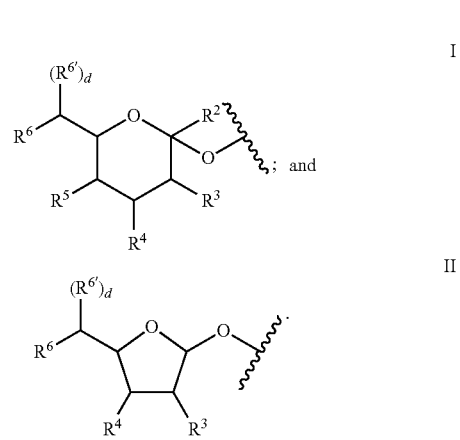

In Formulae I and II, $R^2$ is H, $CH_2OR^7$, $COOR^7$ or $OR^7$, in which $R^7$ represents H, substituted or unsubstituted alkyl or substituted or unsubstituted heteroalkyl. The symbols $R^3$, $R^4$, $R^5$, $R^6$ and $R^{6'}$ independently represent H, substituted or unsubstituted alkyl, $OR^8$, $NHC(O)R^9$. The index d is 0 or 1. $R^8$ and $R^9$ are independently selected from H, substituted or unsubstituted alkyl, substituted or unsubstituted heteroalkyl or sialic acid. At least one of $R^3$, $R^4$, $R^5$, $R^6$ or $R^{6'}$ includes the polymeric modifying moiety e.g, PEG. In an exemplary embodiment, $R^6$ and $R^{6'}$, together with the carbon to which they are attached are components of the side chain of sialic acid. In a further exemplary embodiment, this side chain is functionalized with the polymeric modifying moiety.

In an exemplary embodiment, the polymeric moiety is bound to the glycosyl linking group, generally through a heteroatom on the glycosyl core (e.g., N, O), through a linker, L, as shown below:

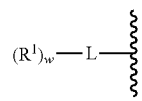

$R^1$ is the polymeric modifying moiety and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety. Another exemplary linking group is an amino acid residue (e.g., cysteine, serine, lysine, and short oligopeptides, e.g., Lys-Lys, Lys-Lys-Lys, Cys-Lys, Ser-Lys, etc.)

When L is a bond, it is formed by reaction of a reactive functional group on a precursor of $R^1$ and a reactive functional group of complementary reactivity on a precursor of the glycosyl linking group. When L is a non-zero order linking group, L can be in place on the glycosyl moiety prior to reaction with the $R^1$ precursor. Alternatively, the precursors of $R^1$ and L can be incorporated into a preformed cassette that is subsequently attached to the glycosyl moiety. As set forth herein, the selection and preparation of precursors with appropriate reactive functional groups is within the ability of those skilled in the art. Moreover, coupling of the precursors proceeds by chemistry that is well understood in the art.

In an exemplary embodiment L is a linking group that is formed from an amino acid, or small peptide (e.g., 1-4 amino acid residues) providing a modified sugar in which the polymeric modifying moiety is attached through a substituted alkyl linker. Exemplary linkers include glycine, lysine, serine and cysteine. Amino acid analogs, as defined herein, are also of use as linker components. The amino acid may be modified with an additional component of a linker, e.g., alkyl, heteroalkyl, covalently attached through an acyl linkage, for example, an amide or urethane formed through an amine moiety of the amino acid residue.

In an exemplary embodiment, the glycosyl linker has a structure according to Formula I and $R^5$ includes the polymeric modifying moiety. In another exemplary embodiment, $R^5$ includes both the polymeric modifying moiety and a linker, L, joining the modifying moiety to the glycosyl core. L can be a linear or branched structure. Similarly, the polymeric modifying can be branched or linear.

The polymeric modifying moiety comprises two or more repeating units that can be water-soluble or essentially insoluble in water. Exemplary water-soluble polymers of use in the compounds of the invention include PEG, e.g., m-PEG, PPG, e.g., m-PPG, polysialic acid, polyglutamate, polyaspartate, polylysine, polyetheyleneimine, biodegradable polymers (e.g., polylactide, polyglyceride), and functionalized PEG, e.g., terminal-functionalized PEG.

The glycosyl core of the glycosyl linking groups of use in the G-CSF conjugates of the invention is selected from both natural and unnatural furanoses and pyranoses. The unnatural saccharides optionally include an alkylated or acylated hydroxyl and/or amine moiety, e.g., ethers, esters and amide substituents on the ring. Other unnatural saccharides include an H, hydroxyl, ether, ester or amide substituent at a position on the ring at which such a substituent is not present in the natural saccharide. Alternatively, the carbohydrate is missing a substituent that would be found in the carbohydrate from which its name is derived, e.g., deoxy sugars. Still further exemplary unnatural sugars include both oxidized (e.g., -onic and -uronic acids) and reduced (sugar alcohols) carbohydrates. The sugar moiety can be a mono-, oligo- or polysaccharide.

Exemplary natural sugars of use as components of glycosyl linking groups in the present invention include glucose, glucosamine, galactose, galactosamine, fucose, mannose, mannosamine, xylanose, ribose, N-acetyl glucose, N-acetyl glucosamine, N-acetyl galactose, N-acetyl galactosamine, and sialic acid.

In one embodiment, the present invention provides an G-CSF peptide comprising the moiety:

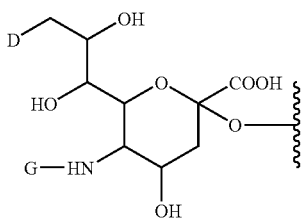

wherein D is a member selected from —OH and $R^1$-L-HN—; G is a member selected from H and $R^1$-L- and —C(O)(C$_1$-C$_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is $R^1$-L-, and when G is —C(O)(C$_1$-C$_6$)alkyl, D is $R^1$-L-NH—.

In another aspect, the invention provides a peptide comprising a glycosyl linking group having the formula:

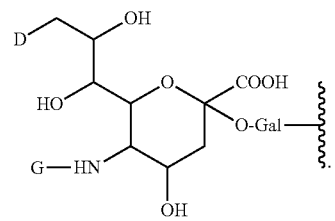

In other embodiments, the group has the formula:

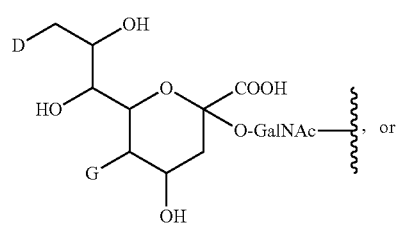

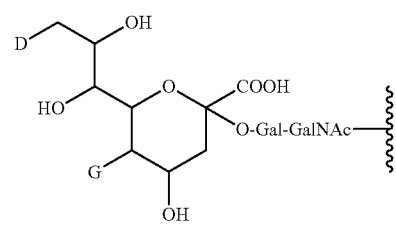

in which t is 0 or 1.

In yet another embodiment, the group has the formula:

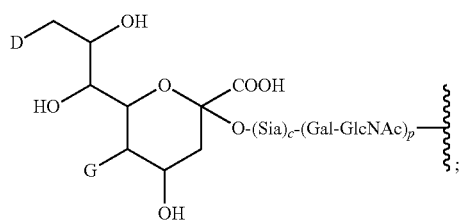

in which the index p represents and integer from 1 to 10, and c represents 0 or 1.

In another aspect, the invention provides a method of making a PEGylated G-CSF peptide of the invention. The method includes: (a) contacting a substrate G-CSF peptide comprising a glycosyl group selected from:

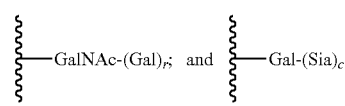

with a PEG-sialic acid donor having the formula:

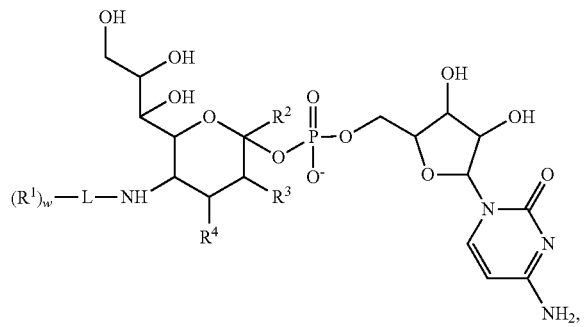

and an enzyme that transfers PEG-sialic acid from said donor onto a member selected from the GalNAc, Gal and the Sia of said glycosyl group, under conditions appropriate for said transfer. An exemplary modified sialic acid donor is CMP-sialic acid modified, through a linker moiety, with a polymer, e.g., a straight chain or branched poly(ethylene glycol) moiety. The indices c and r independently represent 0 or 1.

The peptide can be acquired from essentially any source, however, in one embodiment, prior to being modified as discussed above, the G-CSF peptide is expressed in a suitable host. Mammalian (e.g., CHO), bacteria (e.g., E. coli) and insect cells (e.g., Sf-9) are exemplary expression systems providing G-CSF of use in the compositions and methods set forth herein. An exmplary O-linked glycan that is glycopegylated is shown in FIG. 8 Exemplary glycans produced in an insect system and a mammalian system, and subsequently glycoconjugated and or remodeled and glycoconjugated to PEG are set forth in FIG. 9 and FIG. 10.

In another aspect, the invention provides a method of treating a condition in a subject in need thereof. Exemplary conditions include those characterized by compromised red blood cell production in the subject. The method includes the step of administering to the subject an amount of the polymer-modified G-CSF peptide of the invention effective to ameliorate the condition in the subject.

In exemplary embodiments, a G-CSF peptide of the invention may be administered to patients for the purposed of preventing infection in cancer patients undergoing certain types of radiation therapy, chemotherapy, and bone marrow transplantations, to mobilize progenitor cells for collection in peripheral blood progenitor cell transplantations, for treatment of severe chronic or relative leukopenia, irrespective of cause, and to support treatment of patients with acute myeloid leukaemia. Additionally, the polypeptide conjugate or composition of the invention may be used for treatment of AIDS or other immunodeficiency diseases as well as bacterial infections, and Hepatisis A, B, and C.

In another aspect, the invention provides a pharmaceutical formulation comprising a polymer-modified G-CSF peptide of the invention and a pharmaceutically acceptable carrier.

In the polymer-modified G-CSF glycoconjugates of the invention, essentially each of the amino acid residues to which the polymer is bound has the same structure. For example, if one peptide includes a Thr linked glycosyl residue, at least about 70%, 80%, 90%, 95%, 97%, 99%, 99.2%, 99.4%, 99.6%, or more preferably 99.8% of the peptides in the population will have the same glycosyl residue covalently bound to the same Thr residue.

Other objects and advantages of the invention will be apparent to those of skill in the art from the detailed description that follows.

DESCRIPTION OF THE DRAWINGS

FIG. 6 shows exemplary G-CSF amino acid sequences. SEQ ID NO:1 is the 175 amino acid variant, wherein the first amino acid is methionine and there is a threonine residue at Thr 134. SEQ ID NO:2 is a 174 amino acid variant which has the same sequence as the 175 amino acid variant execpt thet the leading methionine is missing, thus the sequence begins with T and there is a threonine residue at position 133.

FIG. 7 is a table providing exemplary sialyltransferases of use in forming the glycoconjugates of the invention, e.g., to glycoPEGylate peptides with a modified sialic acid.

DETAILED DESCRIPTION OF THE INVENTION AND THE PREFERRED EMBODIMENTS

Abbreviations

Figure 1A:
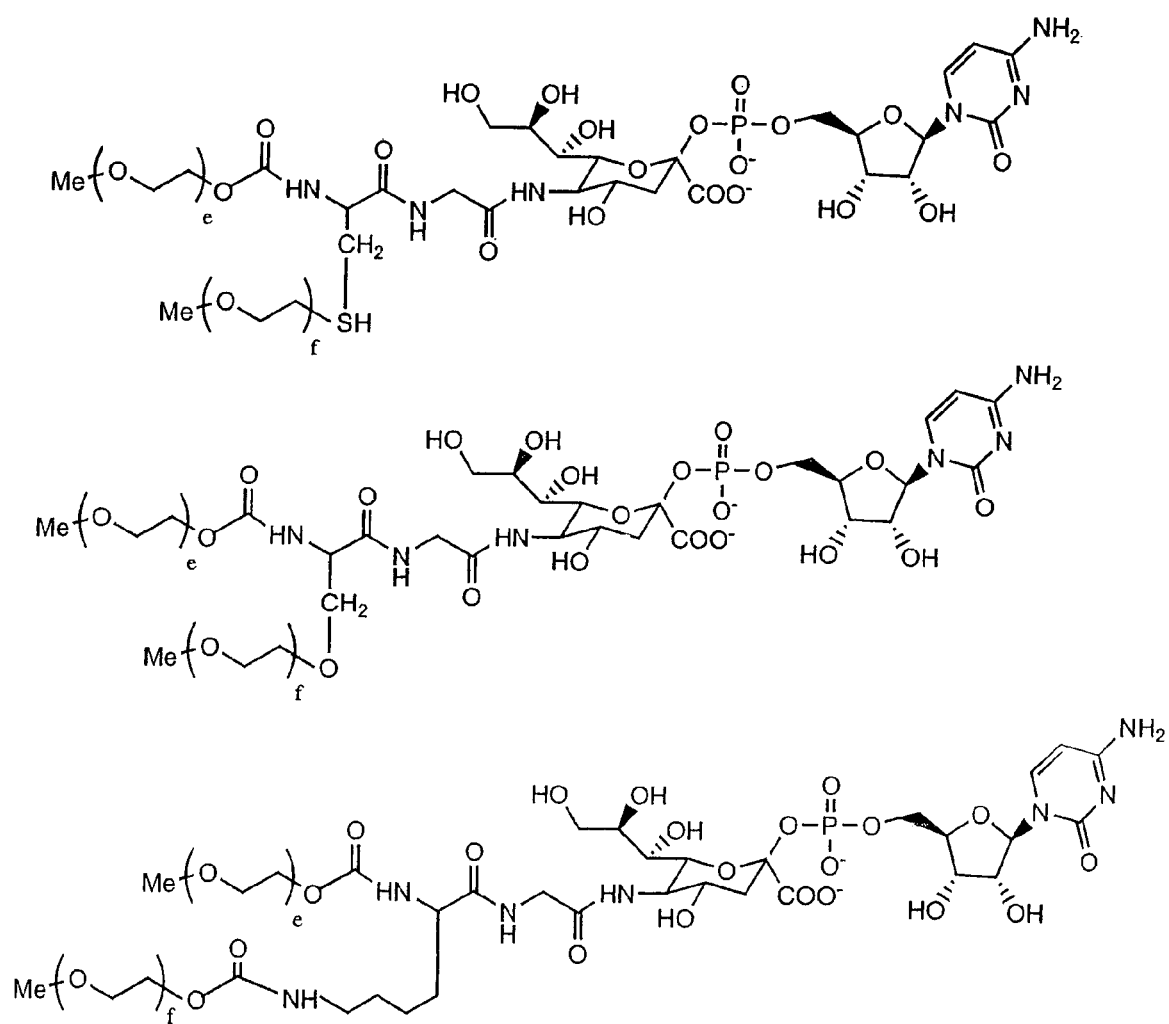
FIG. 1 illustrates exemplary modified sialic acid nucleotides useful in the practice of the invention. A. Structure of exemplary branched (e.g., 30 kDa, 40 kDa) CMP-sialic acid-PEG sugar nucleotides. B. Structure of linear CMP-sialic acid-PEG (e.g., 10 kDa).
Figure 1B:
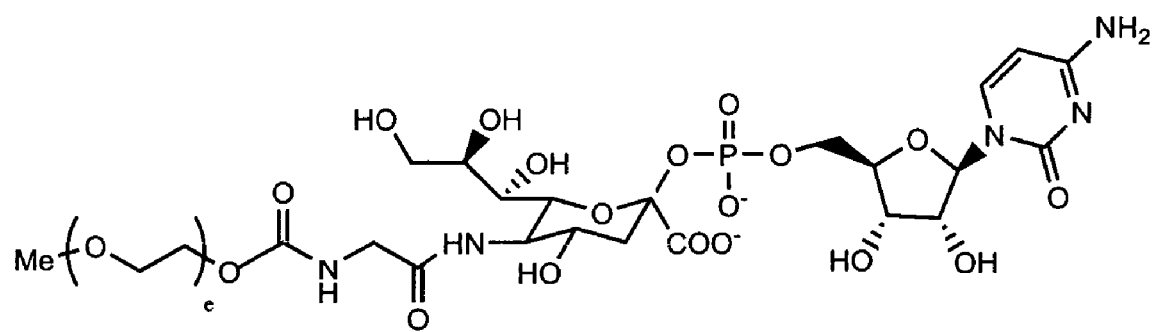
Figure 2:
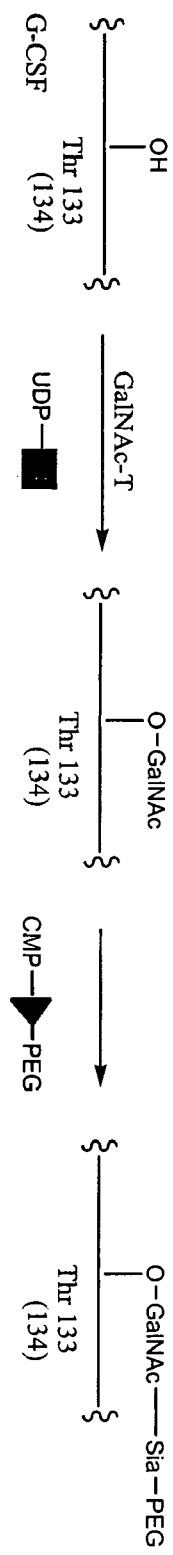
FIG. 2 is a scheme showing an exemplary embodiment of the invention in which a carbohydrate residue on a G-CSF peptide is remodeled by enzymatically adding a GalNAc moiety to the glycosyl residue at Thr 133 (Thr 134 when methionine is present) prior to adding a saccharyl moiety derivatized with PEG.
Figure 3:
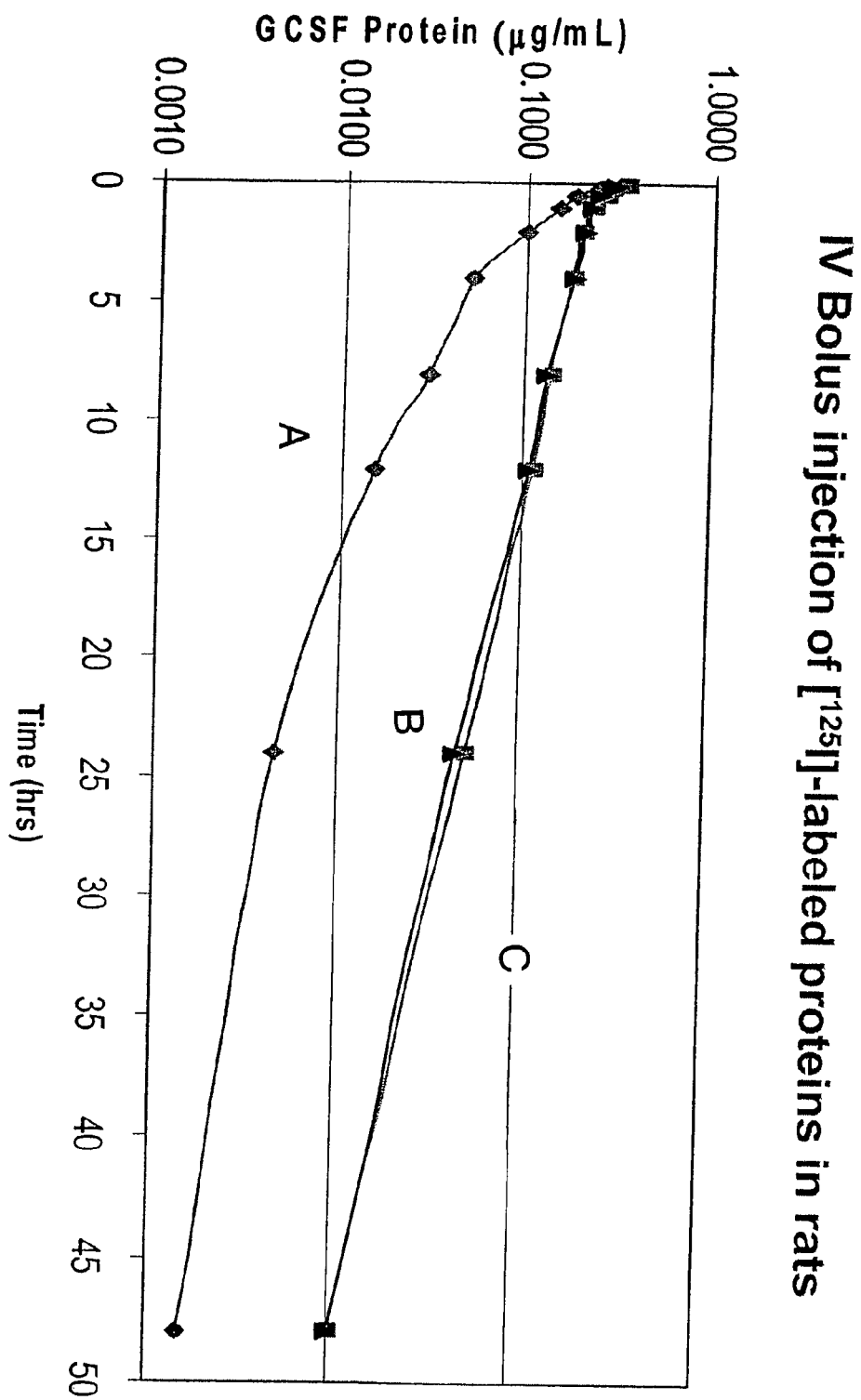
FIG. 3 is a plot comparing the in vivo residence lifetimes of unPEGylated G-CSF (A), chemically PEGylated G-CSF (B) and enzymatically glycopegylated G-CSF (C).
Figure 4:
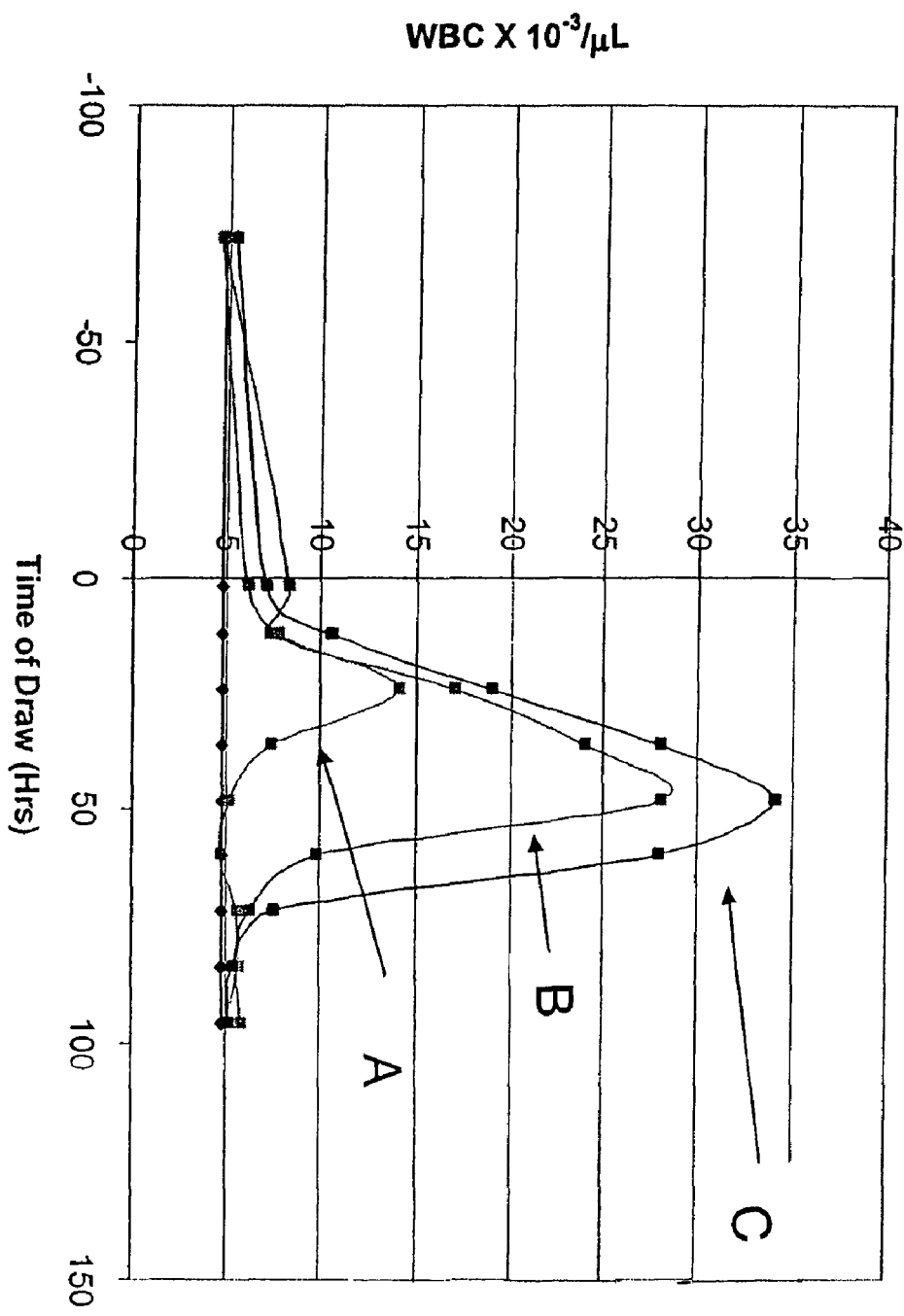
FIG. 4 is a plot comparing the activities of the species shown in FIG. 3.

PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; and NeuAc, sialyl (N-acetylneuraminyl); M6P, mannose-6-phosphate; Sia, sialic acid, N-acetylneuraminyl, and derivatives and analogues thereof.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature, see, *Essentials of Glycobiology* Varki et al. eds. CSHL Press (1999).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomirrietics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "peptide conjugate," refers to species of the invention in which a peptide is conjugated with a modified sugar as set forth herein.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, the term "modified sugar," refers to a naturally- or non-naturally-occurring carbohydrate that is enzymatically added onto an amino acid or a glycosyl residue of a peptide in a process of the invention. The modified sugar is selected from enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, PEG moieties, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol). Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol.

The central branch moiety can also be derived from several amino acids, such as lysine. The branched poly(ethylene glycol) can be represented in general form as R(-PEG-OH)$_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The "area under the curve" or "AUC", as used herein in the context of administering a peptide drug to a patient, is defined as total area under the curve that describes the concentration of drug in systemic circulation in the patient as a function of time from zero to infinity.

The term "half-life" or "t½", as used herein in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fticose. Slower beta phase clearance may occur via renal glomerular filtration for molecules with an effective radius <2 nm (approximately 68 kD) and/or specific or non-specific uptake and metabolism in tissues. GlycoPEGylation may cap terminal sugars (e.g., galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of glycoPEGylation on alpha phase and beta phase half-lives may vary depending upon the size, state of glycosylation, and other parameters, as is well known in the art. Further explanation of "half-life" is found in Pharmaceutical Biotechnology (1997, DFA Crommelin and R D Sindelar, eds., Harwood Publishers, Amsterdam, pp 101-120).

The term "glycoconjugation," as used herein, refers to the enzymatically mediated conjugation of a modified sugar species to an amino acid or glycosyl residue of a polypeptide, e.g., a G-CSF peptide of the present invention. A subgenus of "glycoconjugation" is "glyco-PEGylation," in which the modifying group of the modified sugar is poly(ethylene glycol), and alkyl derivative (e.g., m-PEG) or reactive derivative (e.g., H$_2$N-PEG, HOOC-PEG) thereof.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g, multivalent agents. Therapeutic moiety also includes proteins and constructs that include proteins. Exemplary proteins include, but are not limited to, Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, Vila, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering," means oral administration, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to" or a "therapeutically effective amount" or any grammatically equivalent term means the amount that, when administered to an animal for treating a disease, is sufficient to effect treatment for that disease.

The term "isolated" refers to a material that is substantially or essentially free from components, which are used to produce the material. For peptide conjugates of the invention, the term "isolated" refers to material that is substantially or essentially free from components which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a $\alpha 1,2$ fucosyltransferase, a substantially uniform fucosylation pattern exists if substantially all (as defined below) of the Gal$\beta$1,4-GlcNAc-R and sialylated analogues thereof are fucosylated in a peptide conjugate of the invention. In the fucosylated structures set forth herein, the Fuc-GlcNAc linkage is generally $\alpha 1,6$ or $\alpha 1,3$, with $\alpha 1,6$ generally preferred. It will be understood by one of skill in the art, that the starting material may contain glycosylated acceptor moieties (e.g., fucosylated Gal$\beta$1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g, —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRS$O_2$R", —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_u$—U—, wherein T and U are independently —NR—, —O—, —CRR'— or a single bond, and u is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_z$—X—(CR"R''')$_d$—, where z and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

As used herein, the term "heteroatom" is meant to include oxygen (O), nitrogen (N), sulfur (S) and silicon (Si).

Introduction

The present invention encompasses a method for the modification of the glycan structure on G-CSF. G-CSF is well known in the art as a cytokine produced by activated T-cells, macrophages, endothelial cells, and stromal fibroblasts. G-CSF primarily acts on the bone marrow to increase the production of inflammatory leukocytes, and further functions as an endocrine hormone to initiate the replenishment of neutrophils consumed during inflammatory functions. G-CSF also has clinical applications in bone marrow replacement following chemotherapy.

The present invention provides a conjugate of granulocyte colony stimulating factor (G-CSF). The invention provides conjugates of glycosylated and unglycosylated peptides having granulocyte colony stimulating activity. The conjugates may be additionally modified by further conjugation with diverse species such as therapeutic moieties, diagnostic moieties, targeting moieties and the like.

The present invention further includes a method for remodeling and/or modifying G-CSF. G-CSF is a valuable tool in treatment of numerous diseases, but as stated above, its clinical efficacy has been hampered by its relatively poor pharmacokinetics In exemplary embodiments, a G-CSF peptide of the invention may be administered to patients for the purposed of preventing infection in cancer patients undergoing certain types of radiation therapy, chemotherapy, and bone marrow transplantations, to mobilize progenitor cells for collection in peripheral blood progenitor cell transplantations, for treatment of severe chronic or relative leukopenia, irrespective of cause, and to support treatment of patients with acute myeloid leukaemia. Additionally, the polypeptide conjugate or composition of the invention may be used for treatment of AIDS or other immunodeficiency diseases as well as bacterial infections.

G-CSF has been cloned and sequenced. In an exemplary embodiment, G-CSF has an the amino acid sequence according to SEQ. ID NO:1 or SEQ. ID NO:2. The skilled artisan will readily appreciate that the present invention is not limited to the sequences depicted herein, as variants of G-CSF, as discussed hereinabove.

Thus, the present invention further encompasses G-CSF variants, as well known in the art. As an example, but in no way meant to be limiting to the present invention, a G-CSF variant has been described in U.S. Pat. No. 6,166,183, in which a G-CSF comprising the natural complement of lysine residues and further linked to one or two polyethylene glycol molecules is described. Additionally, U.S. Pat. Nos. 6,004, 548, 5,580,755, 5,582,823, and 5,676,941 describe a G-CSF variant in which one or more of the cysteine residues at position 17, 36, 42, 64, and 74 are replaced by alanine or alternatively serine. U.S. Pat. No. 5,416,195 describes a G-CSF molecule in which the cysteine at position 17, the aspartic acid at position 27, and the serines at positions 65 and 66 are substituted with serine, serine, proline, and proline, respectively. Other variants are well known in the art, and are described in, for example, U.S. Pat. No. 5,399,345. Still further variants have an amino acid selected from SEQ ID Nos: 3-11.

The expression and activity of a modified G-CSF molecule of the present invention can be assayed using methods well known in the art, and as described in, for example, U.S. Pat. No. 4,810,643. As an example, activity can be measured using radio-labeled thymidine uptake assays. Briefly, human bone marrow from healthy donors is subjected to a density cut with Ficoll-Hypaque (1.077 g/mL, Pharmacia, Piscataway, N.J.) and low density cells are suspended in Iscove's medium (GIBCO, La Jolla, Calif.) containing 10% fetal bovine serum, glutamine and antibiotics. About $2 \times 10^4$ human bone marrow cells are incubated with either control medium or the G-CSF or the present invention in 96-well flat bottom plates at about 37° C. in 5% $CO_2$ in air for about 2 days. Cultures are then pulsed for about 4 hours with 0.5 μCi/well of $^3$H-thymidine (New England Nuclear, Boston, Mass.) and uptake is measured as described in, for example, Ventua, et al.(1983, Blood 61:781). An increase in $^3$H-thymidine incorporation into human bone marrow cells as compared to bone marrow cells treated with a control compound is an indication of a active and viable G-CSF compound.

As discussed above, the conjugates of the invention are formed by the enzymatic attachment of a modified sugar to the glycosylated or unglycosylated G-CSF peptide. The modified sugar, when interposed between the G-CSF peptide and the modifying group on the sugar becomes what may be referred to herein e.g., as an "intact glycosyl linking group." Using the exquisite selectivity of enzymes, such as glycosyltransferases, the present method provides peptides that bear a desired group at one or more specific locations. Thus, according to the present invention, a modified sugar is attached directly to a selected locus on the G-CSF peptide chain or, alternatively, the modified sugar is appended onto a carbohydrate moiety of a glycopeptide. Peptides in which modified sugars are bound to both a glycopeptide carbohydrate and directly to an amino acid residue of the G-CSF peptide backbone are also within the scope of the present invention.

In contrast to known chemical and enzymatic peptide elaboration strategies, the methods of the invention, make it possible to assemble peptides and glycopeptides that have a substantially homogeneous derivatization pattern; the enzymes used in the invention are generally selective for a particular amino acid residue or combination of amino acid residues of the G-CSF peptide. The methods are also practical for large-scale production of modified peptides and glycopeptides. Thus, the methods of the invention provide a practical means for large-scale preparation of glycopeptides having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fungal cells, yeast cells, or prokaryotic cells) or transgenic plants or animals.

The present invention also provides conjugates of glycosylated and unglycosylated G-CSF peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent.

The Conjugates

In a first aspect, the present invention provides a conjugate between a selected modifying group and a G-CSF peptide.

The link between the peptide and the modifying moiety includes a glycosyl linking group interposed between the peptide and the selected moiety. As discussed herein, the selected modifying moiety is essentially any species that can be attached to a saccharide unit, resulting in a "modified sugar" that is recognized by an appropriate transferase enzyme, which appends the modified sugar onto the peptide, or a glycosyl residue attached thereto. The saccharide component of the modified sugar, when interposed between the peptide and a selected moiety, becomes a "glycosyl linking group," e.g., an "intact glycosyl linking group." The glycosyl linking group is formed from any mono- or oligo-saccharide that, after modification with the modifying group, is a substrate for an enzyme that adds the modified sugar to an amino acid or glycosyl residue of a peptide.

The glycosyl linking group can be, or can include, a saccharide moiety that is degradatively modified before or during the addition of the modifying group. For example, the glycosyl linking group can be derived from a saccharide residue that is produced by oxidative degradation of an intact saccharide to the corresponding aldehyde, e.g., via the action of metaperiodate, and subsequently converted to a Schiff base with an appropriate amine, which is then reduced to the corresponding amine.

The conjugates of the invention will typically correspond to the general structure:

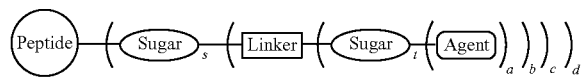

in which the symbols a, b, c, d and s represent a positive, non-zero integer; and t is either 0 or a positive integer. The "agent" is a therapeutic agent, a bioactive agent, a detectable label, water-soluble moiety (e.g., PEG, m-PEG, PPG, and m-PPG) or the like. The "agent" can be a peptide, e.g., enzyme, antibody, antigen, etc. The linker can be any of a wide array of linking groups, infra. Alternatively, the linker may be a single bond or a "zero order linker."

In an exemplary embodiment, the selected modifying group is a water-soluble polymer, e.g., m-PEG. The water-soluble polymer is covalently attached to the peptide via a glycosyl linking group. The glycosyl linking group is covalently attached to an amino acid residue or a glycosyl residue of the peptide. The invention also provides conjugates in which an amino acid residue and a glycosyl residue are modified with a glycosyl linking group.

An exemplary water-soluble polymer is poly(ethylene glycol), e.g., methoxy-poly(ethylene glycol). The poly(ethylene glycol) used in the present invention is not restricted to any particular form or molecular weight range. For unbranched poly(ethylene glycol) molecules the molecular weight is preferably between 500 and 100,000. A molecular weight of 2000-60,000 is preferably used and preferably of from about 5,000 to about 30,000.

In another embodiment the poly(ethylene glycol) is a branched PEG having more than one PEG moiety attached. Examples of branched PEGs are described in U.S. Pat. Nos. 5,932,462; 5,342,940; 5,643,575; 5,919,455; 6,113,906; 5,183,660; WO 02/09766; Kodera Y., *Bioconjugate Chemistry* 5: 283-288 (1994); and Yamasaki et al., *Agric. Biol. Chem.*, 52: 2125-2127, 1998. In a preferred embodiment the molecular weight of each poly(ethylene glycol) of the branched PEG is less than or equal to 40,000 daltons.

In addition to providing conjugates that are formed through an enzymatically added glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to a structurally identical amino acid or glycosyl residue. Thus, in a second aspect, the invention provides a peptide conjugate having a population of water-soluble polymer moieties, which are covalently bound to the peptide through a glycosyl linking group, e.g., an intact glycosyl linking group. In a preferred conjugate of the invention, essentially each member of the population is bound via the glycosyl linking group to a glycosyl residue of the peptide, and each glycosyl residue of the peptide to which the glycosyl linking group is attached has the same structure.

Also provided is a peptide conjugate having a population of water-soluble polymer moieties covalently bound thereto through a glycosyl linking group. In a preferred embodiment, essentially every member of the population of water soluble polymer moieties is bound to an amino acid residue of the peptide via a glycosyl linking group, and each amino acid residue having a glycosyl linking group attached thereto has the same structure.

The present invention also provides conjugates analogous to those described above in which the peptide is conjugated to a therapeutic moiety, diagnostic moiety, targeting moiety, toxin moiety or the like via an intact glycosyl linking group. Each of the above-recited moieties can be a small molecule, natural polymer (e.g., polypeptide) or synthetic polymer. When the modifying moiety is attached to a sialic acid, it is generally preferred that the modifying moiety is substantially non-fluorescent.

Essentially any Granulocyte Colony Stimulating Factor peptide or agent, having any sequence, is of use as the peptide component of the conjugates of the present invention. Granulocyte Colony Stimulating Factor has been cloned and sequenced. In an exemplary embodiment, the G-CSF peptide has the sequence presented in SEQ ID NO:1:

```
                                              (SEQ ID NO: 1)
MTPLGPASSLPQSFLLKCLEQVRKIQGDGAALQEKLCATYK
LCHPEELVLLGHSLGIPWAPLSSCPSQALQLAGCLSQLHSGL
FLYQGLLQALEGISPELGPTLDTLQLDVADFATTIWQQMEE
LGMAPALQPTQGAMPAFASAFQRRAGGVLVASHLQSFLEV
SYRVLRHLAQP.
```

In another exemplary embodiment, the G-CSF peptide has the sequence presented in SEQ ID NO:2:

```
                                              (SEQ ID NO: 2)
TPLGPASSLPQSFLLKCLEQVRKIQGDGAALQEKLCATYKL
CHPEELVLLGHSLGIPWAPLSSCPSQALQLAGCLSQLHSGLF
LYQGLLQALEGISPELGPTLDTLQLDVADFATTIWQQMEEL
GMAPALQPTQGAMPAFASAFQRRAGGVLVASHLQSFLEVS
YRVLRHLAQP.
```

In other exemplary embodiments, the G-CSF peptide has a sequence presented in SEQ ID Nos: 3-11, below.

```
                                              (SEQ ID NO: 3)
MTPLGPASSLPQSFLLKCLEQVRKIQGDGAALQEKLVSECA
TYKLCHPEELVLLGHSLGIPWAPLSSCPSQALQLAGCLSQL
HSGLFLYQGLLQALEGISPELGPTLDTLQLDVADFATTIWQ
QMEELGMAPALQPTQGAMPAFASAFQRRAGGVLVASHLQ
SFLEVSYRVLRHLAQP (SEQ ID NO: 4)
MAGPATQSPMKLMALQLLLWHSALWTVQEATPLGPASSL
PQSFLLKCLEQVRKIQGDGAALQEKLCATYKLCHPEELVLL
GHSLGIPWAPLSSCPSQALQLAGCLSQLHSGLFLYQGLLQA
LEGISPELGPTLDTLQLDVADFATTIWQQMEELGMAPALQP
TQGAMPAFASAFQRRAGGVLVASHLQSFLEVSYRVLRHLA
QP (SEQ ID NO: 5)
MAGPATQSPMKLMALQLLLWHSALWTVQEATPLGPASSL
PQSFLLKCLEQVRKIQGDGAALQEKLVSECATYKLCHPEEL
VLLGHSLGIPWAPLSSCPSQALQLAGCLSQLHSGLFLYQGL
LQALEGISPELGPTLDTLQLDVADFATTIWQQMEELGMAPA
LQPTQGAMPAFASAFQRRAGGVLVASHLQSFLEVSYRVLR
HLAQP (SEQ ID NO: 6)
MVTPLGPASSLPQSFLLKCLEQVRKIQGDGAALQEKLCATY
KLCHPEELVLLGHTLGIPWAPLSSCPSQALQLAGCLSQLHS
GLFLYQGLLQALEGISPELGPTLDTLQLDVADFATTIWQQM
EELGMAPALQPTQGAMPAFASAFQRRAGGVLVASHLQSFL
EVSYRVLRHLAQP;

(SEQ ID NO: 7)
MTPLGPASSLPQSFLLKCLEQVRKIQGDGAALQEKLCATYK
LCHPEELVLLGHTLGIPWAPLSSCPSQALQLAGCLSQLHSGL
FLYQGLLQALEGISPELGPTLDTLQLDVADFATTIWQQMEE
LGMAPALQPTQGAMPAFASAFQRRAGGVLVASHLQSFLEV
SYRVLRHLAQP;

(SEQ ID NO: 8)
MVTPLGPASSLPQSFLLKCLEQVRKIQGDGAALQEKLCATY
KLCHPEELVLLGSSLGIPWAPLSSCPSQALQLAGCLSQLHSG
LFLYQGLLQALEGISPELGPTLDTLQLDVADFATTIWQQME
ELGMAPALQPTQGAMPAFASAFQRRAGGVLVASHLQSFLE
VSYRVLRHLAQP;

(SEQ ID NO: 9)
MQTPLGPASSLPQSFLLKCLEQVRKIQGDGAALQEKLCATY
KLCHPEELVLLGHSLGIPWAPLSSCPSQALQLAGCLSQLHS
GLFLYQGLLQALEGISPELGPTLDTLQLDVADFATTIWQQM
EELGMAPALQPTQGAMPAFASAFQRRAGGVLVASHLQSFL
EVSYRVLRHLAQP;

(SEQ ID NO: 10)
MTPLGPASSLPQSFLLKCLEQVRKIQGDGAALQEKLCATYK
LCHPEELVLLGHSLGIPWAPLSSCPSQALQLAGCLSQLHSGL
FLYQGLLQALEGISPELGPTLDTLQLDVADFATTIWQQMEE
LGMAPALQPTQGAMPAFASAFQRRAGGVLVASHLQSFLEV
SYRVLRHLAQPTQGAMP;;
and (SEQ ID NO: 11)
MTPLGPASSLPQSFLLKCLEQVRKIQGDGAALQEKLCATYK
LCHPEELVLLGSSLGIPWAPLSSCPSQALQLAGCLSQLHSGL
FLYQGLLQALEGISPELGPTLDTLQLDVADFATTIWQQMEE
LGMAPTTTPTQTAMPAFASAFQRRAGGVLVASHLQSFLEV
SYRVLRHLAQP
```

The present invention is in no way limited to the sequences set forth herein. Use of G-CSF peptides of other sequences that are mutated to increase or decrease a property or modify a structural feature of the peptide are within the scope of the invention. For example, mutant G-CSF peptides of use in the invention include those that are provided with additional O-glycosylation sites or such sites at other positions. Moreover, mutant peptides that include one or more N-glycosylation site are of use in the invention.

Preferably, neither the amino nor the carboxy terminus of the G-CSF peptide is derivatized with a polymeric modifying moiety.

The peptides of the invention include at least one O-linked or N-linked glycosylation site, which is glycosylated with a glycosyl residue that includes a polymeric modifying moiety, e.g., a PEG moiety. In an exemplary embodiment, the PEG is covalently attached to the peptide via an intact glycosyl linking group. The glycosyl linking group is covalently attached to either an amino acid residue or a glycosyl residue of the peptide. Alternatively, the glycosyl linking group is attached to one or more glycosyl units of a glycopeptide. The invention also provides conjugates in which a glycosyl linking group is attached to both an amino acid residue and a glycosyl residue.

The PEG moiety is attached to an intact glycosyl linker directly, or via a non-glycosyl linker, e.g., substituted or unsubstituted alkyl, substituted or unsubstituted heteroalkyl.

In an exemplary embodiment, the invention utilizes a modified sugar amine that has the formula:

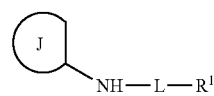

in which J is a glycosyl moiety (e.g., a nucleotide sugar), L is a bond or a linker and $R^1$ is the modifying group, e.g., a polymeric modifying moiety. Exemplary bonds are those that are formed between an NH₂ moiety on the glycosyl moiety and a group of complementary reactivity on the modifying group. For example, when $R^1$ includes a carboxylic acid moiety, this moiety may be activated and coupled with the NH₂ moiety on the glycosyl residue affording a bond having the structure NHC(O)$R^1$. J is preferably a glycosyl moiety that is "intact", not having been degraded by exposure to conditions that cleave the pyranose or furanose structure, e.g. oxidative conditions, e.g., sodium periodate.

Exemplary linkers include alkyl and heteroalkyl moieties. The linkers include linking groups, for example acyl-based linking groups, e.g., —C(O)NH—, —OC(O)NH—, and the like. The linking groups are bonds formed between components of the species of the invention, e.g., between the glycosyl moiety and the linker (L), or between the linker and the modifying group ($R^1$). Other exemplary linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate of the modifying group.

Another exemplary linker is a PEG moiety, e.g., a PEG moiety that is functionalized with an amino acid residue. The PEG linker is conjugated to the glycosyl group through the amino acid residue at one PEG terminus and bound to $R^1$ through the other PEG terminus. Alternatively, the amino acid residue is bound to $R^1$ and the PEG terminus, which is not bound to the amino acid, is -bound to the glycosyl group.

An exemplary species of NH-L-$R^1$ has the formula: —NH{C(O)(CH₂)$_a$NH}$_s${C(O)(CH₂)$_b$(OCH₂CH₂)$_c$O (CH₂)$_d$ NH}$_t$$R^1$, in which the indices s and t are independently 0 or 1. The indices a, b and d are independently integers from 0 to 20, and c is an integer from 1 to 2500. Other similar linkers are based on species in which an —NH moiety is replaced by another group, for example, —S, —O or —CH₂. As those of skill will appreciate one or more of the bracketed moieties corresponding to indices s and t can be replaced with a substituted or unsubstituted alkyl or heteroalkyl moiety.

More particularly, the invention utilizes compounds in which NH-L-$R^1$ is: NHC(O)(CH₂)$_a$NHC(O)(CH₂)$_b$ (OCH₂CH₂)$_c$O(CH₂)$_d$NHR$^1$, NHC(O)(CH₂)$_b$(OCH₂CH₂)$_c$ O(CH₂)$_d$NHR$^1$, NHC(O)O(CH₂)$_b$(OCH₂CH₂)$_c$O(CH₂)$_d$ NHR$^1$, NH(CH₂)$_a$NHC(O)(CH₂)$_b$(OCH₂CH₂)$_c$O(CH₂)$_d$ NHR$^1$, NHC(O)(CH₂)$_a$NHR$^1$, NH(CH₂)$_a$NHR$^1$, and NHR$^1$. In these formulae, the indices a, b and d are independently selected from the integers from 0 to 20, preferably from 1 to 5. The index c is an integer from 1 to about 2500.

In an exemplary embodiment, c is selected such that the PEG moiety is approximately 1 kD, 5 kD, 10, kD, 15 kD, 20 kD or 30 kD.

In the discussion that follows, the invention is illustrated by reference to the use of selected derivatives of furanose and pyranose. Those of skill in the art will recognize that the focus of the discussion is for clarity of illustration and that the structures and compositions set forth are generally applicable across the genus of saccharide groups, modified saccharide groups, activated modified saccharide groups and conjugates of modified saccharide groups.

In an exemplary embodiment, the invention provides a glycopeptide that is conjugated to a polymeric modifying moiety through an intact glycosyl linking group having a formula that is selected from:

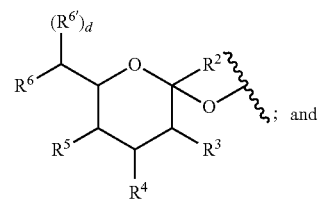

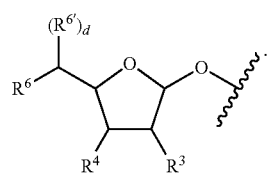

In Formulae I $R^2$ is H, CH₂O$R^7$, COO$R^7$ or O$R^7$, in which $R^7$ represents H, substituted or unsubstituted alkyl or substituted or unsubstituted heteroalkyl. When COO$R^7$ is a carboxylic acid or carboxylate, both forms are represented by the designation of the single structure COO⁻ or COOH. In Formulae I and II, the symbols $R^3$, $R^4$, $R^5$, $R^6$ and $R^{6'}$ independently represent H, substituted or unsubstituted alkyl, O$R^8$, NHC(O) $R^9$. The index d is 0 or 1. $R^8$ and $R^9$ are independently selected from H, substituted or unsubstituted alkyl, substituted or unsubstituted heteroalkyl, sialic acid or polysialic acid. At least one of $R^3$, $R^4$, $R^5$, $R^6$ or $R^{6'}$ includes the polymeric modifying moiety e.g., PEG, linked through a bond or a linking group. In an exemplary embodiment, $R^6$ and $R^{6'}$, together with the carbon to which they are attached are components of the pyruvyl side chain of sialic acid. In a further exemplary embodiment, this side chain is functionalized with the polymeric modifying moiety. In another exemplary embodiment, $R^6$ and $R^{6'}$, together with the carbon to which they are attached are components of the side chain of sialic acid and the polymeric modifying moiety is a component of $R^5$.

In a further exemplary embodiment, the polymeric modifying moiety is bound to the sugar core, generally through a heteroatom, e.g, nitrogen, on the core through a linker, L, as shown below:

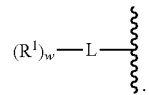

$R^1$ is the polymeric moiety and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety.

An exemplary compound according to the invention has a structure according to Formulae I or II, in which at least one of $R^2$, $R^3$, $R^4$, $R^5$, $R^6$ or $R^{6'}$ has the formula:

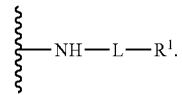

In another example according to this embodiment at least one of $R^2$, $R^3$, $R^4$, $R^5$, $R^6$ or $R^{6'}$ has the formula:

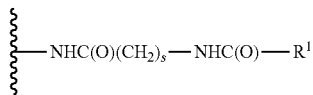

in which s is an integer from 0 to 20 and $R^1$ is a linear polymeric modifying moiety.

In an exemplary embodiment, the polymeric modifying moiety-linker construct is a branched structure that includes two or more polymeric chains attached to central moiety. In this embodiment, the construct has the formula:

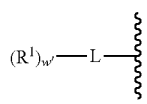

in which $R^1$ and L are as discussed above and w' is an integer from 2 to 6, preferably from 2 to 4 and more preferably from 2 to 3.

When L is a bond it is formed between a reactive functional group on a precursor of $R^1$ and a reactive functional group of complementary reactivity on the saccharyl core. When L is a non-zero order linker, a precursor of L can be in place on the glycosyl moiety prior to reaction with the $R^1$ precursor. Alternatively, the precursors of $R^1$ and L can be incorporated into a preformed cassette that is subsequently attached to the glycosyl moiety. As set forth herein, the selection and preparation of precursors with appropriate reactive functional groups is within the ability of those skilled in the art. Moreover, coupling the precursors proceeds by chemistry that is well understood in the art.

In an exemplary embodiment, L is a linking group that is formed from an amino acid, or small peptide (e.g., 1-4 amino acid residues) providing a modified sugar in which the polymeric modifying moiety is attached through a substituted alkyl linker. Exemplary linkers include glycine, lysine, serine and cysteine. The PEG moiety can be attached to the amine moiety of the linker through an amide or urethane bond. The PEG is linked to the sulfur or oxygen atoms of cysteine and serine through thioether or ether bonds, respectively.

In an exemplary embodiment, $R^5$ includes the polymeric modifying moiety. In another exemplary embodiment, $R^5$ includes both the polymeric modifying moiety and a linker, L, joining the modifying moiety to the remainder of the molecule. As discussed above, L can be a linear or branched structure. Similarly, the polymeric modifying can be branched or linear.

In one embodiment, the present invention provides an G-CSF peptide comprising the moiety:

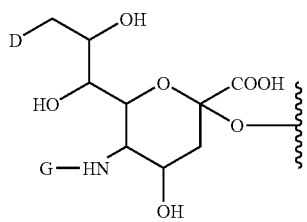

wherein D is a member selected from —OH and $R^1$-L-HN—; G is a member selected from H and $R^1$-L- and —C(O)($C_1$-$C_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is $R^1$-L-, and when G is —C(O)($C_1$-$C_6$)alkyl, D is $R^1$-L-NH—.

In another exemplary embodiment, the invention provides a conjugate formed between a modified sugar of the invention and a substrate G-CSF peptide. In this embodiment, the sugar moiety of the modified sugar becomes a glycosyl linking group interposed between the peptide substrate and the modifying group. An exemplary glycosyl linking group is an intact glycosyl linking group, in which the glycosyl moiety or moieties forming the linking group are not degraded by chemical (e.g., sodium metaperiodate) or enzymatic (e.g., oxidase) processes. Selected conjugates of the invention include a modifying group that is attached to the amine moiety of an amino-saccharide, e.g., mannosamine, glucosamine, galactosamine, sialic acid etc. Exemplary modifying group-intact glycosyl linking group cassettes according to this motif are based on a sialic acid structure, such as those having the formulae:

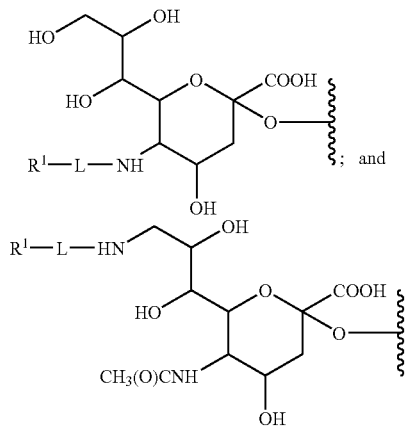

In the formulae above, $R^1$ and L are as described above. Further detail about the structure of exemplary $R^1$ groups is provided below.

In still a further exemplary embodiment, the conjugate is formed between a substrate G-CSF and a saccharyl moiety in which the modifying group is attached through a linker at the 6-carbon position of the saccharyl moiety. Thus, illustrative conjugates according to this embodiment have the formula:

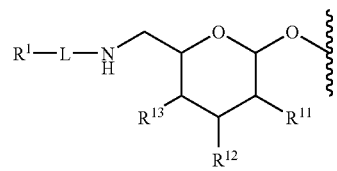

in which the radicals are as discussed above. Such saccharyl moieties include, without limitation, glucose, glucosamine, N-acetyl-glucosamine, galactose, galactosamine, N-acetyl-galactosamine, mannose, mannosamine, N-acetyl-mannosamine, and the like.

Due to the versatility of the methods available for modifying glycosyl residues on a therapeutic peptide such as G-CSF, the glycosyl structures on the peptide conjugates of the invention can have substantially any structure. Moreover, the glycans can be O-linked or N-linked. As exemplified in the discussion below, each of the pyranose and furanose derivatives discussed above can be a component of a glycosyl moiety of a peptide.

The invention provides a modified G-CSF peptide that includes a glycosyl group having the formula:

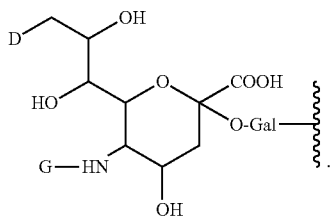

In other embodiments, the group has the formula:

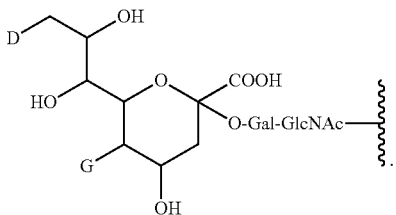

In a still further exemplary embodiment, the group has the formula:

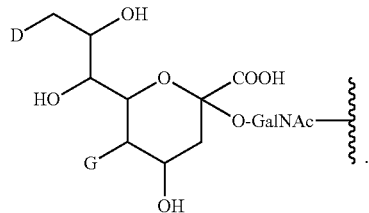

In yet another embodiment, the group has the formula:

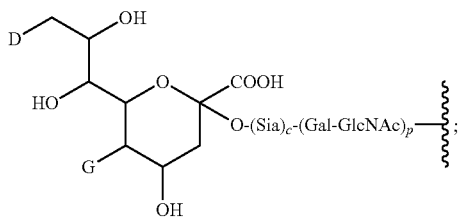

in which the index p represents and integer from 1 to 10; and c is either 0 or 1.

In an exemplary embodiment according to each of the formulae set forth above, the PEG-glycosyl linking group is attached at Thr 133 (Thr 134) of G-CSF.

In an exemplary embodiment, a glycoPEGylated G-CSF peptide of the invention includes at least one N-linked glycosyl residue selected from the glycosyl residues set forth below:

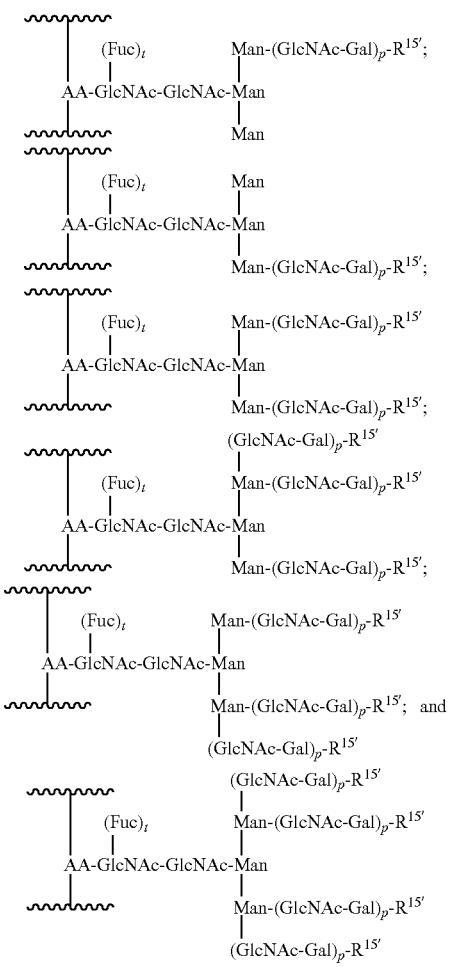

In the formulae above, the index t is 0 or 1 and the index p is an integer from 1 to 10. The symbol $R^{15'}$ represents H, OH (e.g., Gal-OH), a sialyl moiety, a polymer modified sialyl moiety (i.e., glycosyl linking group-polymeric modifying moiety (Sia-L-$R^1$)) or a sialyl moiety to which is bound a polymer modified sialyl moiety (e.g., Sia-Sia-L-$R^1$) ("Sia-Sia$^p$"). Exemplary polymer modified saccharyl moieties have a structure according to Formulae I and II. An exemplary G-CSF peptide of the invention will include at least one glycan having a $R^{15'}$ that includes a structure according to Formulae I or II. The oxygen, with the open valence, of Formulae I and II is preferably attached through a glycosidic linkage to a carbon of a Gal or GalNAc moiety. In a further exemplary embodiment, the oxygen is attached to the carbon at position 3 of a galactose residue. In an exemplary embodiment, the modified sialic acid is linked α2,3-to the galactose residue. In another exemplary embodiment, the sialic acid is linked α2,6-to the galactose residue.

In another exemplary embodiment, the invention provides an G-CSF peptide conjugate that includes a glycosyl linking group, such as those set forth above, that is covalently attached to an amino acid residue of the peptide. In one embodiment according to this motif, the glycosyl linking moiety is linked to a galactose residue through a Sia residue:

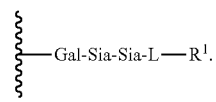

An exemplary species according to this motif is prepared by conjugating Sia-L-$R^1$ to a terminal sialic acid of a glycan using an enzyme that forms Sia-Sia bonds, e.g., CST-II, ST8Sia-II, ST8Sia-III and ST8Sia-IV.

In another exemplary embodiment, the glycans have a formula that is selected from the group:

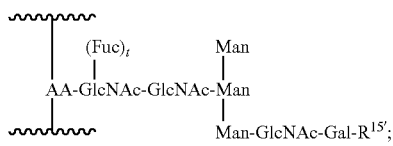

-continued

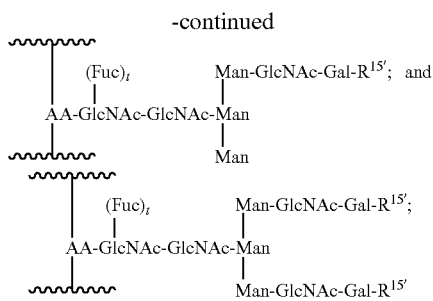

and combinations thereof.

The glycans of this group generally correspond to those found on an G-CSF peptide that is produced by insect (e.g., Sf-9) cells, following remodeling according to the methods set forth herein. For example insect-derived G-CSF that is expressed with a tri-mannosyl core is subsequently contacted with a GlcNAc donor and a GlcNAc transferase and a Gal donor and a Gal transferase. Appending GlcNAc and Gal to the tri-mannosyl core is accomplished in either two steps or a single step. A modified sialic acid is added to at least one branch of the glycosyl moiety as discussed herein. Those Gal moieties that are not functionalized with the modified sialic acid are optionally "capped" by reaction with a sialic acid donor in the presence of a sialyl transferase.

In an exemplary embodiment, at least 60% of terminal Gal moieties in a population of peptides is capped with sialic acid, preferably at least 70%, more preferably, at least 80%, still more preferably at least 90% and even more preferably at least 95%, 96%, 97%, 98% or 99% are capped with sialic acid.

In each of the formulae above, $R^{15}/R^{15'}$ is as discussed above. Moreover, an exemplary modified G-CSF peptide of the invention will include at least one glycan with an $R^{15}/R^{15'}$ moiety having a structure according to Formulae I or II.

In an exemplary embodiment, the glycosyl linking moiety has the formula:

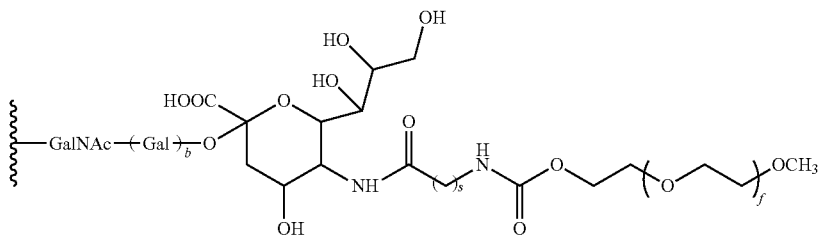

in which b is 0 or 1. The index s represents and integer from 1 to 10; and f represents and integer from 1 to 2500. Generally preferred is the use of a PEG moiety that has a molecular weight of about 20 kDa. Also preferred is the attachment of the glycosyl linking group to the threonine at 133 of SEQ. ID NO.: 1 or threonine 134 of SEQ. ID NO.: 2. In any of the O-linked structures of glycans herein, the GalNAc can be bound to a Sia.

In another exemplary embodiment, the G-CSF is derived from insect cells, remodeled by adding GlcNAc and Gal to the mannose core and glycopegylated using a sialic acid bearing a linear PEG moiety, affording an G-CSF peptide that comprises at least one moiety having the formula:

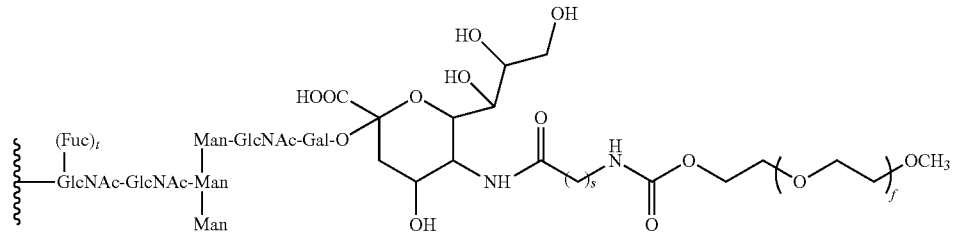

in which s represents and integer from 1 to 10; and f represents and integer from 1 to 2500.

As discussed herein, the PEG of use in the conjugates of the invention can be linear or branched. An exemplary precursor of use to form the branched conjugates according to this embodiment of the invention has the formula:

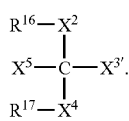

(III)

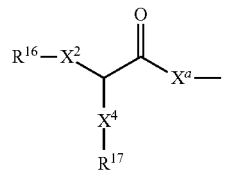

(IV)

The branched polymer species according to this formula are essentially pure water-soluble polymers. $X^{3'}$ is a moiety that includes an ionizable, e.g., OH, COOH, $H_2PO_4$, $HSO_3$, $HPO_3$, and salts thereof, etc.) or other reactive functional group, e.g., infra. C is carbon. $X^5$ is preferably a non-reactive group (e.g., H, unsubstituted alkyl, unsubstituted heteroalkyl), and can be a polymeric arm. $R^{16}$ and $R^{17}$ are independently selected polymeric arms, e.g., nonpeptidic, nonreactive polymeric arms (e.g., PEG)). $X^2$ and $X^4$ are linkage fragments that are preferably essentially non-reactive under physiological conditions, which may be the same or different. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join polymeric arms $R^{16}$ and $R^{17}$ to C. When $X^{3'}$ is reacted with a reactive functional group of complementary reactivity on a linker, sugar or linker-sugar cassette, $X^{3'}$ is converted to a component of linkage fragment $X^3$.

Exemplary linkage fragments for $X^2$, $X^3$ and $X^4$ are independently selected and include S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. In an exemplary embodiment, the linkage fragments $X^2$ and $X^4$ are different linkage fragments.

In an exemplary embodiment, the precursor (III), or an activated derivative thereof, is reacted with, and thereby bound to a sugar, an activated sugar or a sugar nucleotide through a reaction between $X^{3'}$ and a group of complementary reactivity on the sugar moiety, e.g., an amine. Alternatively, $X^{3'}$ reacts with a reactive functional group on a precursor to linker, L. One or more of $R^2$, $R^3$, $R^4$, $R^5$ $R^6$ or $R^{6'}$ of Formulae I and II can include the branched polymeric modifying moiety, or this moiety bound through L.

In an exemplary embodiment, the moiety:

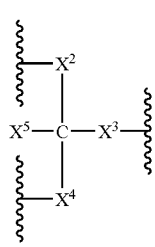

is the linker arm, L. In this embodiment, an exemplary linker is derived from a natural or unnatural amino acid, amino acid analogue or amino acid mimetic, or a small peptide formed from one or more such species. For example, certain branched polymers found in the compounds of the invention have the formula:

$X^a$ is a linkage fragment that is formed by the reaction of a reactive functional group, e.g., $X^{3'}$, on a precursor of the branched polymeric modifying moiety and a reactive functional group on the sugar moiety, or a precursor to a linker. For example, when $X^{3'}$ is a carboxylic acid, it can be activated and bound directly to an amine group pendent from an aminosaccharide (e.g., Sia, $GalNH_2$, $GlcNH_2$, $ManNH_2$, etc.), forming an $X^a$ that is an amide. Additional exemplary reactive functional groups and activated precursors are described hereinbelow. The index c represents an integer from 1 to 10. The other symbols have the same identity as those discussed above.

In another exemplary embodiment, $X^a$ is a linking moiety formed with another linker:

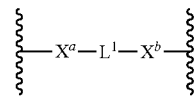

in which $X^b$ is a second linkage fragment and is independently selected from those groups set forth for $X^a$, and, similar to L, $L^1$ is a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), C(O)NH and NHC(O)O, and OC(O)NH.

In another exemplary embodiment, $X^4$ is a peptide bond to $R^{17}$, which is an amino acid, di-peptide (e.g., Lys-Lys) or tri-peptide (E.G., Lys-Lys-Lys) in which the alpha-amine moiety(ies) and/or side chain heteroatom(s) are modified with a polymeric modifying moiety.

In a further exemplary embodiment, the conjugates of the invention include a moiety, e.g., an $R^{15}/R^{15'}$ moiety that has a formula that is selected from:

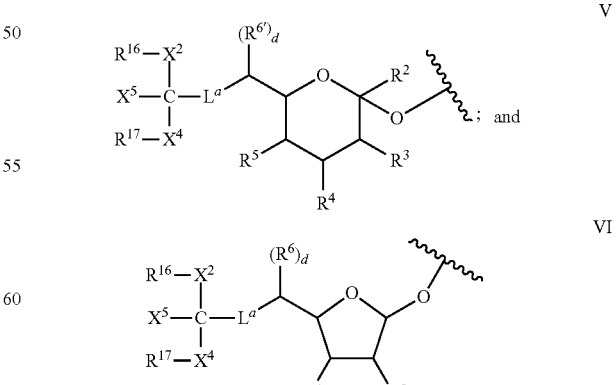

in which the identity of the radicals represented by the various symbols is the same as that discussed hereinabove. $L^a$ is a bond or a linker as discussed above for L and L¹, e.g., substituted or unsubstituted alkyl or substituted or unsubstituted heteroalkyl moiety. In an exemplary embodiment, $L^a$ is a moiety of the side chain of sialic acid that is functionalized with the polymeric modifying moiety as shown. Exemplary $L^a$ moieties include substituted or unsubstituted alkyl chains that include one or more OH or $NH_2$.

In yet another exemplary embodiment, the invention provides conjugates having a moiety, e.g., an $R^{15}/R^{15'}$ moiety with formula:

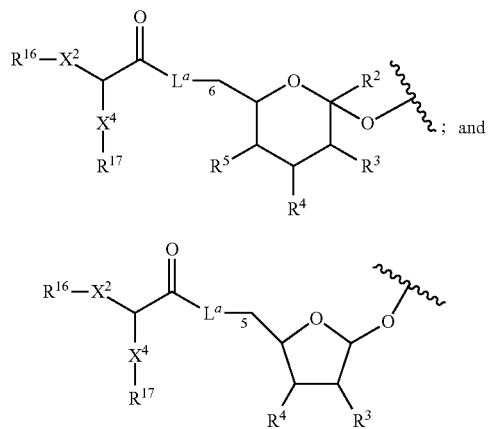

The identity of the radicals represented by the various symbols is the same as that discussed hereinabove. As those of skill will appreciate, the linker arm in Formulae VI and VII is equally applicable to other modified sugars set forth herein. In an exemplary embodiment, the species of Formulae VI and VII are the $R^{15}$ moieties attached to the glycan structures set forth herein.

In yet another exemplary embodiment, the G-CSF peptide includes an $R^{15'}$ moiety with the formula:

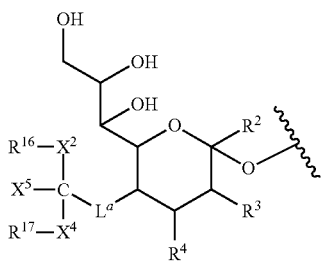

in which the identities of the radicals are as discussed above. An exemplary species for $L^a$ is $-(CH_2)_jC(O)NH(CH_2)_hC(O)NH-$, in which h and j are independently selected integers from 0 to 10. A further exemplary species is $-C(O)NH-$.

The embodiments of the invention set forth above are further exemplified by reference to species in which the polymer is a water-soluble polymer, particularly poly(ethylene glycol) ("PEG"), e.g., methoxy-poly(ethylene glycol). Those of skill will appreciate that the focus in the sections that follow is for clarity of illustration and the various motifs set forth using PEG as an exemplary polymer are equally applicable to species in which a polymer other than PEG is utilized.

PEG of any molecular weight, e.g., 1 kDa, 2 kDa, 5 kDa, 10 kDa, 15 kDa, 20 kDa, 30 kDa and 40 kDa is of use in the present invention.

In an exemplary embodiment, the $R^{15}$ moiety has a formula that is a member selected from the group:

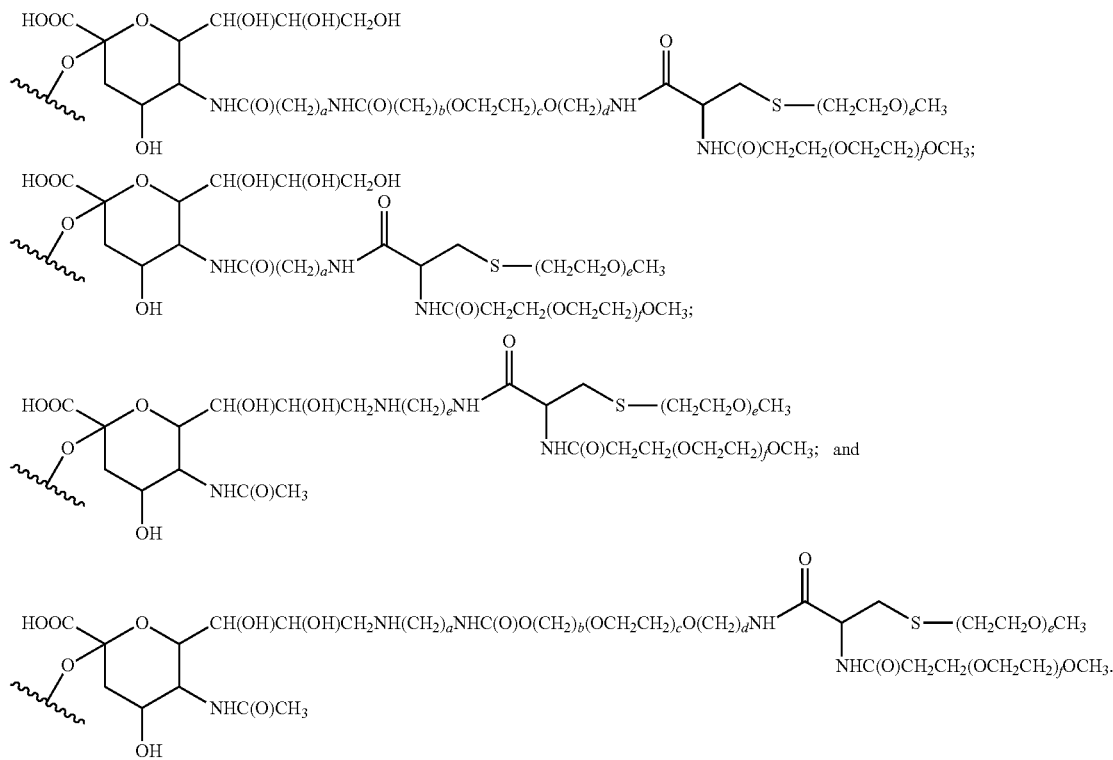

In each of the structures above, the linker fragment —NH(CH$_2$)$_a$— can be present or absent.

In other exemplary embodiments, the conjugate includes an R$^{15}$ moiety selected from the group:

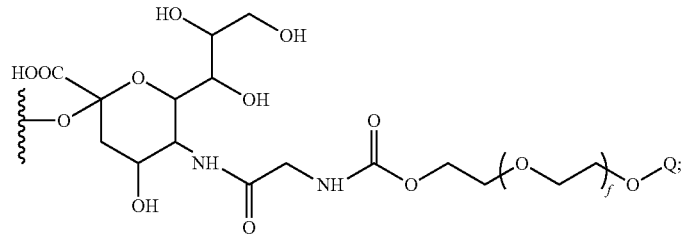

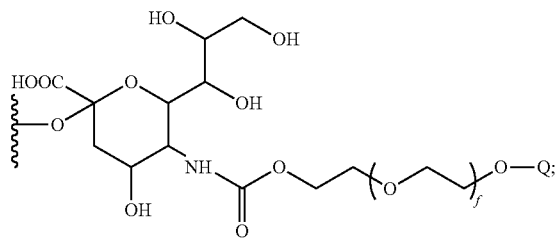

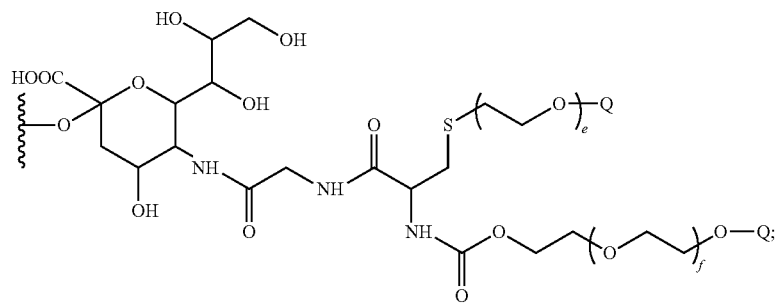

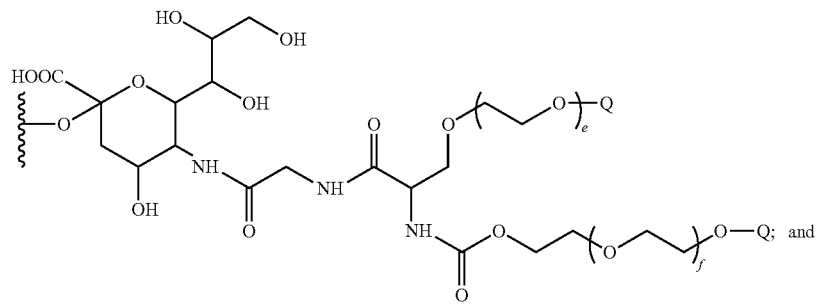

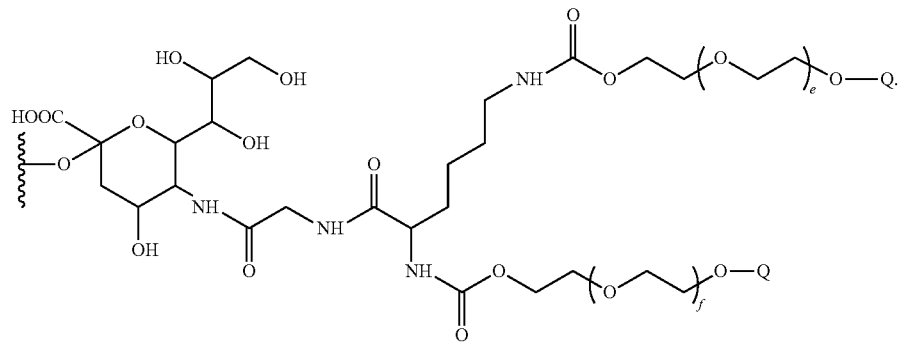

In each of the formulae above, the indices e and f are independently selected from the integers from 1 to 2500. In further exemplary embodiments, e and f are selected to provide a PEG moiety that is about 1 kD, 2 kD, 10 kD, 15 kD, 20 kD, 30 kD or 40 kD. The symbol Q represents substituted or unsubstituted alkyl (e.g., $C_1$-$C_6$ alkyl, e.g., methyl), substituted or unsubstituted heteroalkyl or H.

Other branched polymers have structures based on di-lysine (Lys-Lys) peptides, e.g.:

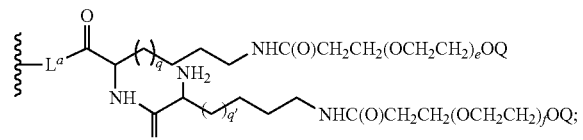

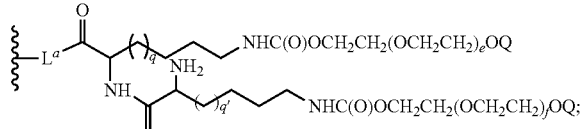

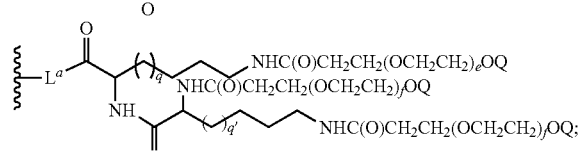

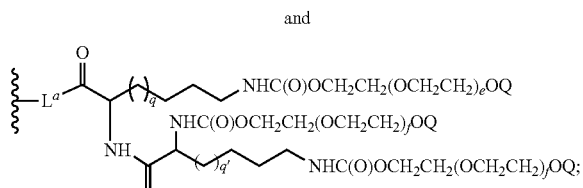

and tri-lysine peptides (Lys-Lys-Lys), e.g.:

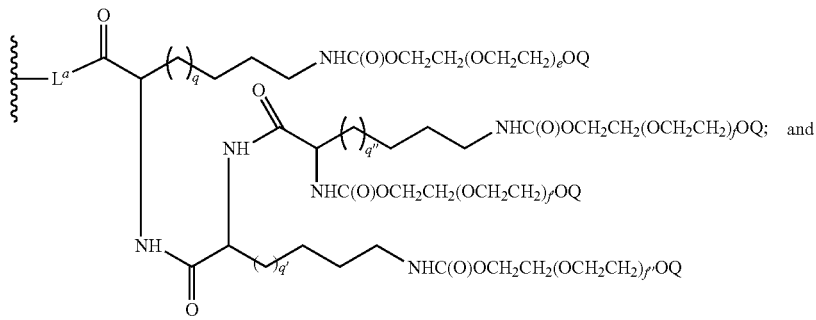

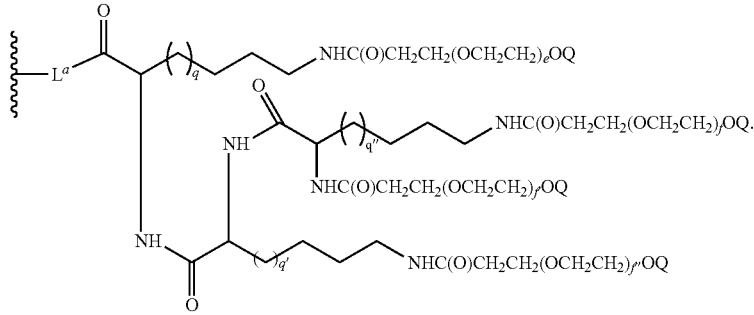

In each of the figures above, e, f, f' and f" represent integers independently selected from 1 to 2500. The indices q, q' and q" represent integers independently selected from 1 to 20.

In another exemplary embodiment, the G-CSF peptide comprises a glycosyl moiety selected from the formulae:

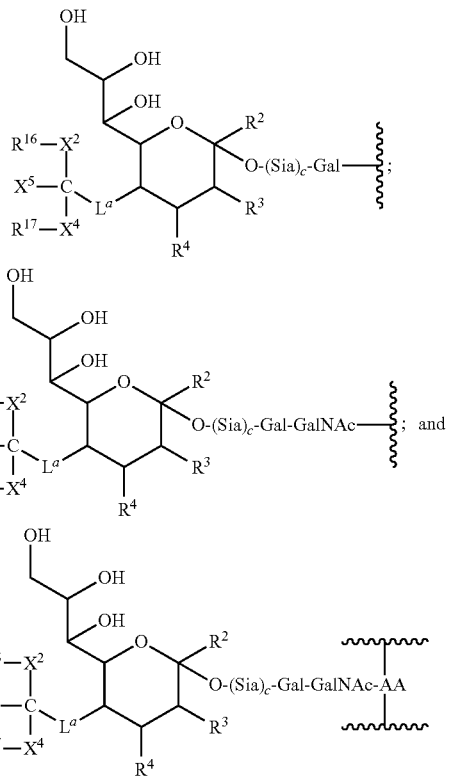

in which $L^a$ is a bond or a linker as described herein; the index t represents 0 or 1; and the index c represents 0 or 1. Each of these groups can be included as components of the mono-, bi-, tri- and tetra-antennary saccharide structures set forth above.

In yet another embodiment, the conjugates of the invention include a modified glycosyl residue that includes the substructure selected from:

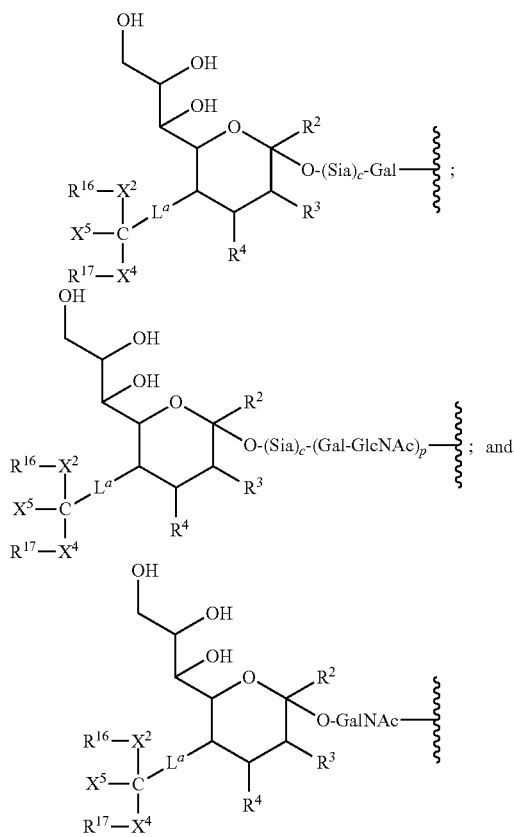

in which the index a and the linker $L^a$ are as discussed above. The index p is an integer from 1 to 10. The index c represents 0 or 1. Each of these groups can be included as components of the mono-, bi-, tri- and tetra-antennary saccharide structures set forth above.

In a further exemplary embodiment, the invention utilizes modified sugars in which the 6-hydroxyl position is converted to the corresponding amine moiety, which bears a linker-modifying group cassette such as those set forth above. Exemplary saccharyl groups that can be used as the core of these modified sugars include Gal, GalNAc, Glc, GlcNAc, Fuc, Xyl, Man, and the like. A representative modified sugar according to this embodiment has the formula:

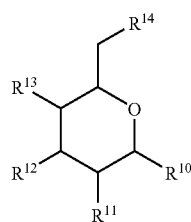

in which $R^{11}$-$R^{14}$ are members independently selected from H, OH, C(O)CH$_3$, NH, and NH C(O)CH$_3$. $R^{10}$ is a link to another glycosyl residue (—O-glycosyl) or to an amino acid of the G-CSF peptide (—NH—(G-CSF)). $R^{14}$ is OR$^1$, NHR$^1$ or NH-L-R$^1$. R$^1$ and NH-L-R$^1$ are as described above.

Selected conjugates according to this motif are based on mannose, galactose or glucose, or on species having the stereochemistry of mannose, galactose or glucose. The general formulae of these conjugates are:

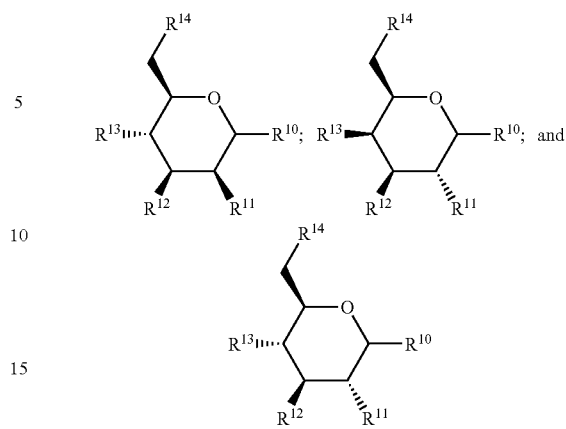

As discussed above, the invention provides saccharides bearing a modifying group, activated analogues of these species and conjugates formed between species such as peptides and lipids and a modified saccharide of the invention.

Modified Sugars

The present invention uses modified sugars and modified sugar nucleotides to form conjugates of the modified sugars. In modified sugar compounds of use in the invention, the sugar moiety is preferably a saccharide, a deoxy-saccharide, an amino-saccharide, or an N-acyl saccharide. The term "saccharide" and its equivalents, "saccharyl," "sugar," and "glycosyl" refer to monomers, dimers, oligomers and polymers. The sugar moiety is also functionalized with a modifying group. The modifying group is conjugated to the sugar moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any sugar can be utilized as the sugar core of the glycosyl linking group of the conjugates of the invention. Exemplary sugar cores that are useful in forming the compositions of the invention include, but are not limited to, glucose, galactose, mannose, fucose, and sialic acid. Other useful sugars include amino sugars such as glucosamine, galactosamine, mannosamine, the 5-amine analogue of sialic acid and the like. The sugar core can be a structure found in nature or it can be modified to provide a site for conjugating the modifying group. For example, in one embodiment, the invention provides a sialic acid derivative in which the 9-hydroxy moiety is replaced with an amine. The amine is readily derivatized with an activated analogue of a selected modifying group.

Exemplary modified sugars are modified with water-soluble or water-insoluble polymers. Examples of useful polymer are further exemplified below.

Water-Soluble Polymers

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly (amino acids), e.g., poly(aspartic acid) and poly(glutamic acid); nucleic acids; synthetic polymers (e.g., poly(acrylic acid), poly (ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie*, 57:5-29 (2002). Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly(ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly(ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

The modified sugars are prepared by reacting the glycosyl core (or a linker on the core) with a polymeric modifying moiety (or a linker on the polymeric modifying moiety). The discussion that follows provides examples of selected polymeric modifying moieties of use in the invention. For example, representative polymeric modifying moieties include structures that are based on side chain-containing amino acids, e.g., serine, cysteine, lysine, and small peptides, e.g., lys-lys. Exemplary structures include:

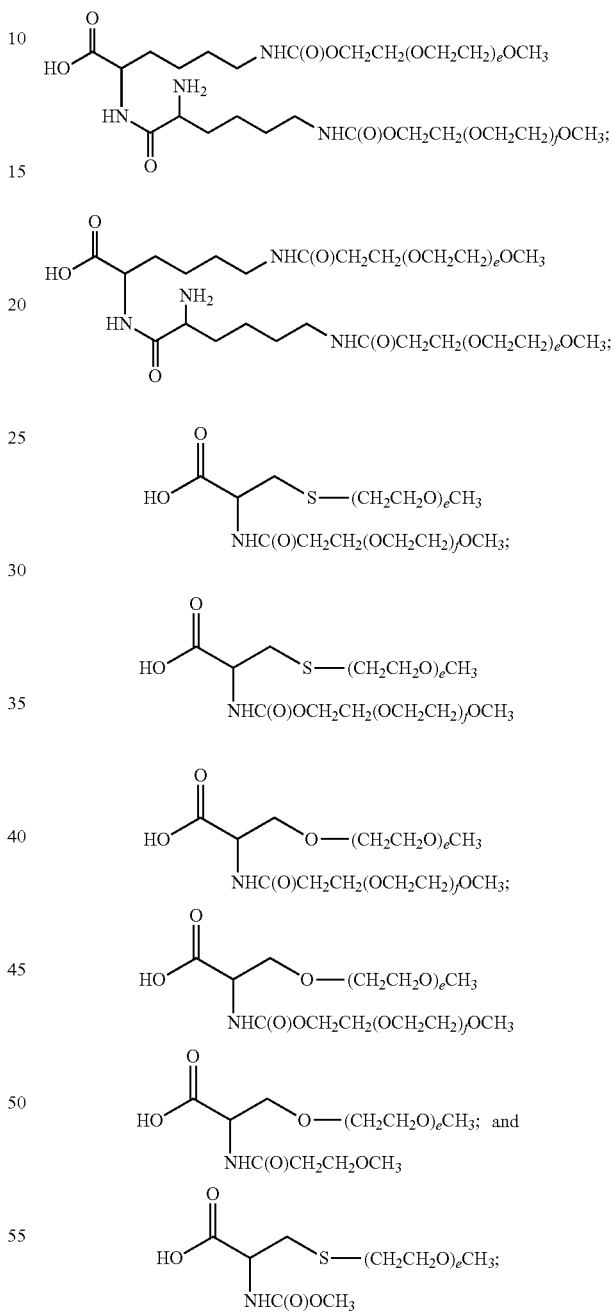

Those of skill will appreciate that the free amine in the di-lysine structures can also be pegylated through an amdie or urethane bond with a PEG moiety.

In yet another embodiment, the branched PEG moiety is based upon a tri-lysine peptide. The tri-lysine can be mono-, di-, tri-, or tetra-PEG-ylated. Exemplary species according to this embodiment have the formulae:

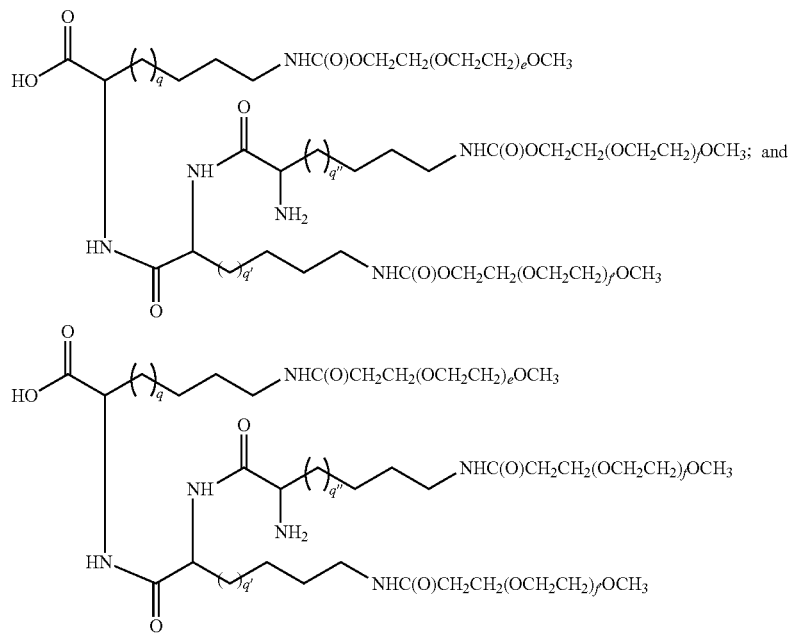

in which e, f and f' are independently selected integers from 1 to 2500; and q, q' and q" are independently selected integers from 1 to 20.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits labeled with the polymeric modifying moiety in a desired manner is within the scope of the invention.

The polymeric modifying moieties can be activated for reaction with the glycosyl core. Exemplary structures of activated species (e.g., carbonates and active esters) include:

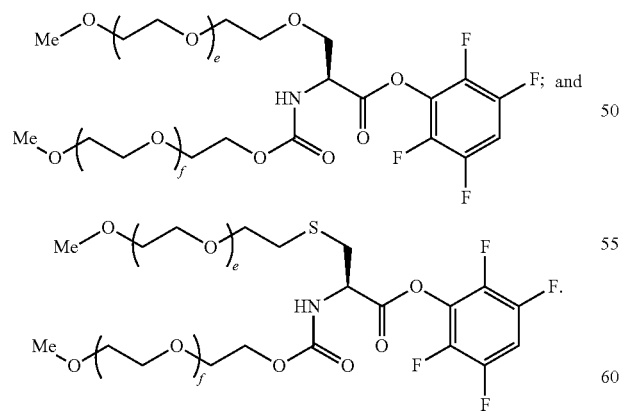

Other activating, or leaving groups, appropriate for activating linear and branched PEGs of use in preparing the compounds set forth herein include, but are not limited to the species:

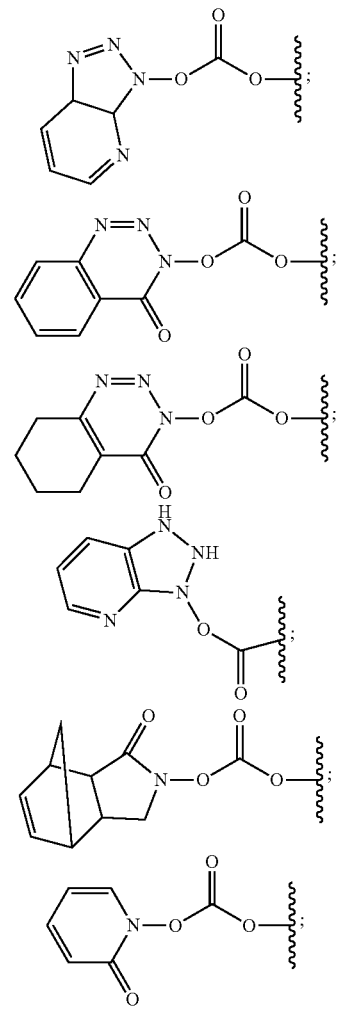

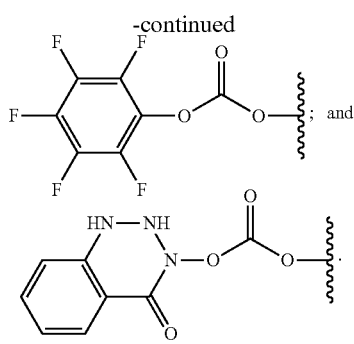

PEG molecules that are activated with these and other species and methods of making the activated PEGs are set forth in WO 04/083259.

Those of skill in the art will appreciate that one or more of the rn-PEG arms of the branched polymers shown above can be replaced by a PEG moiety with a different terminus, e.g., OH, COOH, $NH_2$, $C_2$-$C_{10}$-alkyl, etc. Moreover, the structures above are readily modified by inserting alkyl linkers (or removing carbon atoms) between the α-carbon atom and the functional group of the amino acid side chain. Thus, "homo" derivatives and higher homologues, as well as lower homologues are within the scope of cores for branched PEGs of use in the present invention.

The branched PEG species set forth herein are readily prepared by methods such as that set forth in the scheme below:

in which $X^d$ is O or S and r is an integer from 1 to 5. The indices e and f are independently selected integers from 1 to 2500. In an exemplary embodiment, one or both of these indices are selected such that the polymer is about 10 kD, 15 kD or 20 kD in molecular weight.

Thus, according to this scheme, a natural or unnatural amino acid is contacted with an activated m-PEG derivative, in this case the tosylate, forming 1 by alkylating the side-chain heteroatom $X^d$. The mono-functionalize m-PEG amino acid is submitted to N-acylation conditions with a reactive m-PEG derivative, thereby assembling branched m-PEG 2. As one of skill will appreciate, the tosylate leaving group can be replaced with any suitable leaving group, e.g., halogen, mesylate, triflate, etc. Similarly, the reactive carbonate utilized to acylate the amine can be replaced with an active ester, e.g., N-hydroxysuccinimide, etc., or the acid can be activated in situ using a dehydrating agent such as dicyclohexylcarbodiimide, carbonyldiimidazole, etc.

In other exemplary embodiments, the urea moiety is replaced by a group such as a amide.

In an illustrative embodiment, the modified sugar is sialic acid and selected modified sugar compounds of use in the invention have the formulae:

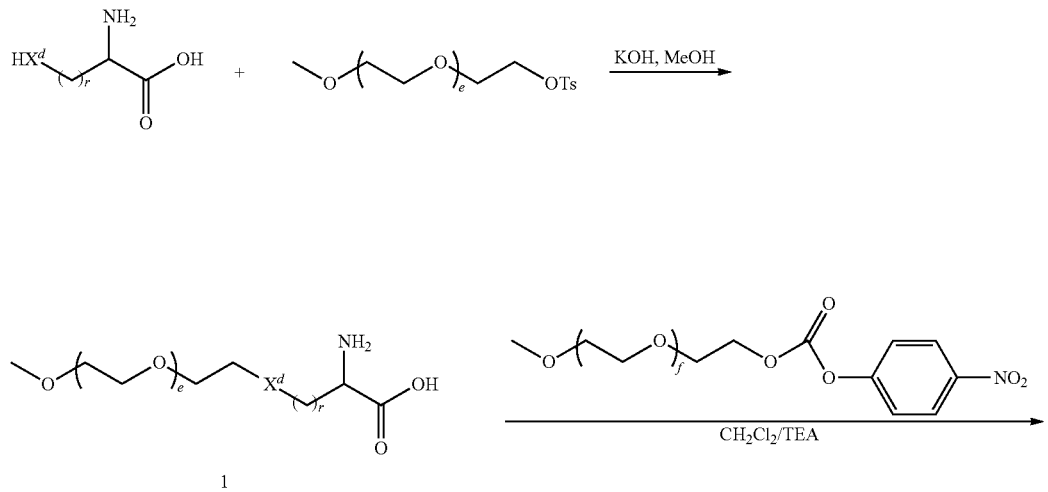

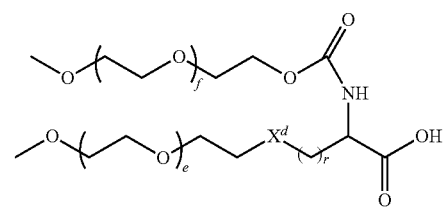

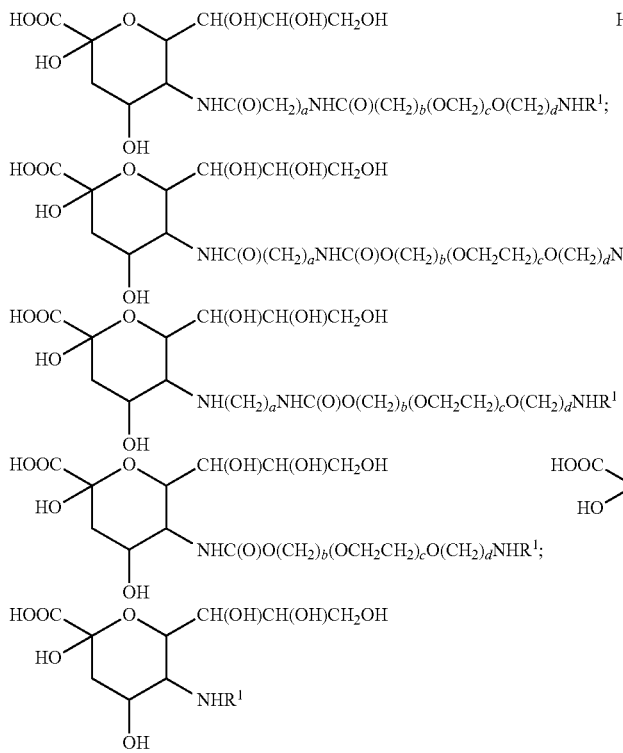
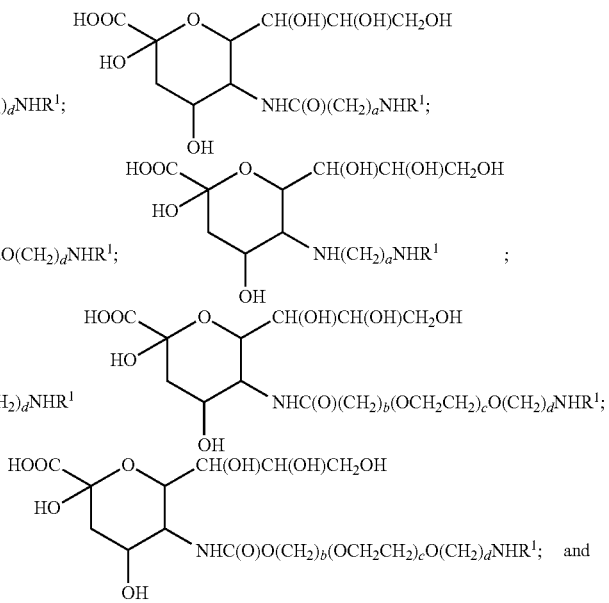

The indices a, b and d are integers from 0 to 20. The index c is an integer from 1 to 2500. The structures set forth above can be components of $R^{15}$.

In another illustrative embodiment, a primary hydroxyl moiety of the sugar is functionalized with the modifying group. For example, the 9-hydroxyl of sialic acid can be converted to the corresponding amine and functionalized to provide a compound according to the invention. Formulae according to this embodiment include:

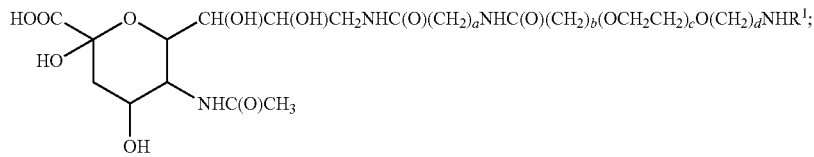

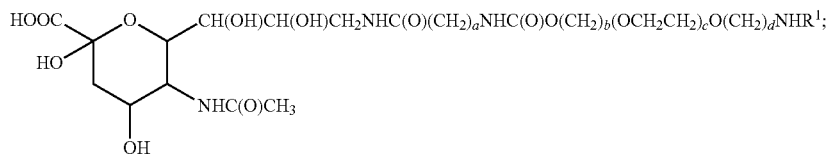

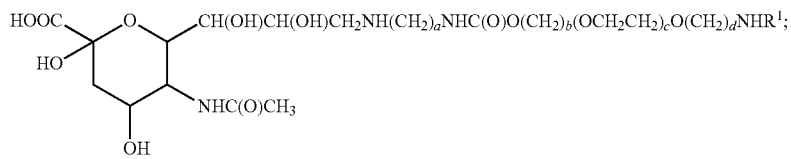

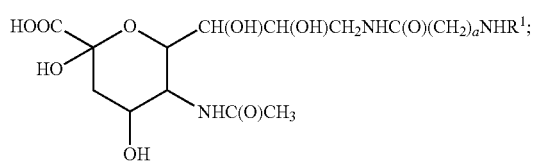
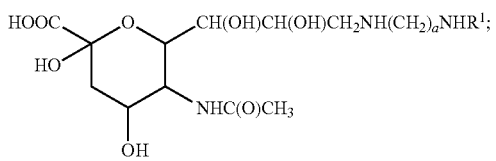

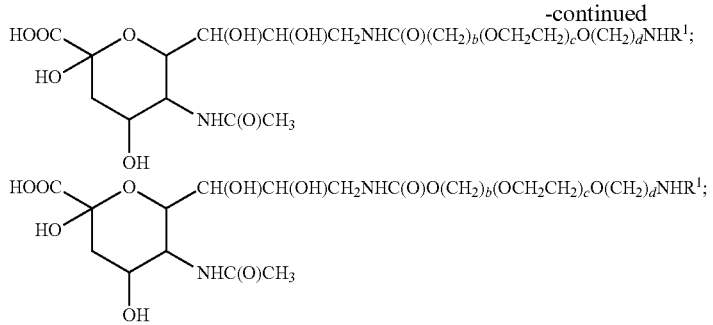

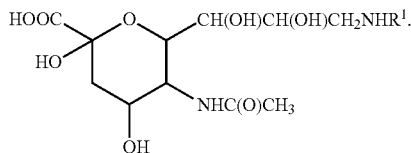

The structures set forth above can be components of $R^{15}/R^{15'}$.

As those of skill in the art will appreciate, the sialic acid moiety in the exemplary compounds above can be replaced with any other amino-saccharide including, but not limited to, glucosamine, galactosamine, mannosamine, their N-acyl derivatives, and the like.

Although the present invention is exemplified in the preceding sections by reference to PEG, as those of skill will appreciate, an array of polymeric modifying moieties is of use in the compounds and methods set forth herein.

In selected embodiments, $R^1$ or $L-R^1$ is a branched PEG, for example, one of the species set forth above. Illustrative modified sugars according to this embodiment include:

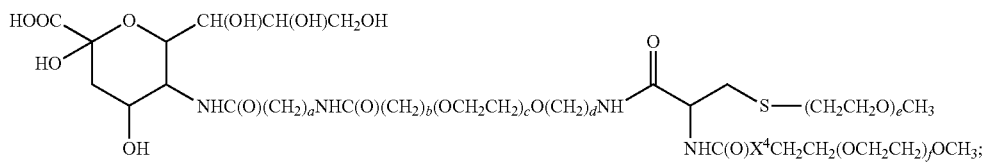

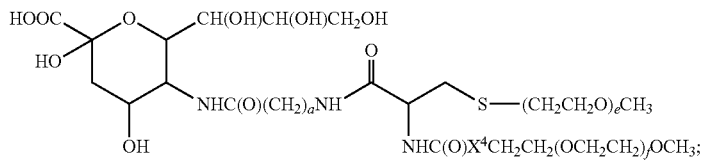

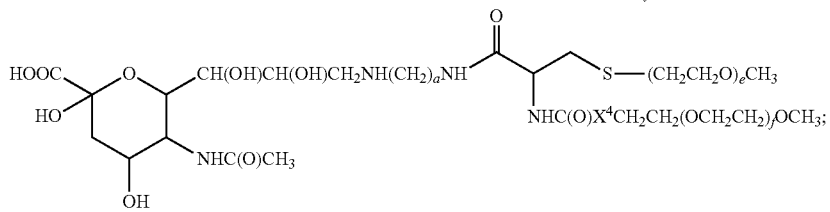

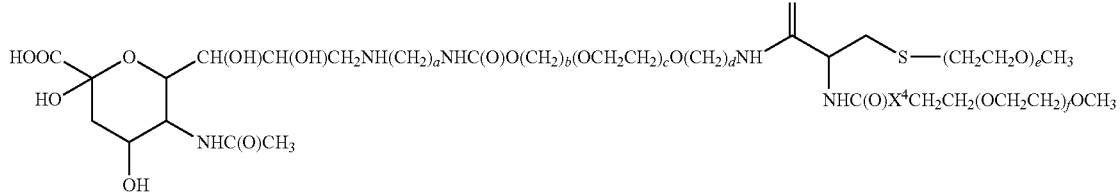

in which $X^4$ is a bond or O. In each of the structures above, the alkylamine linker —$(CH_2)_a NH$— can be present or absent. The structures set forth above can be components of $R^{15}/R^{15'}$.

As discussed herein, the polymer-modified sialic acids of use in the invention may also be linear structures. Thus, the invention provides for conjugates that include a sialic acid moiety derived from a structure such as:

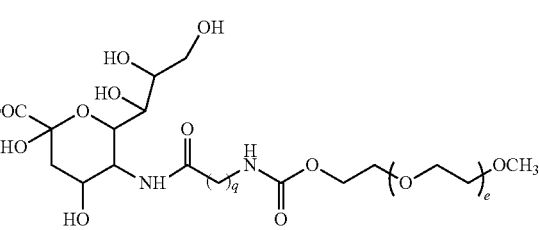

in which q and e are as discussed above.

Water-Insoluble Polymers

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

The motifs forth above for $R^1$, $L-R^1$, $R^{15}$, $R^{15'}$ and other radicals are equally applicable to water-insoluble polymers, which may be incorporated into the linear and branched structures without limitation utilizing chemistry readily accessible to those of skill in the art.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly (isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid" polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly(α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J Biomed. Mater. Res.* 21: 1301-1316 (1987); and Cohn et al., *J Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly (amino acids), poly(anhydrides), poly(orthoesters), poly (carbonates), poly(phosphazines), poly(phosphoesters), poly (thioesters), polysaccharides and mixtures thereof. More preferably still, the biosresorbable polymer includes a poly (hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other polymers based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a di-functional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly(propylene) oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. Nos. 5,410,016, which issued on Apr. 25, 1995 and U.S. Pat. No. 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly(α-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, is of use in the present invention.

The structural formats discussed above in the context of the water-soluble polymers, both straight-chain and branched are generally applicable with respect to the water-insoluble polymers as well. Thus, for example, the cysteine, serine, dilysine, and trilysine branching cores can be functionalized with two water-insoluble polymer moieties. The methods used to produce these species are generally closely analogous to those used to produce the water-soluble polymers.

The Methods

In addition to the conjugates discussed above, the present invention provides methods for preparing these and other conjugates. Moreover, the invention provides methods of preventing, curing or ameliorating a disease state by administering a conjugate of the invention to a subject at risk of developing the disease or a subject that has the disease.

In exemplary embodiments, the conjugate is formed between a polymeric modifying moiety and a glycosylated or non-glycosylated peptide. The polymer is conjugated to the peptide via a glycosyl linking group, which is interposed between, and covalently linked to both the peptide (or glycosyl residue) and the modifying group (e.g., water-soluble polymer). The method includes contacting the peptide with a mixture containing a modified sugar and an enzyme, e.g., a glycosyltransferase that conjugates the modified sugar to the substrate. The reaction is conducted under conditions appropriate to form a covalent bond between the modified sugar and the peptide. The sugar moiety of the modified sugar is preferably selected from nucleotide sugars.

In an exemplary embodiment, the modified sugar, such as those set forth above, is activated as the corresponding nucleotide sugars. Exemplary sugar nucleotides that are used in the present invention in their modified form include nucleotide mono-, di- or triphosphates or analogs thereof. In a preferred embodiment, the modified sugar nucleotide is selected from a UDP-glycoside, CMP-glycoside, or a GDP-glycoside. Even more preferably, the sugar nucleotide portion of the modified sugar nucleotide is selected from UDP-galactose, UDP-galactosamine, UDP-glucose, UDP-glucosamine, GDP-mannose, GDP-fucose, CMP-sialic acid, or CMP-NeuAc. In an exemplary embodiment, the nucleotide phosphate is attached to C-1.

Thus, in an illustrative embodiment in which the glycosyl moiety is sialic acid, the method of the invention utilizes compounds having the formulae:

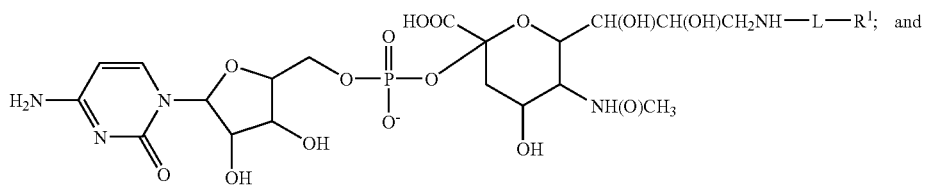

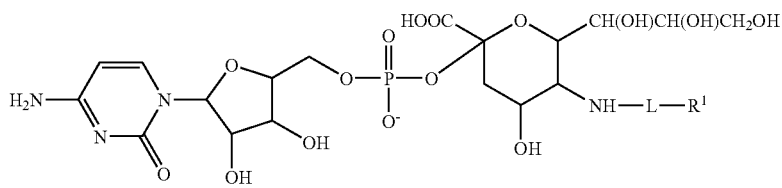

in which L-R$^1$ is as discussed above, and L$^1$-R$^1$ represents a linker bound to the modifying group. As with L, exemplary linker species according to L$^1$ include a bond, alkyl or heteroalkyl moieties.

Moreover, as discussed above, the present invention provides for the use of nucleotide sugars that are modified with a water-soluble polymer, which is either straight-chain or branched. For example, compounds having the formula shown below are of use to prepare conjugates within the scope of the present invention:

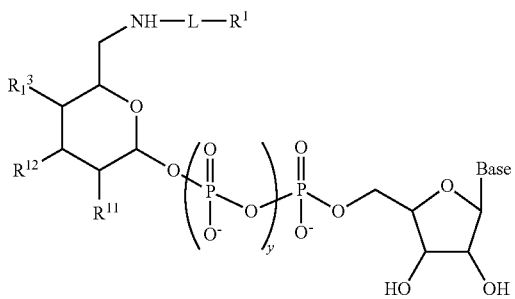

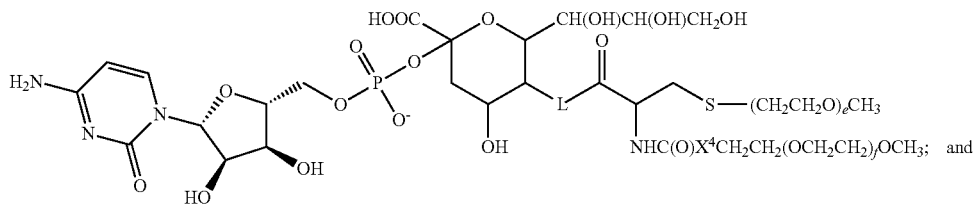

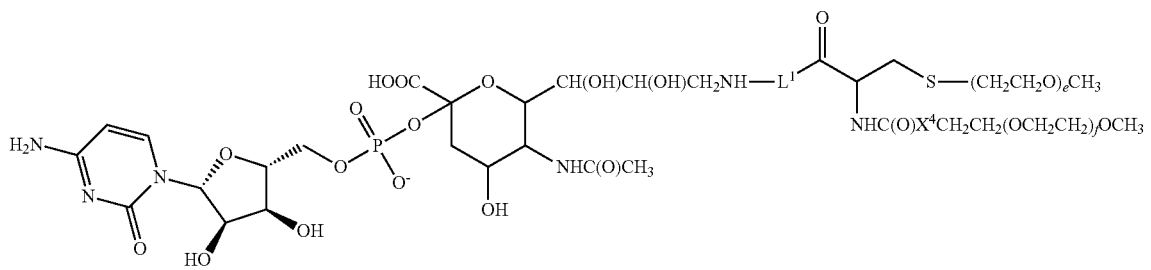

in which X$^4$ is O or a bond.

The invention also provides for the use of sugar nucleotides modified with L-R$^1$ at the 6-carbon position. Exemplary species according to this embodiment include:

in which the R groups, and L, represent moieties as discussed above. The index "y" is 0, 1 or 2. In an exemplary embodiment, L is a bond between NH and R$^1$. The base is a nucleic acid base.

Exemplary nucleotide sugars of use in the invention in which the carbon at the 6-position is modified include species having the stereochemistry of GDP mannose, e.g.:

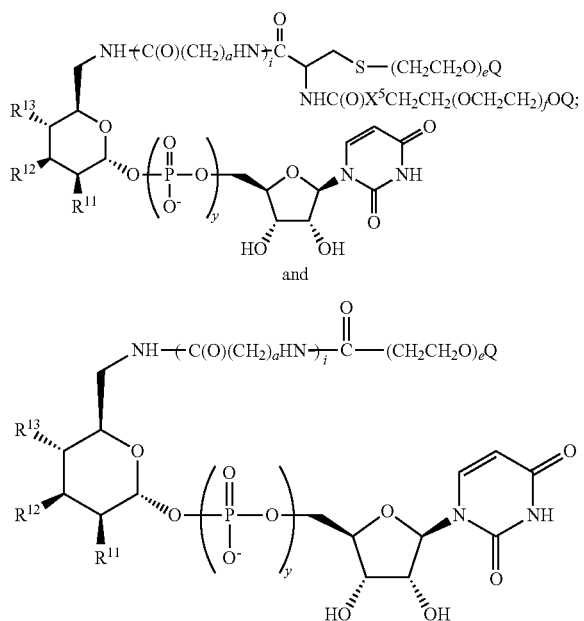

and

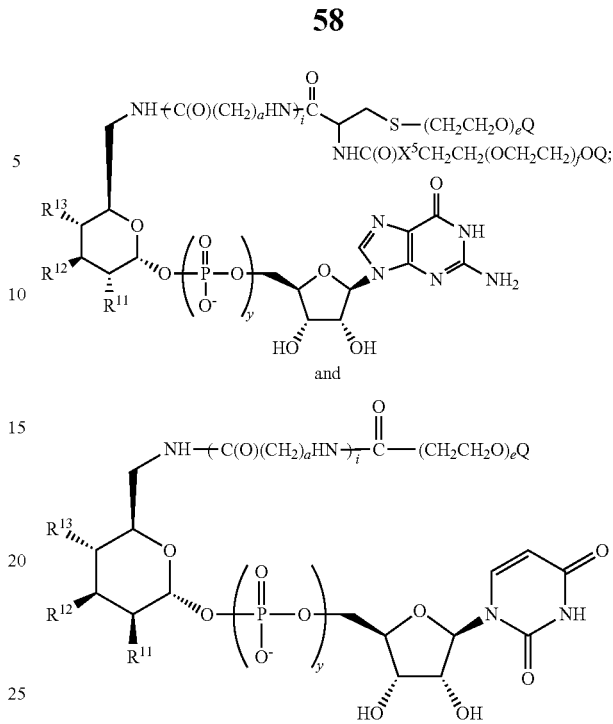

and in which $X^5$ is a bond or O. The index i represents 0 or 1. The index a represents an integer from 1 to 20. The indices e and f independently represent integers from 1 to 2500. Q, as discussed above, is H or substituted or unsubstituted $C_1$-$C_6$ alkyl. As those of skill will appreciate, the serine derivative, in which S is replaced with O also falls within this general motif.

In a still further exemplary embodiment, the invention provides a conjugate in which the modified sugar is based on the stereochemistry of UDP galactose. An exemplary nucleotide sugar of use in this invention has the structure:

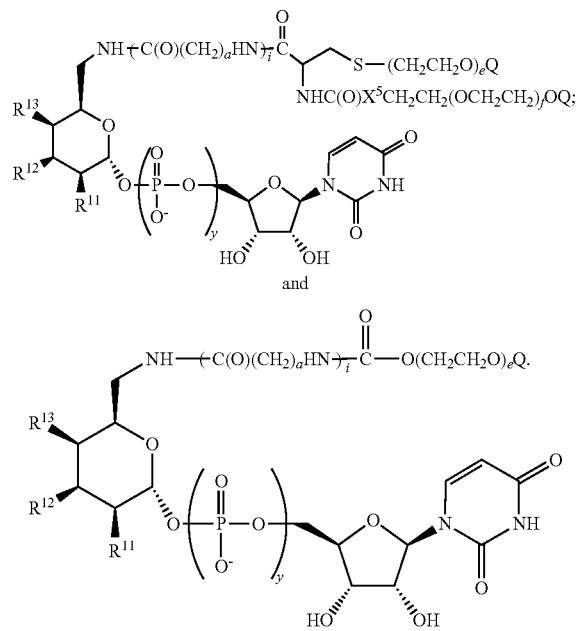

and

In another exemplary embodiment, the nucleotide sugar is based on the stereochemistry of glucose. Exemplary species according to this embodiment have the formulae:

In general, the sugar moiety or sugar moiety-linker cassette and the PEG or PEG-linker cassette groups are linked together through the use of reactive groups, which are typically transformed by the linking process into a new organic functional group or unreactive species. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a sugar nucleus or modifying group include, but are not limited to:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups, which can be converted to, e.g., esters, ethers, aldehydes, etc.
(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be, for example, converted to disulfides or reacted with acyl halides;
(h) amine or sulfhydryl groups, which can be, for example, acylated, alkylated or oxidized;
(i) alkenes, which can undergo, for example, cycloadditions, acylation, Michael addition, etc; and
(j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., Curr. Med. Chem. 6: 93 (1999); and Schafer et al., J. Org. Chem. 65: 24 (2000)).

Figure 5:
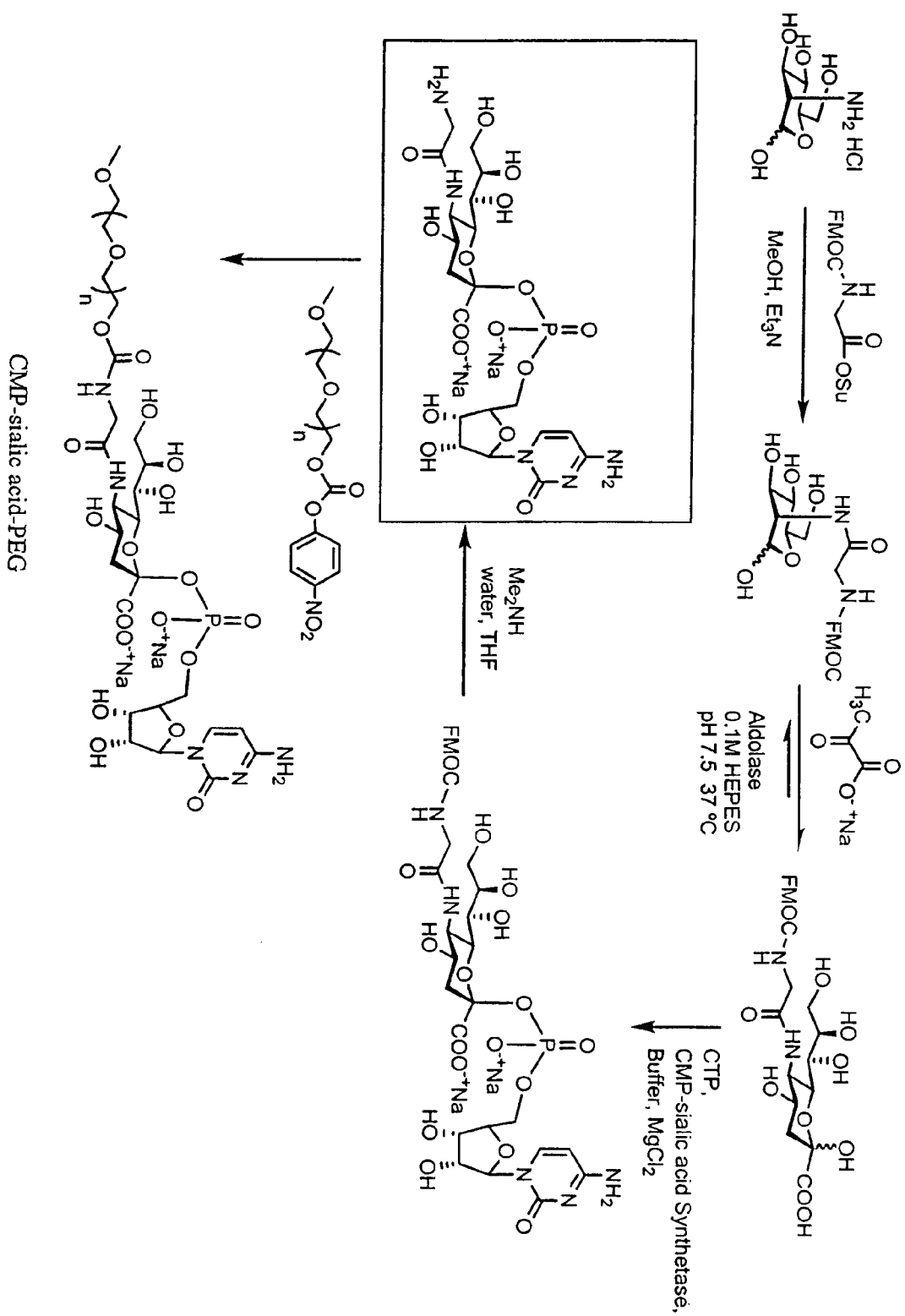
FIG. 5 is a synthetic scheme for producing an exemplary PEG-glycosyl linking group precursor (modified sugar) of us in preparing the conjugates of the invention.
Figure 8A:
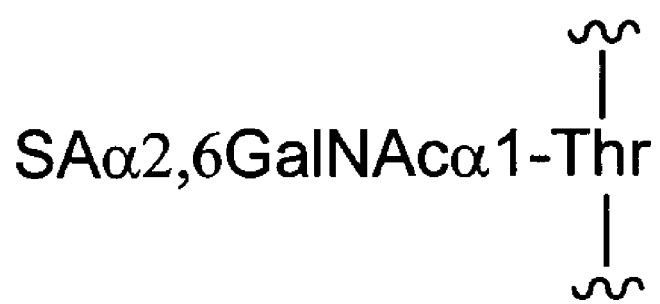
FIG. 8 shows an exemplary O-linked glycan structure on a G-CSF glycoconjugate of the invention.
Figure 8B:
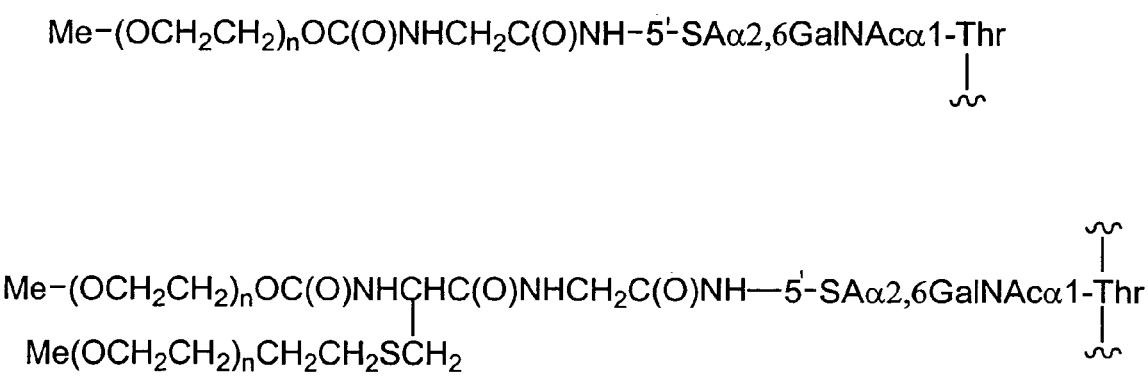
Figure 9:
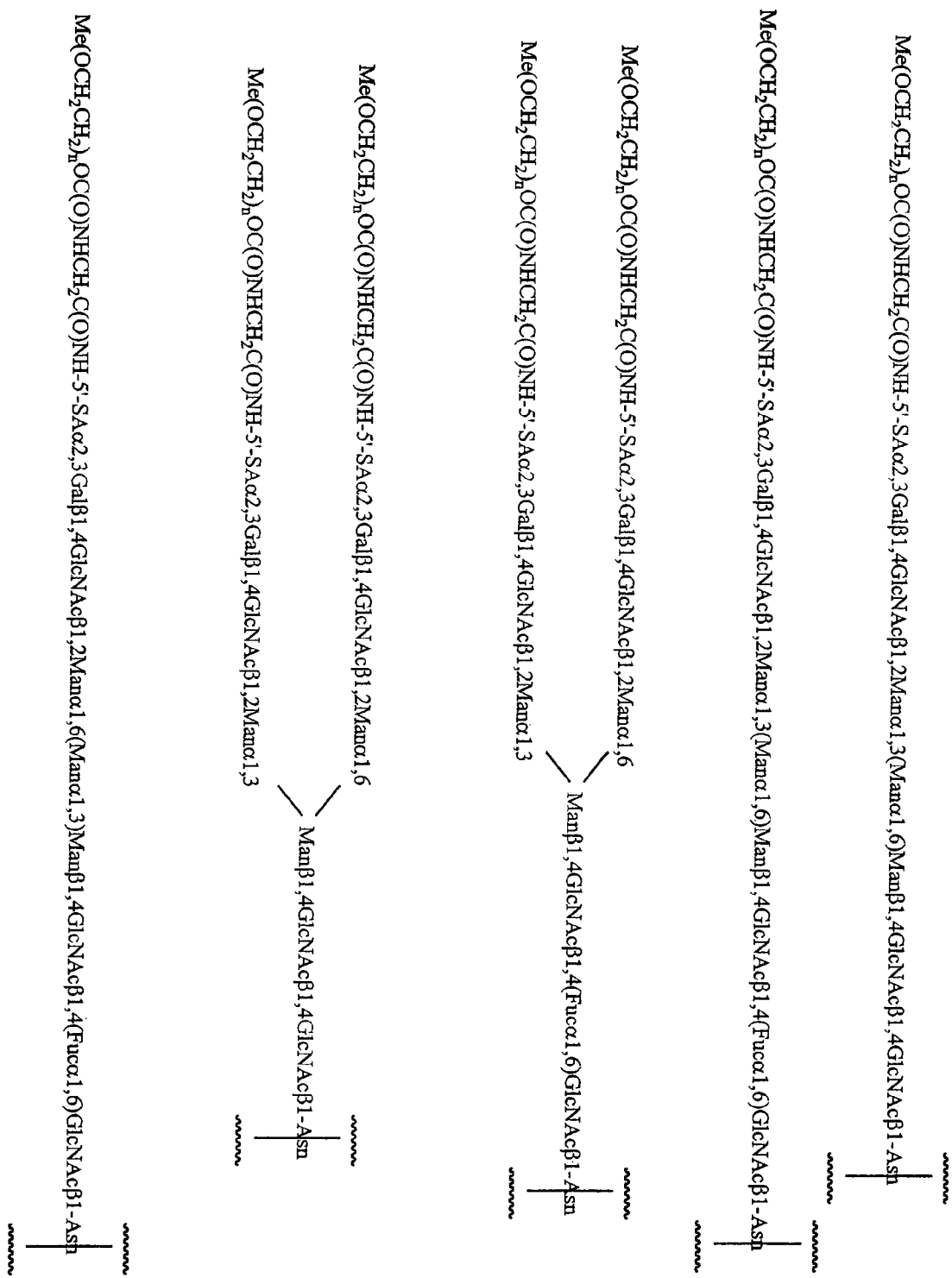
FIG. 9 shows an exemplary N-linked glycan structure on a mutant G-CSF glycoconjugate of the invention expressed in insect cells (and remodeled and glycopegylated) in which the mutant includes one or more N-linked glycosylation sites.
Figure 10A:
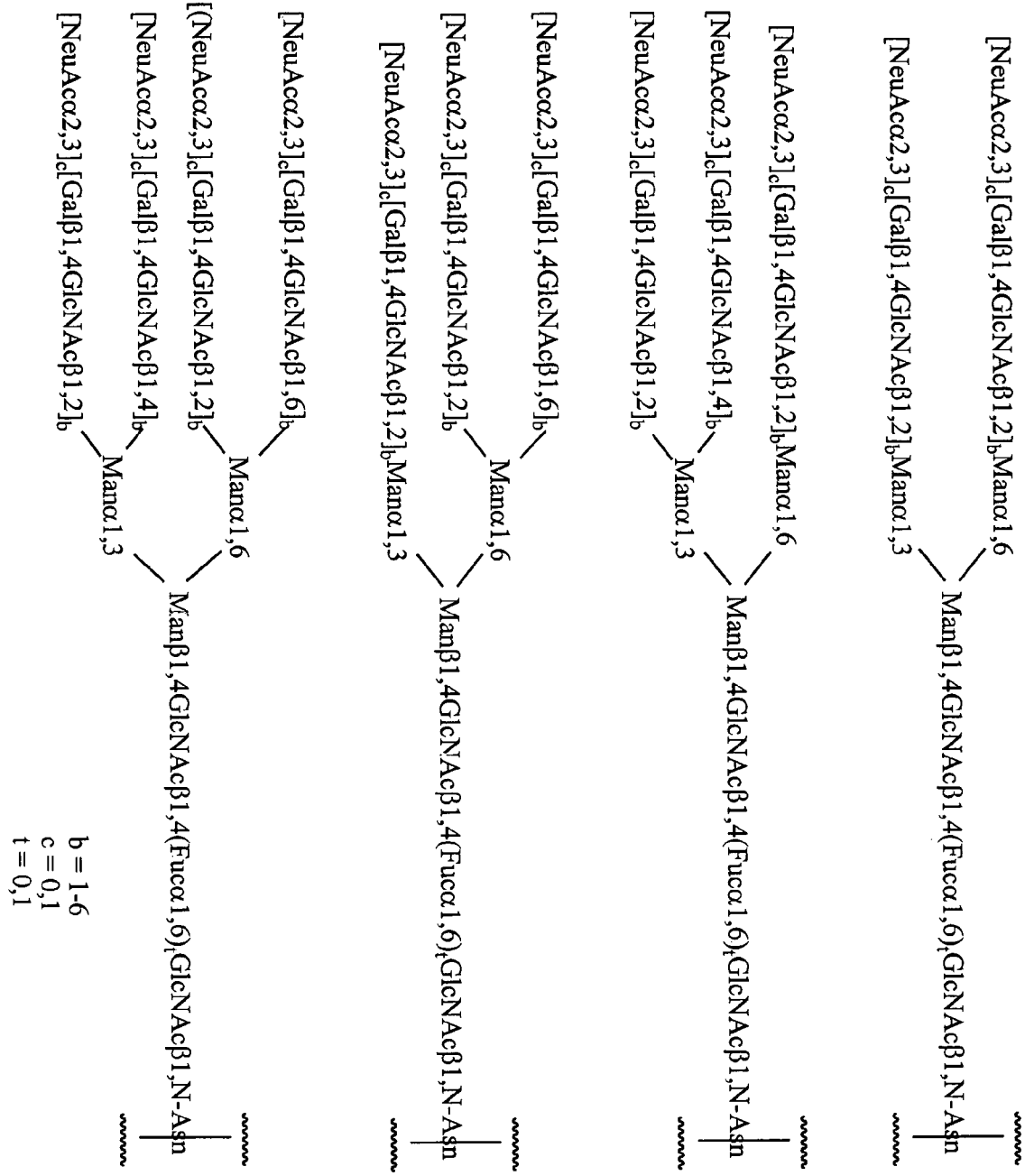
FIG. 10 shows an exemplary N-linked glycan structure on a mutant G-CSF glycoconjugate of the invention expressed in mammalian cells (and glycopegylated) in which the mutant includes one or more N-linked glycosylation sites.
Figure 10B:
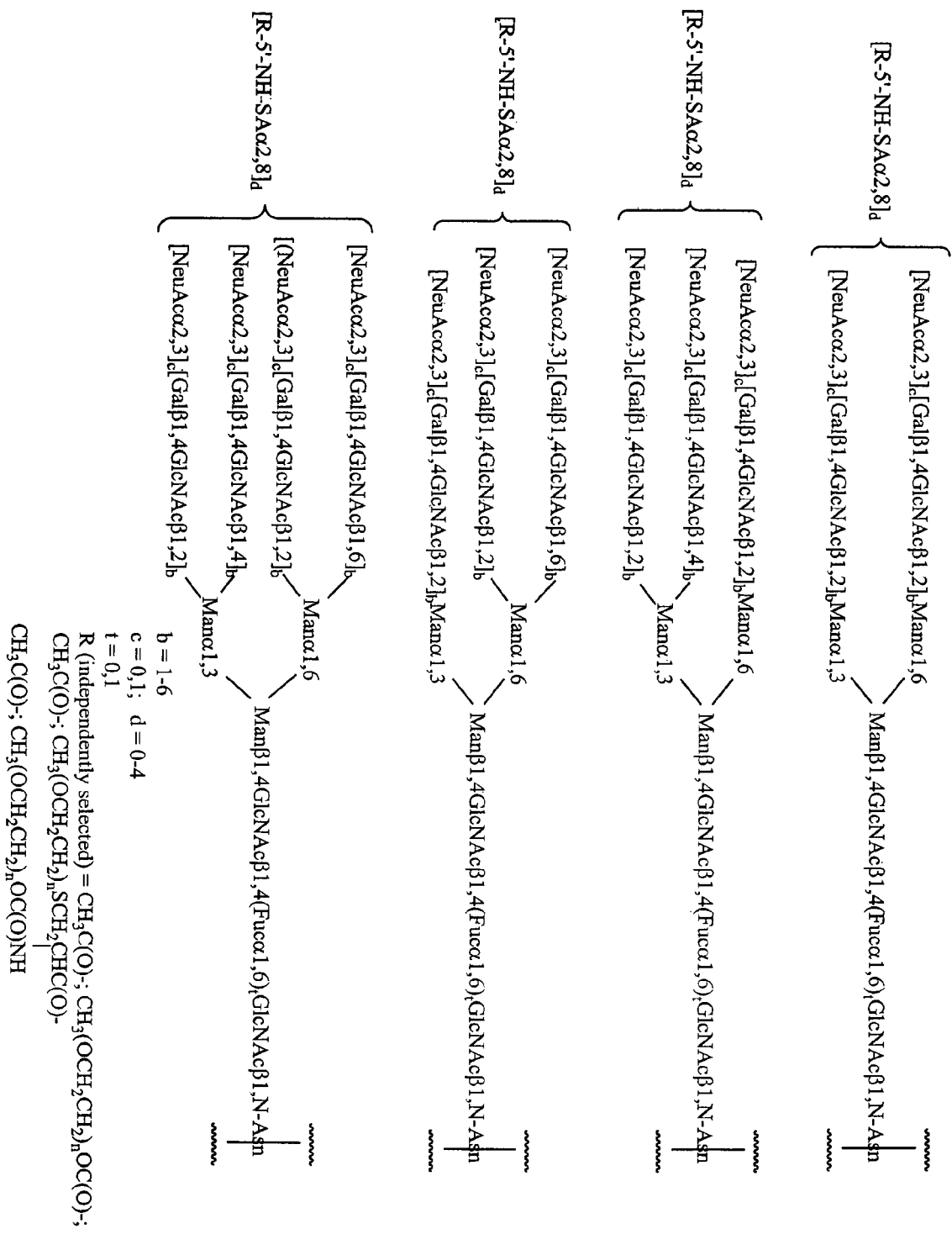
Figure 10C:
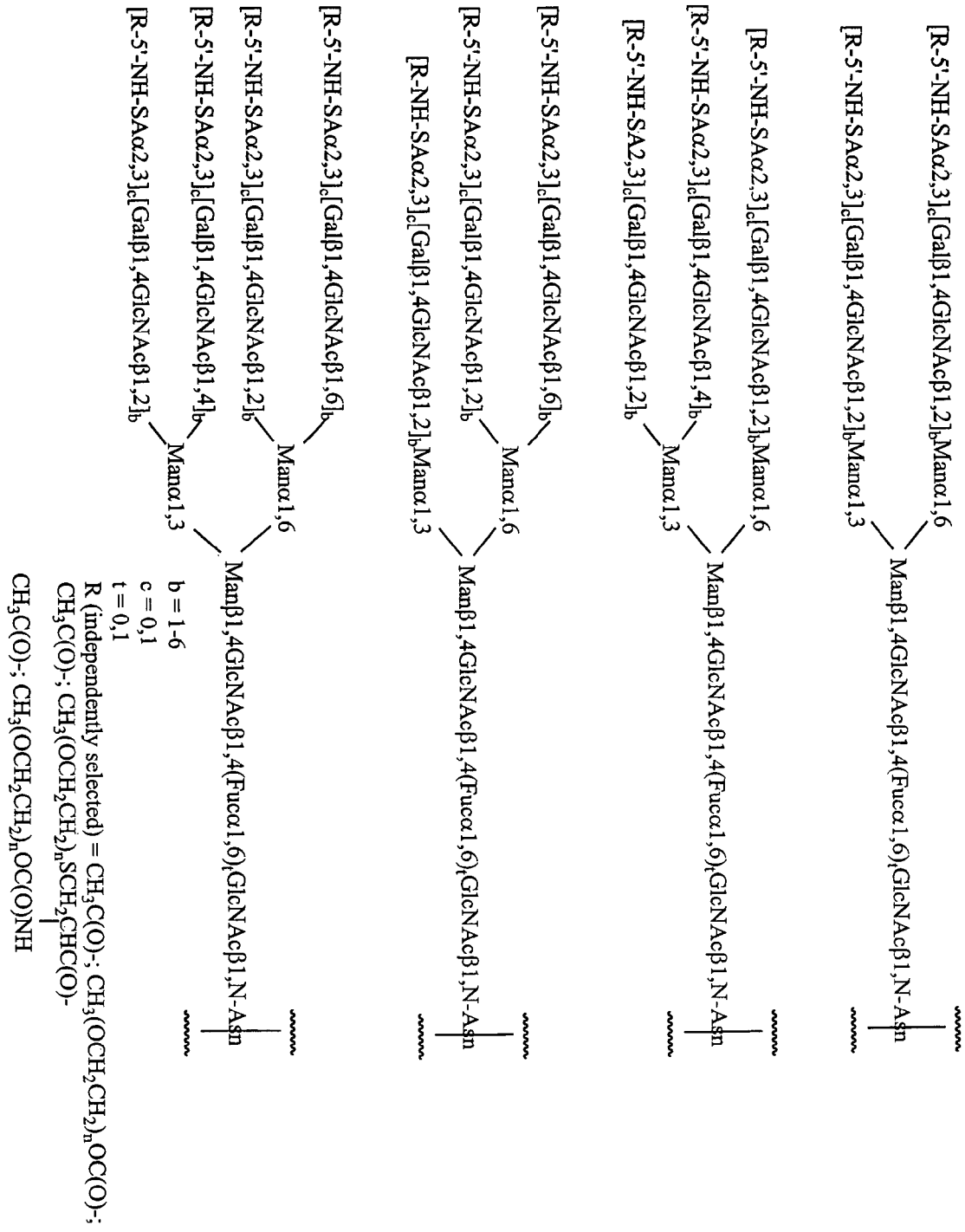

In an exemplary embodiment, the modified sugar is based upon a 6-amino-N-acetyl-glycosyl moiety. As shown in FIG. 5 for N-acetylgalactosamine, the 6-amino-sugar moiety is readily prepared by standard methods.

In the scheme above, the index n represents an integer from 1 to 2500. In an exemplary embodiment, this index is selected such that the polymer is about 10 kD, 15 kD or 20 kD in molecular weight. The symbol "A" represents an activating group, e.g., a halo, a component of an activated ester (e.g., a N-hydroxysuccinimide ester), a component of a carbonate (e.g., p-nitrophenyl carbonate) and the like. Those of skill in the art will appreciate that other PEG-amide nucleotide sugars are readily prepared by this and analogous methods.

The acceptor peptide is typically synthesized de novo, or recombinantly expressed in a prokaryotic cell (e.g., bacterial cell, such as E. coli) or in a eukaryotic cell such as a mammalian, yeast, insect, fungal or plant cell. The peptide can be either a full-length protein or a fragment. Moreover, the peptide can be a wild type or mutated peptide. In an exemplary embodiment, the peptide includes a mutation that adds one or more N- or O-linked glycosylation sites to the peptide sequence.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Those of skill will appreciate that the invention can be practiced using substantially any peptide or glycopeptide from any source. Exemplary peptides with which the invention can be practiced are set forth in WO 03/031464, and the references set forth therein.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-acetylgalactosamine, galactose, mannose, GlcNAc, glucose, fucose or xylose) to the hydroxy side chain of a hydroxyamino acid, preferably serine or threonine, although unusual or non-natural amino acids, e.g., 5-hydroxyproline or 5-hydroxylysine may also be used.

Moreover, in addition to peptides, the methods of the present invention can be practiced with other biological structures (e.g., glycolipids, lipids, sphingoids, ceramides, whole cells, and the like, containing a glycosylation site).

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, Proc. Natl. Acad. Sci. USA 91:10747-10751 (1994); Stemmer, Nature 370:389-391 (1994); and U.S. Pat. Nos. 5,605,793, 5,837,458, 5,830,721 and 5,811,238.

Exemplary peptides with which the present invention can be practiced, methods of adding or removing glycosylation sites, and adding or removing glycosyl structures or substructures are described in detail in WO03/031464 and related U.S. and PCT applications.

The present invention also takes advantage of adding to (or removing from) a peptide one or more selected glycosyl residues, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. An exemplary chemical deglycosylation is brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

In an exemplary embodiment, the peptide is essentially completely desialylated with neuraminidase prior to performing glycoconjugation or remodeling steps on the peptide; Following the glycoconjugation or remodeling, the peptide is optionally re-sialylated using a sialyltransferase. In an exemplary embodiment, the re-sialylation occurs at essentially each (e.g., >80%, preferably greater than 85%, greater than 90%, preferably greater than 95% and more preferably greater than 96%, 97%, 98% or 99%) terminal saccharyl acceptor in a population of sialyl acceptors. In a preferred embodiment, the saccharide has a substantially uniform sialylation pattern (i.e., substantially uniform glycosylation pattern).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation, and sites for O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

In one embodiment, the invention provides a method for linking two or more peptides through a linking group. The linking group is of any useful structure and may be selected from straight- and branched-chain structures. Preferably, each terminus of the linker, which is attached to a peptide, includes a modified sugar (i.e., a nascent intact glycosyl linking group).

In an exemplary method of the invention, two peptides are linked together via a linker moiety that includes a polymeric (e.g., PEG linker). The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosyl units, respectively. In practice, the $(glycosyl)^1$-PEG-$(glycosyl)^2$ linker is contacted with the first peptide and a first transferase for which the first glycosyl unit is a substrate, thereby forming $(peptide)^1$-$(glycosyl)^1$-PEG-$(glycosyl)^2$. Transferase and/or unreacted peptide is then optionally removed from the reaction mixture. The second peptide and a second transferase for which the second glycosyl unit is a substrate are added to the $(peptide)^1$-$(glycosyl)^1$-PEG-$(glycosyl)^2$ conjugate, forming $(peptide)^1$-$(glycosyl)^1$-PEG-$(glycosyl)^2$-$(peptide)^2$; at least one of the glycosyl residues is either directly or indirectly O-linked. Those of skill in the art will appreciate that the method outlined above is also applicable to forming conjugates between more than two peptides by, for example, the use of a branched PEG, dendrimer, poly(amino acid), polysaccharide or the like.

In an exemplary embodiment, the peptide that is modified by a method of the invention is a glycopeptide that is produced in mammalian cells (e.g., CHO cells) or in a transgenic animal and thus, contains N- and/or O-linked oligosaccharide chains, which are incompletely sialylated. The oligosaccharide chains of the glycopeptide lacking a sialic acid and containing a terminal galactose residue can be PEGylated, PPGylated or otherwise modified with a modified sialic acid.

In Scheme 1, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG attachment by reacting compound 3 with an activated PEG or PPG derivative (e.g., PEG-C(O)NHS, PEG-OC(O)O-p-nitrophenyl), producing species such as 4 or 5, respectively.

Scheme 1

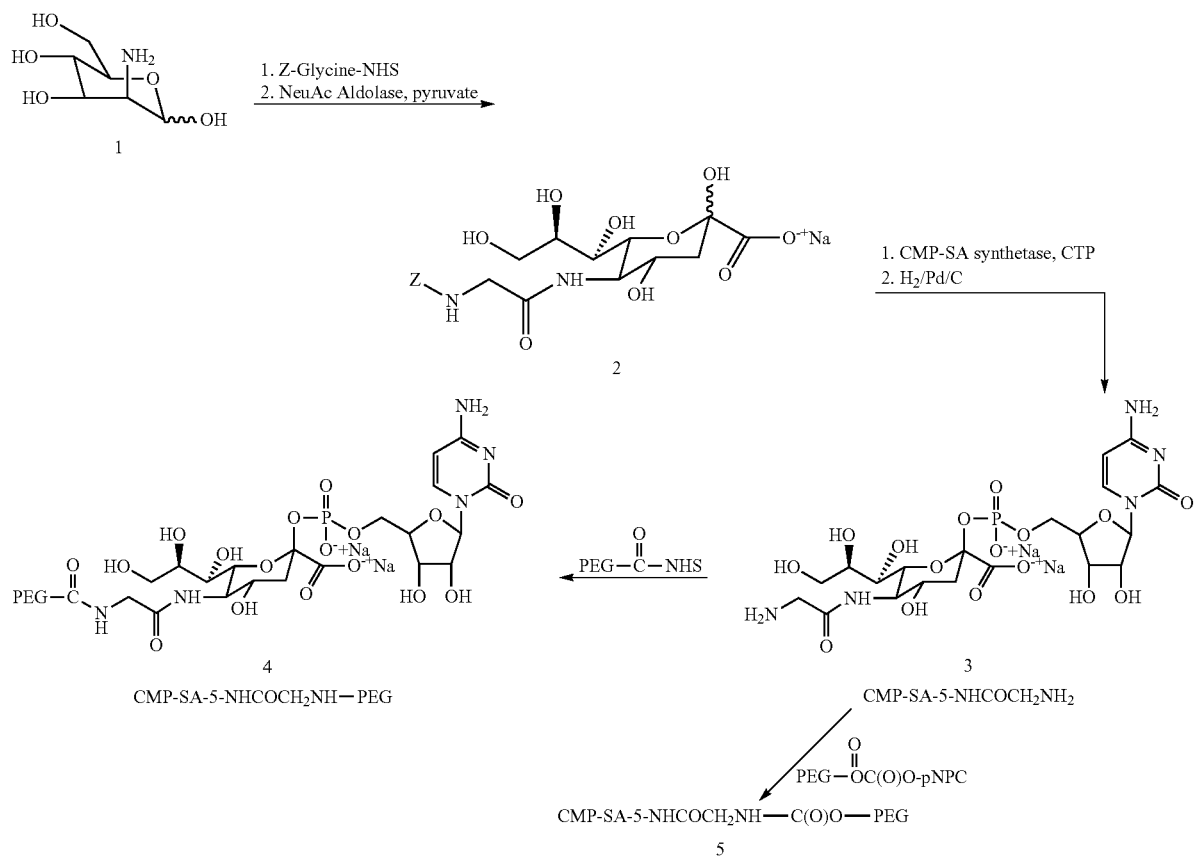

Conjugation of Modified Sugars to Peptides

The PEG modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), U.S. Pat. Nos. 5,352,670, 5,374,541, 5,545,553, commonly owned U.S. Pat. Nos. 6,399,336, and 6,440,703, and commonly owned published PCT applications, WO 03/031464, WO 04/033651, WO 04/099231, which are incorporated herein by reference.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

In another embodiment, the method-makes use of one or more exo- or endoglycosidase. The glycosidase is typically a mutant, which is engineered to form glycosyl bonds rather than rupture them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 37° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few h, with recoverable amounts usually being obtained within 24 h or less. Those of skill in the art understand that the rate of reaction is dependent on a number of variable factors (e.g, enzyme concentration, donor concentration, acceptor concentration, temperature, solvent volume), which are optimized for a selected system.

The present invention also provides for the industrial-scale production of modified peptides. As used herein, an industrial scale generally produces at least one gram of finished, purified conjugate.

In the discussion that follows, the invention is exemplified by the conjugation of modified sialic acid moieties to a glycosylated peptide. The exemplary modified sialic acid is labeled with PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other PEG moieties, therapeutic moieties, and biomolecules.

An enzymatic approach can be used for the selective introduction of PEGylated or PPGylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

In an exemplary embodiment, an acceptor for a sialyltransferase is present on the peptide to be modified either as a naturally occurring structure or it is placed there recombinantly, enzymatically or chemically. Suitable acceptors, include, for example, galactosyl acceptors such as Galβ1, 4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)). Exemplary sialyltransferases are set forth herein.

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GlcNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases. and endoglycosidases (see, for example U.S. Pat. No. 5,716,812) are useful for the attaching and trimming reactions. In another embodiment of this method, the sialic acid moieties of the peptide are essentially completely removed (e.g., at least 90, at least 95 or at least 99%), exposing an acceptor for a modified sialic acid.

In the discussion that follows, the method of the invention is exemplified by the use of modified sugars having a PEG moiety attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment of the invention in which a carbohydrate residue is "trimmed" prior to the addition of the modified sugar high mannose is trimmed back to the first generation biantennary structure. A modified sugar bearing a PEG moiety is conjugated to one or more of the sugar residues exposed by the "trimming back." In one example, a PEG moiety is added via a GlcNAc moiety conjugated to the PEG moiety. The modified GlcNAc is attached to one or both of the terminal mannose residues of the biantennary structure. Alternatively, an unmodified GlcNAc can be added to one or both of the termini of the branched species.

In another exemplary embodiment, a PEG moiety is added to one or both of the terminal mannose residues of the biantennary structure via a modified sugar having a galactose residue, which is conjugated to a GlcNAc residue added onto the terminal mannose residues. Alternatively, an unmodified Gal can be added to one or both terminal GlcNAc residues.

In yet a further example, a PEG moiety is added onto a Gal residue using a modified sialic acid such as those discussed above.

In another exemplary embodiment, a high mannose structure is "trimmed back" to the mannose from which the biantennary structure branches. In one example, a PEG moiety is added via a GlcNAc modified with the polymer. Alternatively, an unmodified GlcNAc is added to the mannose, followed by a Gal with an attached PEG moiety. In yet another embodiment, unmodified GlcNAc and Gal residues are sequentially added to the mannose, followed by a sialic acid moiety modified with a PEG moiety.

A high mannose structure can also be trimmed back to the elementary tri-mannosyl core.

In a further exemplary embodiment, high mannose is "trimmed back" to the GlcNAc to which the first mannose is attached. The GlcNAc is conjugated to a Gal residue bearing a PEG moiety. Alternatively, an unmodified Gal is added to the GlcNAc, followed by the addition of a sialic acid modified with a water-soluble sugar. In yet a further example, the terminal GlcNAc is conjugated with Gal and the GlcNAc is subsequently fucosylated with a modified fucose bearing a PEG moiety.

High mannose may also be trimmed back to the first GlcNAc attached to the Asn of the peptide. In one example, the GlcNAc of the GlcNAc-(Fuc)$_a$ residue is conjugated wit ha GlcNAc bearing a water soluble polymer. In another example, the GlcNAc of the GlcNAc-(Fuc)$_a$ residue is modified with Gal, which bears a water soluble polymer. In a still further embodiment, the GlcNAc is modified with Gal, followed by conjugation to the Gal of a sialic acid modified with a PEG moiety.

Other exemplary embodiments are set forth in commonly owned U.S. Patent application Publications: 20040132640; 20040063911; 20040137557; U.S. patent application Ser. Nos. 10/369,979; 10/410,913; 10/360,770; 10/410,945 and PCT/US02/32263 each of which is incorporated herein by reference.

The Examples set forth above provide an illustration of the power of the methods set forth herein. Using the methods described herein, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, an existing sialic acid is removed from a glycopeptide using a sialidase, thereby unmasking all or most of the underlying galactosyl residues. Alternatively, a peptide or glycopeptide is labeled with galactose residues, or an oligosaccharide residue that terminates in a galactose unit. Following the exposure of or addition of the galactose residues, an appropriate sialyltransferase is used to add a modified sialic acid.

In another exemplary embodiment, an enzyme that transfers sialic acid onto sialic acid is utilized. This method can be practiced without treating a sialylated glycan with a sialidase to expose glycan residues beneath the sialic acid. An exemplary polymer-modified sialic acid is a sialic acid modified with poly(ethylene glycol). Other exemplary enzymes that add sialic acid and modified sialic acid moieties onto glycans that include a sialic acid residue or exchange an existing sialic acid residue on a glycan for these species include ST3Gal3, CST-II, ST8Sia-II, ST8Sia-III and ST8Sia-IV.

In yet a further approach, a masked reactive functionality is present on the sialic acid. The masked reactive group is preferably unaffected by the conditions used to attach the modified sialic acid to the G-CSF. After the covalent attachment of the modified sialic acid to the peptide, the mask is removed and the peptide is conjugated with an agent such as PEG. The agent is conjugated to the peptide in a specific manner by its reaction with the unmasked reactive group on the modified sugar residue.

Any modified sugar can be used with its appropriate glycosyltransferase, depending on the terminal sugars of the oligosaccharide side chains of the glycopeptide. As discussed above, the terminal sugar of the glycopeptide required for introduction of the PEGylated structure can be introduced naturally during expression or it can be produced post expression using the appropriate glycosidase(s), glycosyltransferase(s) or mix of glycosidase(s) and glycosyltransferase(s).

In a further exemplary embodiment, UDP-galactose-PEG is reacted with β1,4-galactosyltransferase, thereby transferring the modified galactose to the appropriate terminal N-acetylglucosamine structure. The terminal GlcNAc residues on the glycopeptide may be produced during expression, as may occur in such expression systems as mammalian, insect, plant or fungus, but also can be produced by treating the glycopeptide with a sialidase and/or glycosidase and/or glycosyltransferase, as required.

In another exemplary embodiment, a GlcNAc transferase, such as GNT1-5, is utilized to transfer PEGylated-GlcNAc to a terminal mannose residue on a glycopeptide. In a still further exemplary embodiment, an the N- and/or O-linked glycan structures are enzymatically removed from a glycopeptide to expose an amino acid or a terminal glycosyl residue that is subsequently conjugated with the modified sugar. For example, an endoglycanase is used to remove the N-linked structures of a glycopeptide to expose a terminal GlcNAc as a GlcNAc-linked-Asn on the glycopeptide. UDP-Gal-PEG and the appropriate galactosyltransferase is used to introduce the PEG-galactose functionality onto the exposed GlcNAc.

In an alternative embodiment, the modified sugar is added directly to the peptide backbone using a glycosyltransferase known to transfer sugar residues to the peptide backbone. Exemplary glycosyltransferases useful in practicing the present invention include, but are not limited to, GalNAc transferases (GalNAc T1-14), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

Enzymes and reaction conditions for preparing the conjugates of the present invention are discussed in detail in the parent of the instant application as well as co-owned published PCT patent applications WO 03/031464, WO 04/033651, WO 04/099231.

In a selected embodiment, a G-CSF peptide, expressed in insect cells, is remodeled such that glycans on the remodeled glycopeptide include a GlcNAc-Gal glycosyl residue. The addition of GlcNAc and Gal can occur as separate reactions or as a single reaction in a single vessel. In this example, GlcNAc-transferase I and Gal-transferase I are used. The modified sialyl moiety is added using ST3Gal-III.

In another embodiment, the addition of GlcNAc, Gal and modified Sia can also occur in a single reaction vessel, using the enzymes set forth above. Each of the enzymatic remodeling and glycoPEGylation steps are carried out individually.

When the peptide is expressed in mammalian cells, different methods are of use. In one embodiment, the peptide is conjugated without need for remodeling prior to conjugation by contacting the peptide with a sialyltransferase that transfers the modified sialic acid directly onto a sialic acid on the peptide forming Sia-Sia-L-$R^1$, or exchanges a sialic acid on the peptide for the modified sialic acid, forming Sia-L-$R^1$. An exemplary enzyme of use in this method is CST-II. Other enzymes that add sialic acid to sialic acid are known to those of skill in the art and examples of such enzymes are set forth the figures appended hereto.

In yet another method of preparing the conjugates of the invention, the peptide expressed in a mammalian system is desialylated using a sialidase. The exposed Gal residue is sialylated with a modified sialic acid using a sialyltransferase specific for O-linked glycans, providing an G-CSF peptide with an O-linked modified glycan. The desialylated, modified G-CSF peptide is optionally partially or fully re-sialylated by using a sialyltransferase such as ST3GalIII.

In another aspect, the invention provides a method of making a PEGylated G-CSF of the invention. The method includes: (a) contacting a substrate G-CSF peptide comprising
a glycosyl group selected from:

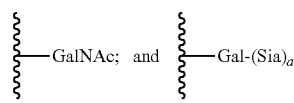

with a PEG-sialic acid donor having the formula:

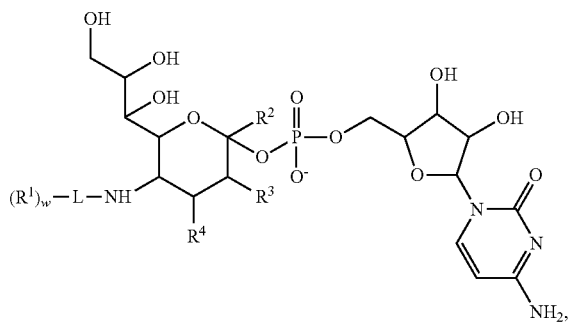

and an enzyme that transfers PEG-sialic acid from said donor onto a member selected from the GalNAc, Gal and the Sia of said glycosyl group, under conditions appropriate for said transfer. An exemplary modified sialic acid donor is CMP-sialic acid modified, through a linker moiety, with a polymer, e.g., a straight chain or branched poly(ethylene glycol) moiety. As discussed herein, the peptide is optionally glycosylated with GalNAc and/or Gal and/or Sia ("Remodeled") prior to attaching the modified sugar. The remodeling steps can occur in sequence in the same vessel without purification of the glycosylated peptide between steps. Alternatively, following one or more remodeling step, the glycosylated peptide can be purified prior to submitting it to the next glycosylation or glycPEGylation step.

As illustrated in the examples and discussed further below, placement of an acceptor moiety for the PEG-sugar is accomplished in any desired number of steps. For example, in one embodiment, the addition of GalNAc to the peptide can be followed by a second step in which the PEG-sugar is conjugated to the GalNAc in the same reaction vessel. Alternatively, these two steps can be carried out in a single vessel approximately simultaneously.

In an exemplary embodiment, the PEG-sialic acid donor has the formula:

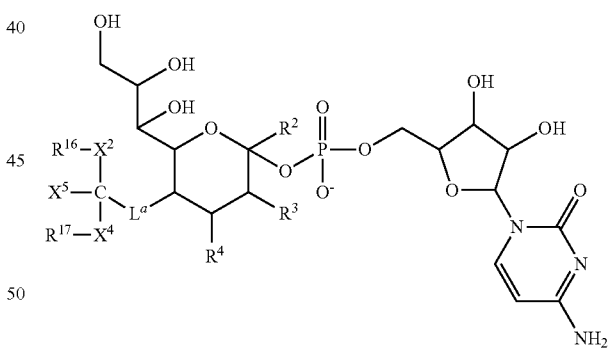

In another exemplary emodiment, the PEG-sialic acid donor has the formula:

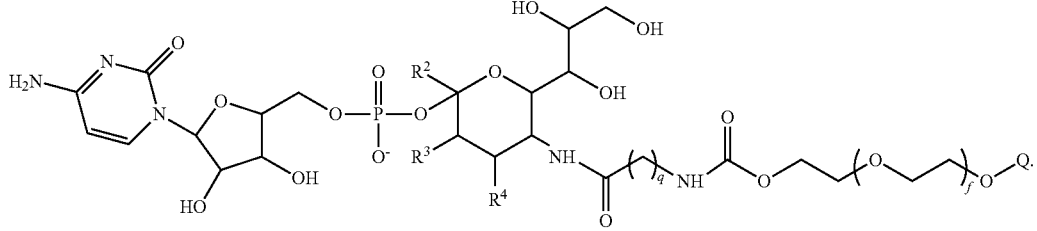

In a further exemplary embodiment, the G-CSF peptide is expressed in an appropriate expression system prior to being glycopegylated or remodeled. Exemplary expression systems include Sf-9/baculovirus and Chinese Hamster Ovary (CHO) cells.

Purification of G-CSF Conjugates

The products produced by the above processes can be used without purification. However, it is usually preferred to recover the product and one or more of the intermediates, e.g., nucleotide sugars, branched and linear PEG species, modified sugars and modified nucleotide sugars. Standard, well-known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins such as glycosyl transferases.

If the peptide is produced intracellularly, as a first step, the particulate debris, either host cells or lysed fragments, is removed. Following glycoPEGylation, the PEGylated peptide is purified by art-recognized methods, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps. Additionally, the modified glycoprotein may be purified by affinity chromatography. Finally, HPLC may be employed for final purification steps.

A protease inhibitor, e.g., methylsulfonylfluoride (PMSF) may be included in any of the foregoing steps to inhibit proteolysis and antibiotics or preservatives may be included to prevent the growth of adventitious contaminants.

Within another embodiment, supernatants from systems which produce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Other methods of use in purification include size exclusion chromatography (SEC), hydroxyapatite chromatography, hydrophobic interaction chromatography and chromatography on Blue Sepharose. These and other useful methods are illustrated in co-assigned U.S. Provisional Patent Application No. 60/678,822, filed May 6, 2005.

One or more RP-HPLC steps employing hydrophobic RP-HPLC media, e.g., silica gel having pendant methyl or other aliphatic groups, may be employed to further purify a polypeptide conjugate composition. Some or all of the foregoing purification steps, in various combinations, can also be employed to provide a homogeneous or essentially homogeneous modified glycoprotein.

The modified glycopeptide of the invention resulting from a large-scale fermentation may be purified by methods analogous to those disclosed by Urdal et al., *J. Chromatog.* 296: 171(1984). This reference describes two sequential, RP-HPLC steps for purification of recombinant human IL-2 on a preparative HPLC column. Alternatively, techniques such as affinity chromatography may be utilized to purify the modified glycoprotein.

In an exemplary embodiment, the purification is accomplished by the methods set forth in commonly owned, co-assigned U.S. Provisional Patent No. 60/665,588, filed Mar. 24, 2005.

Pharmaceutical Compositions

In another aspect, the invention provides a pharmaceutical composition. The pharmaceutical composition includes a pharmaceutically acceptable diluent and a covalent conjugate between a non-naturally-occurring, PEG moiety, therapeutic moiety or biomolecule and a glycosylated or non-glycosylated peptide. The polymer, therapeutic moiety or biomolecule is conjugated to the peptide via an intact glycosyl linking group interposed between and covalently linked to both the peptide and the polymer, therapeutic moiety or biomolecule.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered parenterally, e.g., intravenously. Thus, the invention provides compositions for parenteral administration that include the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}I$, $^{14}C$, or tritium.

The active ingredient used in the pharmaceutical compositions of the present invention is glycopegylated G-CSF and its derivatives having the biological properties of stimulating granulocyte production. Preferably, the G-CSF composition of the present invention is administered parenterally (e.g. IV, IM, SC or IP). Effective dosages are expected to vary considerably depending on the condition being treated and the route of administration but are expected to be in the range of about 0.1 (~7 U) to 100 (~7000 U) ag/kg body weight of the active material. Preferable doses for treatment of anemic conditions are about 50 to about 300 Units/kg three times a week.

Because the present invention provides a G-CSF with an enhanced in vivo residence time, the stated dosages are optionally lowered when a composition of the invention is administered.

Preparative methods for species of use in preparing the compositions of the invention are generally set forth in various patent publications, e.g., US 20040137557; WO 04/083258; and WO 04/033651. The following examples are provided to illustrate the conjugates, and methods of and of the present invention, but not to limit the claimed invention.

EXAMPLES

Example 1

GlycoPEGylation of G-CSF Produced in CHO Cells
a. Preparation of Asialo-Granulocyte-Colony Stimulation Factor (G-CSF)

G-CSF produced in CHO cells was dissolved at 2.5 mg/mL in 50 mM Tris 50 mM Tris-HCl pH 7.4, 0.15 M NaCl, 5 mM $CaCl_2$ and concentrated to 500 μL in a Centricon Plus 20 centrifugal filter. The solution was incubated with 300 mU/mL Neuraminidase II (*Vibrio cholerae*) for 16 hours at 32° C. To monitor the reaction a small aliquot of the reaction is diluted with the appropriate buffer and an IEF gel was run. The reaction mixture is then added to prewashed N-(p-aminophenyl)oxamic acid-agarose conjugate (800 μL/mL reaction volume) and the washed beads gently rotated for 24 hours at 4° C. The mixture was centrifuged at 10,000 rpm and the supernatant was collected. The beads were washed 3 times with Tris-EDTA buffer, once with 0.4 mL Tris-EDTA buffer and once with 0.2 mL of the Tris-EDTA buffer and all supernatants were pooled. The supernatant was dialyzed at 4° C. against 50 mM Tris-HCl pH 7.4, 1 M NaCl, 0.05% $NaN_3$ and then twice more against 50 mM Tris-HCl pH 7.4, 1 M NaCl, 0.05% $NaN_3$. The dialyzed solution was then concentrated using a Centricon Plus 20 centrifugal filter and stored at −20° C. The conditions for the IEF gel were run according to the procedures and reagents provided by Invitrogen. Samples of native and desialylated G-CSF were dialyzed against water and analyzed by MALDI-TOF MS.

b. Preparation of G-CSF-(alpha2,3)-Sialyl-PEG

Desialylated G-CSF was dissolved at 2.5 mg/mL in 50 mM Tris-HCl, 0.15 M NaCl, 0.05% $NaN_3$, pH 7.2. The solution was incubated with 1 mM CMP-sialic acid-PEG and 0.1 U/mL of ST3Gal1 at 32° C. for 2 days. After 2 days, the reaction mixture was purified using a Toso Haas G3000SW preparative column using PBS buffer (pH 7.1) and collecting fractions. The product of the reaction was analyzed using SDS-PAGE and IEF analysis according to the procedures and reagents supplied by Invitrogen. Samples of native and PEGylated G-CSF were dialyzed against water and analyzed by MALDI-TOF MS.

c. Preparation of G-CSF-(alpha2,8)-Sialyl-PEG

G-CSF produced in CHO cells, which contains an alpha2, 3-sialylated O-linked glycan, were dissolved at 2.5 mg/mL in 50 mM Tris-HCl, 0.15 M NaCl, 0.05% $NaN_3$, pH 7.2. The solution was incubated with 1 mM CMP-sialic acid-PEG and 0.1 U/mL of CST-II at 32° C. for 2 days. After 2 days, the reaction mixture was purified using a Toso Haas G3000SW preparative column using PBS buffer (pH 7.1) and collecting fractions based. The product of the reaction was analyzed using SDS-PAGE and IEF analysis according to the procedures and reagents supplied by Invitrogen. Samples of native and PEGylated G-CSF were dialyzed against water and analyzed by MALDI-TOF MS.

d. Preparation of G-CSF-(alpha2,6)-Sialyl-PEG

G-CSF, containing only O-linked GalNAc, is dissolved at 2.5 mg/mL in 50 mM Tris-HCl, 0.15 M NaCl, 0.05% NaN$_3$, pH 7.2. The solution was incubated with 1 mM CMP-sialic acid-PEG and 0.1 U/mL of ST6GalNAcI or II at 32° C. for 2 days. After 2 days, the reaction mixture was purified using a Toso Haas G3000SW preparative column using PBS buffer (pH 7.1) and collecting fractions. The product of the reaction was analyzed using SDS-PAGE and IEF analysis according to the procedures and reagents supplied by Invitrogen. Samples of native and PEGylated G-CSF were dialyzed against water and analyzed by MALDI-TOF MS.

G-CSF produced in CHO cells was treated with Arthrobacter sialidase and was then purified by size exclusion on Superdex 75 and was treated with ST3 Gal1 or ST3 Gal2 and then with CMP-SA-PEG 20 kDa. The resulting molecule was purified by ion exchange and gel filtration and analysis by SDS PAGE demonstrated that the PEGylation was complete. This is the first demonstration of glycoPEGylation of an O-linked glycan.

Example 2

Two Enzyme Method in Two Pots

The following example illustrates the preparation of G-CSF-GalNAc-SA-PEG in two sequential steps wherein each intermediate product is purified before it is used in the next step.

a. Preparation of G-CSF-GalNAc (pH 6.2) from G-CSF and UDP-Ga/NAc using GalNAc-T2.

G-CSF (960 mcg) in 3.2 mL of packaged buffer was concentrated by utrafiltration using an UF filter (MWCO 5K) and then reconstituted with 1 mL of 25 mM MES buffer (pH 6.2, 0.005% NaN$_3$). UDP-GalNAc (6 mg, 9.24 mM), GalNAc-T2 (40 µL, 0.04 U), and 100 mM MnCl$_2$ (40 µL, 4 mM) were then added and the resulting solution was incubated at room temperature.

After 24 h, MALDI indicated the reaction was complete. The reaction mixture was directly subjected to HPLC purification using SEC (Superdex 75 and Superdex 200) and an elution buffer comprising of PBS (phosphate buffered saline, pH 4.9 and 0.005% Tween 80). The collected peak of G-CSF-GalNAc was concentrated using a Centricon 5 KDa MWCO filter to about 150 µL and the volume adjusted to 1 mL using PBS (phosphate buffered saline, pH 4.9 and 0.005% Tween 80). Final protein concentration 1 mg/mL (A$_{280}$), yield 100%. The sample was stored at 4° C.

b. Preparation of G-CSF-GalNAc-SA-PEG using Purified G-CSF-GalNAc, CMP-SA-PEG (20 KDa) and Mouse ST6GalNAc-1 (pH 6.2).

The G-CSF-GalNAc solution containing 1 mg of protein was buffer exchanged into 25 mM MES buffer (pH 6.2, 0.005% NaN$_3$) and CMP-SA-PEG (20 KDa) (5 mg, 0.25 umol) was added. After dissolving, MnCl$_2$ (100 µL, 100 mM solution) and ST6GalNAc-I (100 µL, mouse enzyme) was added and the reaction mixture rocked slowly at 32° C. for three days. The reaction mixture was concentrated by ultrifiltration (MWCO 5K) and buffer exchanged with 25 mM NaOAc (pH 4.9) one time and then concentrated to 1 mL of total volume. The product was then purified using SP-sepharose (A: 25 mM NaOAc+0.005% tween-80 pH 4.5; B: 25 mM NaOAc+0.005% Tween-80 pH 4.5+2M NaCl) at retention time 13-18 mins and SEC (Superdex 75; PBS-pH 7.2, 0.005% Tween 80) at retention time 8.6 mins (superdex 75, flow 1 mL/min) The desired fractions were collected, concentrated to 0.5 mL and stored at 4° C.

Example 3

One Pot Method to Make G-CSF-GalNAc-SA-PEG with Simultaneous Addition of Enzymes The following example illustrates the preparation of G-CSF-GalNAc -SA-PEG in one pot using simultaneous addition of enzymes
a. One Potprocess Using Mouse ST6GalNAc-I (pH 6.0).

G-CSF (960 µg of protein dissolved in 3.2 mL of the product formulation buffer) was concentrated by ultrafiltration (MWCO 5K) to 0.5 mL and reconstituted with 25 mM MES buffer (pH 6.0, 0.005% NaN$_3$) to a total volume of about 1 mL or a protein concentration of 1 mg/mL. UDP-GalNAc (6 mg, 9.21 µmol), GalNAc-T2 (80 µL, 80 mU), CMP-SA-PEG (20 KDa) (6 mg, 0.3 µmol) and mouse enzyme ST6GalNAc-I (120 µL) and 100 mM MnCl$_2$(50 µL) were then added. The solution was rocked at 32° C. for 48 h and purified using standard chromatography conditions on SP-Sepharose. A total of 0.5 mg of protein (A$_{280}$) was obtained or about a 50% overall yield. The product structure was confirmed by analysis with both MALDI and SDS-PAGE.

b. One Pot Process Using Chicken ST6GalNAc-I (pH 6.0).

14.4 mg of G-CSF; was concentrated to 3 mL final volume, buffer exchanged with 25 mM MES buffer (pH 6.0, 0.05% NaN$_3$, 0.004% Tween 80) and the volume was adjusted to 13 mL. The UDP-GalNAc (90 mg, 150 µmole), GalNAc-T2 (0.59 U), CMP-SA-PEG-20 KDa (90 mg), chicken ST6GalNAc-I (0.44 U), and 100 mM MnCl$_2$ (600 mcL) were then added. The resulting mixture stood at room temperature for 60 h. The reaction mixture was then concentrated using a UF (MWCO 5K) and centrifugation. The residue (about 2 mL) was dissolved in 25 mM NaOAc buffer (pH 4.5) and concentrated again to 5 mL final volume. This sample was purified using SP-sepharose for about 10-23 min, SEC (Superdex 75, 17 min, flow rate 0.5 mL/min) and an additional SEC (Superdex 200, 23 min, flow rate 0.5 mL/min), to yield 3.6 mg (25% overall yield) of G-CSF-GalNAc-SA-PEG-20 KDa (A$_{280}$ and BCA method).

Example 4

One Pot Method to Make G-CSF-GalNAc-Gal-SA-PEG with Sequential Addition of Enzymes The following example illustrates a method for making G-CSF-GalNAc-Gal-SA-PEG in one pot with sequential addition of enzymes.
a. Startingfrom GalNAc-G-CSF 1. Preparation of G-CSF-GalNAc (pH 6.2) from G-CSF and UDP-GalNAc Using GalNAc-T2

G-CSF (960 mcg) in 3.2 mL of packaged buffer was concentrated by utrafiltration using an UF filter (MWCO 5K) and then reconstituted with 1 mL of 25 mM MES buffer (pH 6.2, 0.005% NaN$_3$). UDP-GalNAc (6 mg, 9.24 mM), GalNAc-T2 (40 µL, 0.04 U), and 100 mM MnCl$_2$ (40 µL, 4 mM) were then added and the resulting solution was incubated at room temperature.

2. Preparation of G-CSF-GalNAc-Gal-SA-PEG from G-CSF-GalNAc; UDP-Galactose, SA-PEG-20 kDa, and the Appropriate Enzymes The UDP-galactose (4 mg, 6.5 µmoles), core-1-Gal-T (320 µL, 160 mU), CMP-SA-PEG-20 kDa (8 mg, 0.4 µmole), ST3Gal2 (80 µL, 0.07 mU) and 100 mM MnCl$_2$(80 µL) were directly added to the crude reaction mixture of the G-CSF-GalNAc (1.5 mg) in 1.5 mL 25 mM MES buffer (pH 6.0) from step a, above. The resulting mixture was incubated at 32° C. for 60 h. The reaction mixture was centrifuged and the solution was concentrated using ultrafiltration (MWCO 5K) to 0.2 mL, and then redissolved with 25 mM NaOAc (pH 4.5) to a final volume of 1 mL. The product was purified using SP-Sepharose (retention time of between 10-15 min), the peak fraction were concentrated using a spin filter (MWCO 5K) and the residue purified further using SEC (Superdex 75, retention time of 10.2 min). After concentration using a spin filter (MWCO 5K), the protein was diluted to 1 mL using formulation buffer with PBS, 2.5% mannitol, 0.005% polysorbate, pH 6.5 and formulated at a protein concentration of 850 jig protein per mL ($A_{280}$). The overall yield was 55%.

Example 5

One Pot Method to Make G-CSF-GalNAc-Gal-SA-PEG with Simultaneous Addition of Enzymes
a. Starting from G-CSF.

G-CSF (960 mcg, 3.2 mL) was concentrated by ultrafiltration (MWCO 5K) and reconstituted with 25 mM Mes buffer (pH 6.0, 0.005% $NaN_3$). The total volume of the G-CSF solution was about 1 mg/mL. UDP-GalNAc (6 mg), GalNAc-T2 (80 µL, ~80 µU), UDP-Gal (6 mg ), Corel GalT (160 µL, 80 µU), CMP-SA-PEG(20K) (6 mg) and a sialyltransferase, e.g., ST3Gal1 (160 µL, 120 µU), 100 mM $MnCl_2$ (40 µL) were added. The resulting mixture was incubated at 32° C. for 48 h. Purification was performed as described below using IEX and SEC. The resulting fraction containing the product were concentrated using ultrafiltration (MWCO 5K) and the volume was adjusted to about 1 mL with buffer. The protein concentration was determined to be 0.392 mg/mL by A280, giving an overall yield of 40% from G-CSF.

Example 6

Preparation of Cysteine-$PEG_2$ (2)

tosylate of molecular mass 20 kilodalton (Ts; 1.0 g, 0.05 mmol) was added in several portions over 2 hours. The mixture was stirred at room temperature for 5 days, and concentrated by rotary evaporation. The residue was diluted with water (30 mL), and stirred at room temperature for 2 hours to destroy any excess 20 kilodalton mPEG-O-tosylate. The solution was then neutralized with acetic acid, the pH adjusted to pH 5.0 and loaded onto a reversed phase chromatography (C-18 silica) column. The column was eluted with a gradient of methanol/water (the product elutes at about 70% methanol), product elution monitored by evaporative light scattering, and the appropriate fractions collected and diluted with water (500 mL). This solution was chromatographed (ion exchange, XK 50 Q, BIG Beads, 300 ml, hydroxide form; gradient of water to water/acetic acid-0.75N) and the pH of the appropriate fractions lowered to 6.0 with acetic acid. This solution was then captured on a reversed phase column (C-18 silica) and eluted with a gradient of methanol/water as described above. The product fractions were pooled, concentrated, redissolved in water and freeze-dried to afford 453 mg (44%) of a white solid (1). Structural data for the compound were as follows: $^1$H-NMR (500 MHz; $D_2O$), δ 2.83 (t, 2H, O—C—$CH_2$—S), 3.05 (q, 1H, S—C HH—CHN), 3.18 (q, 1H, (q, 1H, S—CHH—CHN), 3.38 (s, 3H, $CH_3O$), 3.7 (t, $OCH_2CH_2O$), 3.95 (q, 1H, CHN). The purity of the product was confirmed by SDS PAGE.
b. Synthesis of Compound 2 (Cysteine-$PEG_2$)

Triethylamine (~0.5 mL) was added dropwise to a solution of compound 1 (440 mg, 22 µmol) dissolved in anhydrous $CH_2Cl_2$ (30 mL) until the solution was basic. A solution of 20 kilodalton mPEG-O-p-nitrophenyl carbonate (660 mg, 33 µmol) and N-hydroxysuccinimide (3.6 mg, 30.8 µmol) in $CH_2Cl_2$ (20 mL) was added in several portions over 1 hour at room temperature. The reaction mixture was stirred at room temperature for 24 hours. The solvent was then removed by rotary evaporation, the residue was dissolved in water (100

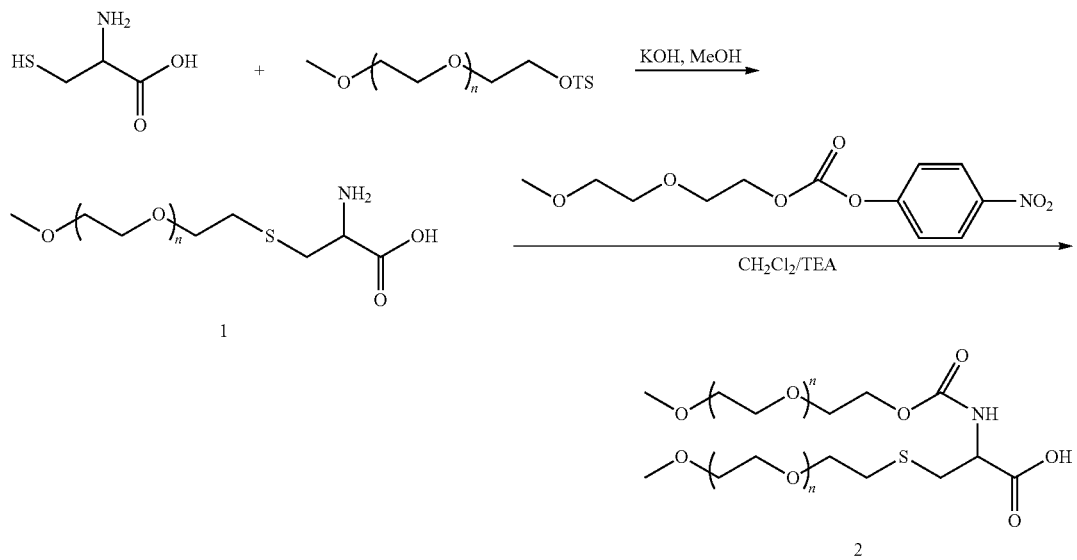

a. Synthesis of Compound 1

Potassium hydroxide (84.2 mg, 1.5 mmol, as a powder) was added to a solution of L-cysteine (93.7mg, 0.75 mmol) in anhydrous methanol (20 L) under argon. The mixture was stirred at room temperature for 30 min, and then mPEG-O- mL), and the pH adjusted to 9.5 with 1.0 N NaOH. The basic solution was stirred at room temperature for 2 hours and was then neutralized with acetic acid to a pH 7.0. The solution was then loaded onto a reversed phase chromatography (C-18 silica) column. The column was eluted with a gradient of methanol/water (the product elutes at about 70% methanol), product elution monitored by evaporative light scattering, and the appropriate fractions collected and diluted with water (500 mL). This solution was chromatographed (ion exchange, XK 50 Q, BIG Beads, 300 mL, hydroxide form; gradient of water to water/acetic acid-0.75N) and the pH of the appropriate fractions lowered to 6.0 with acetic acid. This solution was then captured on a reversed phase column (C-18 silica) and eluted with a gradient of methanol/water as described above. The product fractions were pooled, concentrated, redissolved in water and freeze-dried to afford 575 mg (70%) of a white solid (2). Structural data for the compound were as follows:

$^1$H-NMR (500 MHz; $D_2O$), δ 2.83 (t, 2H, O—C—$CH_2$—S), 2.95 (t, 2H, O—C—$CH_2$—S), 3.12 (q, 1H, S—CHH—CHN), 3.39 (s, 3H $CH_3O$), 3.71 (t, $OCH_2CH_2O$). The purity of the product was confirmed by SDS PAGE.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A Granulocyte Colony Stimulating Factor peptide conjugate comprising a glycosyl linking group attached to an amino acid residue of said peptide, said glycosyl linking group comprising a modified sialyl residue having the formula:

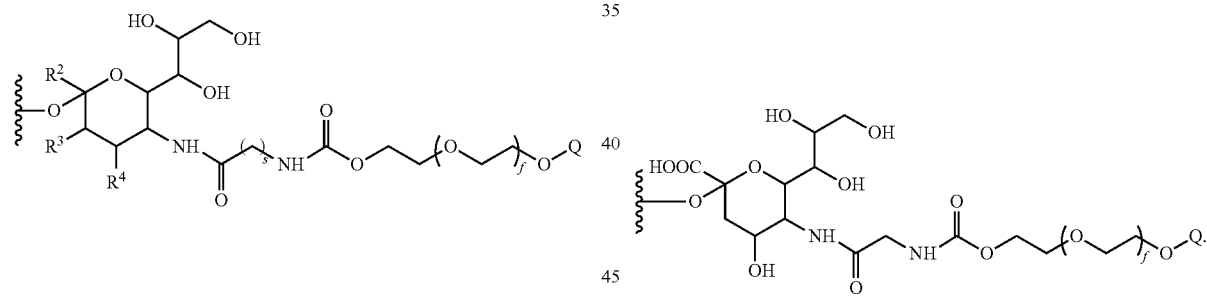

wherein
$R^2$ is H, $CH_2OR^7$, $COOR^7$, $COO^-$ or $OR^7$
wherein
$R^7$ represents H, substituted or unsubstituted alkyl or substituted or unsubstituted heteroalkyl;
$R^3$ and $R^4$ are members independently selected from H, substituted or unsubstituted alkyl, $OR^8$, $NHC(O)R^9$ wherein
$R^8$ and $R^9$ are independently selected from H, substituted or unsubstituted alkyl, substituted or unsubstituted heteroalkyl or sialic acid;
s is an integer from 1 to 20;
f is an integer from 1 to 2500; and
Q is a member selected from H and substituted or unsubstituted $C_1$-$C_6$ alkyl.

2. The peptide conjugate according to claim 1, wherein said modified sialyl residue has the formula:

3. The peptide conjugate according to claim 1, wherein Q is selected from H and $CH_3$.

4. The peptide conjugate according to claim 1, wherein said glycosyl linking group comprises the formula:

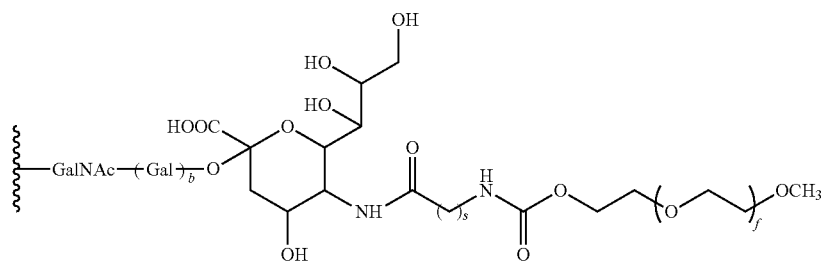

in which
b is 0 or 1.

5. The peptide conjugate according to claim 4, wherein s is 1; b is 0 and f is an integer from about 200 to about 500.

6. The peptide conjugate according to claim 5, wherein s is 1; b is 0 and f is an integer from about 400 to about 500.

7. The peptide conjugate according to claim 1, wherein said amino acid residue is a member selected from serine or threonine.

8. The peptide conjugate according to claim 1, wherein said peptide has the amino acid sequence of SEQ ID NO:1.

9. The peptide conjugate according to claim 8, wherein said amino acid residue is a threonine at position 134 of SEQ ID NO:1.

10. A pharmaceutical formulation comprising the Granulocyte Colony Stimulating Factor peptide conjugate according to claim 1, and a pharmaceutically acceptable carrier.

* * * * *